(12) United States Patent
Stoessel et al.

(10) Patent No.: US 9,831,448 B2
(45) Date of Patent: Nov. 28, 2017

(54) METAL COMPLEXES

(71) Applicant: Merck Patent GmbH, Darmstadt (DE)

(72) Inventors: Philipp Stoessel, Frankfurt am Main (DE); Nils Koenen, Darmstadt (DE); Esther Breuning, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 99 days.

(21) Appl. No.: 15/021,076

(22) PCT Filed: Aug. 12, 2014

(86) PCT No.: PCT/EP2014/002209
§ 371 (c)(1),
(2) Date: Mar. 10, 2016

(87) PCT Pub. No.: WO2015/036074
PCT Pub. Date: Mar. 19, 2015

(65) Prior Publication Data
US 2016/0233443 A1    Aug. 11, 2016

(30) Foreign Application Priority Data
Sep. 11, 2013 (EP) .................................. 13004411

(51) Int. Cl.
| | | |
|---|---|---|
| *H01L 51/50* | (2006.01) | |
| *H01L 51/00* | (2006.01) | |
| *C07F 15/00* | (2006.01) | |
| *C09K 11/06* | (2006.01) | |
| *H05B 33/10* | (2006.01) | |
| *C09K 11/02* | (2006.01) | |
| *C07D 221/18* | (2006.01) | |
| *C07D 221/20* | (2006.01) | |
| *C07D 221/22* | (2006.01) | |
| *C07D 471/04* | (2006.01) | |
| *C07D 471/14* | (2006.01) | |
| *C07D 491/048* | (2006.01) | |
| *C07D 491/056* | (2006.01) | |
| *C07D 491/14* | (2006.01) | |
| *C07D 495/04* | (2006.01) | |
| *C07D 495/14* | (2006.01) | |

(52) U.S. Cl.
CPC ........ *H01L 51/0085* (2013.01); *C07D 221/18* (2013.01); *C07D 221/20* (2013.01); *C07D 221/22* (2013.01); *C07D 471/04* (2013.01); *C07D 471/14* (2013.01); *C07D 491/048* (2013.01); *C07D 491/056* (2013.01); *C07D 491/14* (2013.01); *C07D 495/04* (2013.01); *C07D 495/14* (2013.01); *C07F 15/0033* (2013.01); *C09K 11/025* (2013.01); *C09K 11/06* (2013.01); *H01L 51/0067* (2013.01); *H01L 51/0072* (2013.01); *H01L 51/504* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/5016* (2013.01); *H01L 2251/5384* (2013.01); *Y02E 10/549* (2013.01)

(58) Field of Classification Search
None
See application file for complete search history.

(56) References Cited

U.S. PATENT DOCUMENTS

| | | |
|---|---|---|
| 9,181,289 B2 | 11/2015 | Stoessel et al. |
| 2015/0333280 A1 | 11/2015 | Stoessel et al. |
| 2015/0349277 A1 | 12/2015 | Stoessel et al. |

FOREIGN PATENT DOCUMENTS

| | | | | |
|---|---|---|---|---|
| CN | 102574882 B | 11/2015 | | |
| DE | 102009048791 A1 | 4/2011 | | |
| DE | 102009049587 A1 | * 4/2011 | .......... | C07F 15/0033 |
| WO | WO-2010/108579 A1 | 9/2010 | | |
| WO | 2014094960 A1 | 6/2014 | | |
| WO | 2014094961 A1 | 6/2014 | | |

OTHER PUBLICATIONS

Chinese Office Action with Search Report for Chinese Application No. 201480050186.X, dated May 2, 2017, 10 pages.
Lo et al., "Synthesis, Photophysical and Electrochemical Properties, and Biological Labelling Studies of Luminescent Cyclometallated Iridium (III) Bipyridine-Aldehyde Complexes", Inorganica Chimica Acta, 2004, vol. 357, pp. 3109-3118.
Lamansky et al., "Synthesis and Characterization of Phosphorescent Cyclometalated Iridium Complexes", Inorganic Chemistry, 2001, vol. 40, pp. 1704-1711.

* cited by examiner

*Primary Examiner* — Vu A Nguyen
(74) *Attorney, Agent, or Firm* — RatnerPrestia

(57) ABSTRACT

The invention relates to metal complexes and to electronic devices, in particular organic electroluminescence devices, containing said metal complexes.

16 Claims, No Drawings

METAL COMPLEXES

RELATED APPLICATIONS

This application is a national stage entry, filed pursuant to 35 U.S.C. § 371, of PCT/EP2014/002209, filed Aug. 12, 2014, which claims the benefit of German Patent Application No. 13004411.8, filed Sep. 11, 2013, which is incorporated herein by reference in its entirety.

The present invention relates to metal complexes and to electronic devices, especially organic electroluminescent devices, comprising these metal complexes.

The structure of organic electroluminescent devices (OLEDs) in which organic semiconductors are used as functional materials is described, for example, in U.S. Pat. No. 4,539,507, U.S. Pat. No. 5,151,629, EP 0676461 and WO 98/27136.

These are increasingly using organometallic complexes which exhibit phosphorescence rather than fluorescence as emitting materials (M. A. Baldo et al., Appl. Phys. Lett. 1999, 75, 4-6). For quantum-mechanical reasons, up to four times the energy efficiency and power efficiency is possible using organometallic compounds as phosphorescent emitters. In general terms, however, there is still a need for improvement in OLEDs which exhibit triplet emission, especially with regard to efficiency, operating voltage and lifetime.

According to the prior art, triplet emitters used in phosphorescent OLEDs are especially iridium complexes, for example iridium complexes containing benzo[h]quinoline derivatives as ligands. In general terms, still further improvements in phosphorescent emitters are desirable, especially with regard to efficiency, operating voltage and lifetime.

It is therefore an object of the present invention to provide novel metal complexes which are suitable as emitters for use in OLEDs and at the same time lead to improved OLED properties, especially with regard to efficiency, operating voltage and/or lifetime.

It has been found that, surprisingly, particular metal chelate complexes described further down, which have a fused-on aliphatic five-membered ring in the ligand, achieve this object and exhibit improved properties in an organic electroluminescent device. More particularly, these metal complexes exhibit improved efficiency and lifetime compared to the analogous metal complexes that do not contain this fused-on aliphatic five-membered ring. The present invention therefore provides these metal complexes and electronic devices, especially organic electroluminescent devices, containing these complexes.

The invention thus provides a compound of formula (1)

[Ir(L)$_n$(L')$_m$]  formula (1)

where the compound of the general formula (1) contains a substructure Ir(L)$_n$ of the formula (2):

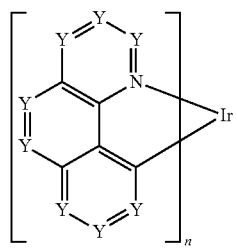

Formula (2)

where the symbols and indices used are as follows:

Y is the same or different at each instance and is CR or N, with the proviso that not more than one symbol Y per cycle is N, or two adjacent symbols Y together are a group of the following formula (3):

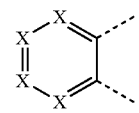

Formula (3)

where the dotted bonds symbolize the linkage of this group in the ligand;

X is the same or different at each instance and is CR or N, with the proviso that not more than two symbols X per ligand are N;

R is the same or different at each instance and is H, D, F, Cl, Br, I, N(R$^1$)$_2$, CN, Si(R$^1$)$_3$, B(OR$^1$)$_2$, C(=O)R$^1$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more R$^1$ radicals, where one or more nonadjacent CH$_2$ groups may be replaced by R$^1$C=CR$^1$, Si(R$^1$)$_2$, C=O, NR$^1$, O, S or CONR$^1$ and where one or more hydrogen atoms may be replaced by D, F or CN, or an aromatic or heteroaromatic ring system which has 5 to 60 aromatic ring atoms and may be substituted in each case by one or more R$^1$ radicals, or an aryloxy or heteroaryloxy group which has 5 to 60 aromatic ring atoms and may be substituted by one or more R$^1$ radicals, or a diarylamino group, diheteroarylamino group or arylheteroarylamino group which has 10 to 40 aromatic ring atoms and may be substituted by one or more R$^1$ radicals; at the same time, two or more adjacent R radicals together may also form a mono- or polycyclic, aliphatic, aromatic and/or benzo-fused ring system;

R$^1$ is the same or different at each instance and is H, D, F, Cl, Br, I, N(R$^2$)$_2$, CN, Si(R$^2$)$_3$, B(OR$^2$)$_2$, C(=O)R$^2$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more R$^2$ radicals, where one or more nonadjacent CH$_2$ groups may be replaced by R$^2$C=CR$^2$, Si(R$^2$)$_2$, C=O, NR$^2$, O, S or CONR$^2$ and where one or more hydrogen atoms may be replaced by D, F or CN, or an aromatic or heteroaromatic ring system which has 5 to 60 aromatic ring atoms and may be substituted in each case by one or more R$^2$ radicals, or an aryloxy or heteroaryloxy group which has 5 to 60 aromatic ring atoms and may be substituted by one or more R$^2$ radicals, or a diarylamino group, diheteroarylamino group or arylheteroarylamino group which has 10 to 40 aromatic ring atoms and may be substituted by one or more R$^2$ radicals; at the same time, two or more adjacent R$^1$ radicals together may also form a mono- or polycyclic, aliphatic ring system;

R$^2$ is the same or different at each instance and is H, D, F or an aliphatic, aromatic and/or heteroaromatic organic radical having 1 to 20 carbon atoms, especially a hydrocarbyl radical, in which one or more hydrogen atoms may also be replaced by D or F; at the same time, two or more R$^2$ substituents together may also form a mono- or polycyclic, aliphatic or aromatic ring system;

L' is the same or different at each instance and is a mono- or bidentate ligand;

n is 1, 2 or 3;

m is 0, 1, 2, 3 or 4;

characterized in that, in the substructure of the formula (2), two adjacent Y groups are CR and the respective R radicals together with the carbon atoms form a ring of the following formula (4) or formula (5), and/or in that two adjacent Y groups are a group of the formula (3) and two adjacent X groups in this group of the formula (3) are CR and the respective R radicals together with the carbon atoms form a ring of the following formula (4) or formula (5):

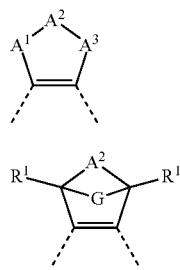

Formula (4)

Formula (5)

where $R^1$ and $R^2$ are as defined above, the dotted bonds signify the linkage of the two carbon atoms in the ligand and, in addition:

$A^1$, $A^3$ is the same or different at each instance and is $C(R^3)_2$, O, S, $NR^3$ or C(=O);

$A^2$ is $C(R^1)_2$, O, S, $NR^3$ or C(=O);

G is an alkylene group which has 1, 2 or 3 carbon atoms and may be substituted by one or more $R^2$ radicals, —$CR^2$=$CR^2$— or an ortho-bonded arylene or heteroarylene group which has 5 to 14 aromatic ring atoms and may be substituted by one or more $R^2$ radicals;

$R^3$ is the same or different at each instance and is F, a straight-chain alkyl or alkoxy group having 1 to 10 carbon atoms, a branched or cyclic alkyl or alkoxy group having 3 to 10 carbon atoms, each of which may be substituted by one or more $R^2$ radicals, where one or more nonadjacent $CH_2$ groups may be replaced by $R^2C$=$CR^2$, C≡C, $Si(R^2)_2$, C=O, $NR^2$, O, S or $CONR^2$, and where one or more hydrogen atoms may be replaced by D or F, or an aromatic or heteroaromatic ring system which has 5 to 24 aromatic ring atoms and may be substituted in each case by one or more $R^2$ radicals, or an aryloxy or heteroaryloxy group which has 5 to 24 aromatic ring atoms and may be substituted by one or more $R^2$ radicals, or an aralkyl or heteroaralkyl group which has 5 to 24 aromatic ring atoms and may be substituted by one or more $R^2$ radicals; at the same time, two $R^3$ radicals bonded to the same carbon atom together may form an aliphatic or aromatic ring system and thus form a spiro system; in addition, $R^3$ with an adjacent R or $R^1$ radical may form an aliphatic ring system;

with the proviso that no two heteroatoms in $A^1$-$A^2$-$A^3$ are bonded directly to one another and no two C=O groups are bonded directly to one another.

In these formulae, the indices n and m are chosen such that the coordination number on the iridium corresponds to 6 in total. This is especially dependent on how many ligands L are present and whether the ligands L' are mono- or bidentate ligands.

In the description which follows, "adjacent Y groups" and "adjacent X groups" mean that the Y and X groups are bonded directly to one another in the structure.

Moreover, "adjacent" in the definition of the radicals means that these radicals are bonded to the same carbon atom or carbon atoms bonded directly to one another or, when they are not bonded to directly bonded carbon atoms, means that the position is the closest possible in which a substituent can be bonded. This is elucidated once again for adjacent radicals with reference to a specific ligand in the following schematic diagram:

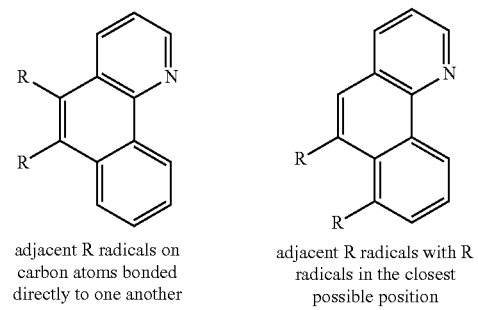

adjacent R radicals on carbon atoms bonded directly to one another adjacent R radicals with R radicals in the closest possible position An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit (preferably less than 10% of the atoms other than H), for example an $sp^3$-hybridized carbon, nitrogen or oxygen atom or a carbonyl group. For example, systems such as 9,9'-spirobifluorene, 9,9-diarylfluorene, triarylamine, diaryl ethers, stilbene, etc. are also to be regarded as aromatic ring systems in the context of this invention, and likewise systems in which two or more aryl groups are joined, for example, by a linear or cyclic alkylene group or by a silylene group.

A cyclic alkyl, alkoxy or thioalkoxy group in the context of this invention is understood to mean a monocyclic, bicyclic or polycyclic group.

In the context of the present invention, a $C_1$- to $C_{40}$-alkyl group in which individual hydrogen atoms or $CH_2$ groups may be replaced by the abovementioned groups are understood, for example, to mean the methyl, ethyl, n-propyl, i-propyl, n-butyl, i-butyl, s-butyl, t-butyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, cyclohexyl, 2-methylpentyl, neohexyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl or 2,2,2-trifluoroethyl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system which has 5-60 aromatic ring atoms and may also be substituted in each case by the abovementioned R radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The complexes of the invention may be facial or pseudofacial, or they may be meridional or pseudomeridional.

In a preferred embodiment, the index n=3, meaning that the complex is a homoleptic metal complex and the index m=0.

In a further preferred embodiment, the index n=2 and m=1; the complex of the invention contains two ligands L and one bidentate ligand L'. It is preferable here when the ligand L' is a ligand which coordinates to the iridium via one carbon atom and one nitrogen atom, one carbon atom and one oxygen atom, two oxygen atoms, two nitrogen atoms or one oxygen and one nitrogen atom.

In a further preferred embodiment, the index n=1 and m=2; the complex of the invention contains one ligand L and two bidentate ligands L'. This is preferable especially when the ligand L' is an ortho-metalated ligand which coordinates to the iridium via one carbon atom and one nitrogen or oxygen atom.

In a further preferred embodiment of the invention, no, one or two groups of the formula (3) are present in the compounds of the invention. The substructures $Ir(L)_n$ are therefore preferably selected from the following formulae (6) to (15):

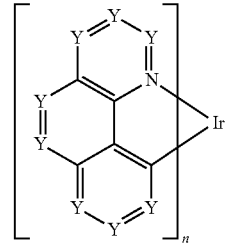

Formula (6)

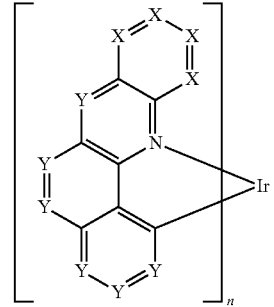

Formula (7)

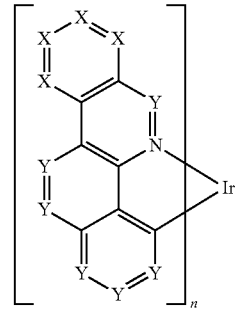

Formula (8)

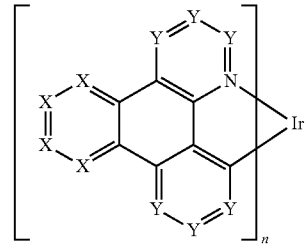

Formula (9)

-continued

Formula (10)

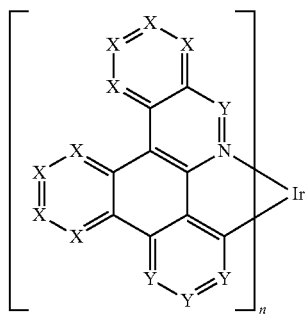

Formula (11)

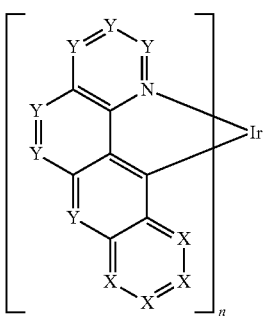

Formula (12)

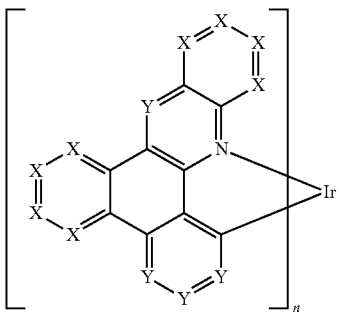

Formula (13)

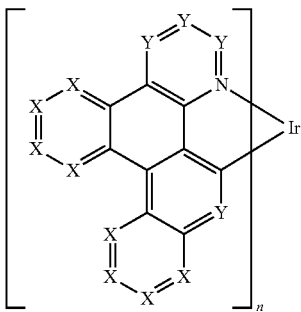

Formula (14)

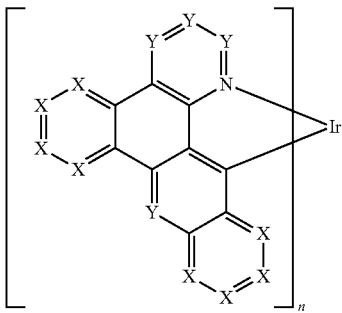

-continued

Formula (15)

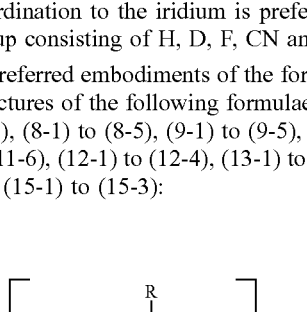

where Y is the same or different at each instance and is CR or N and the further symbols and indices are as defined above.

In a preferred embodiment of the invention, a total of 0, 1 or 2 of the symbols Y and, if present, X in the ligand L are N. More preferably, a total of 0 or 1 of the symbols Y and, if present, X in the ligand L are N. Most preferably, all symbols X and Y are CR.

In a preferred embodiment of the invention, the Y group in the ortho position to the coordination to the iridium is CR. In this radical, R bonded in the ortho position to the coordination to the iridium is preferably selected from the group consisting of H, D, F, CN and methyl.

Preferred embodiments of the formula (6) to (12) are the structures of the following formulae (6-1) to (6-7), (7-1) to (7-6), (8-1) to (8-5), (9-1) to (9-5), (10-1) to (10-5), (11-1) to (11-6), (12-1) to (12-4), (13-1) to (13-3), (14-1) to (14-4) and (15-1) to (15-3):

Formula (6-1)

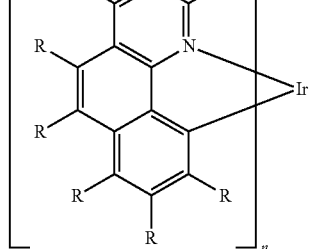

Formula (6-2)

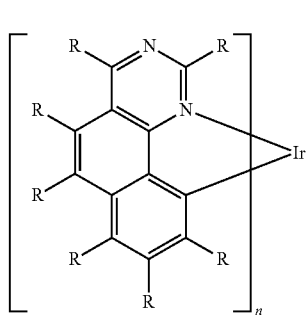

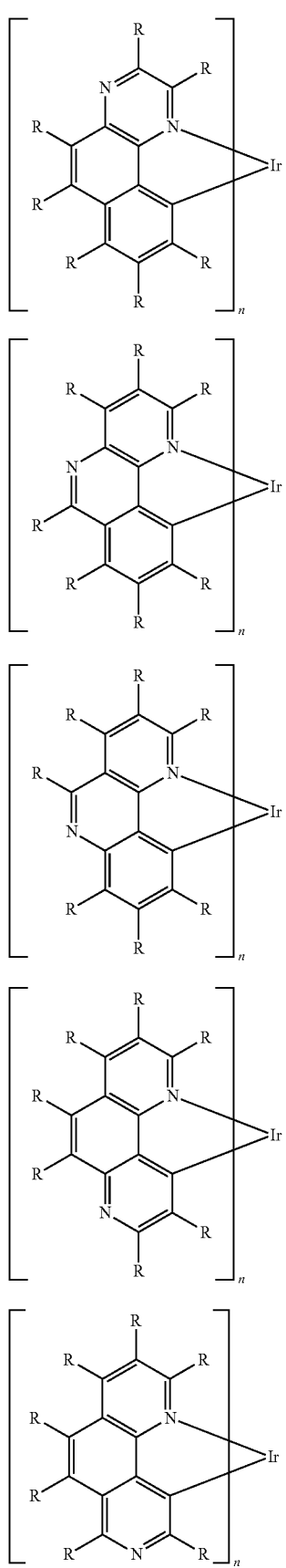
Formula (6-3)
Formula (6-4)
Formula (6-5)
Formula (6-6)
Formula (6-7)
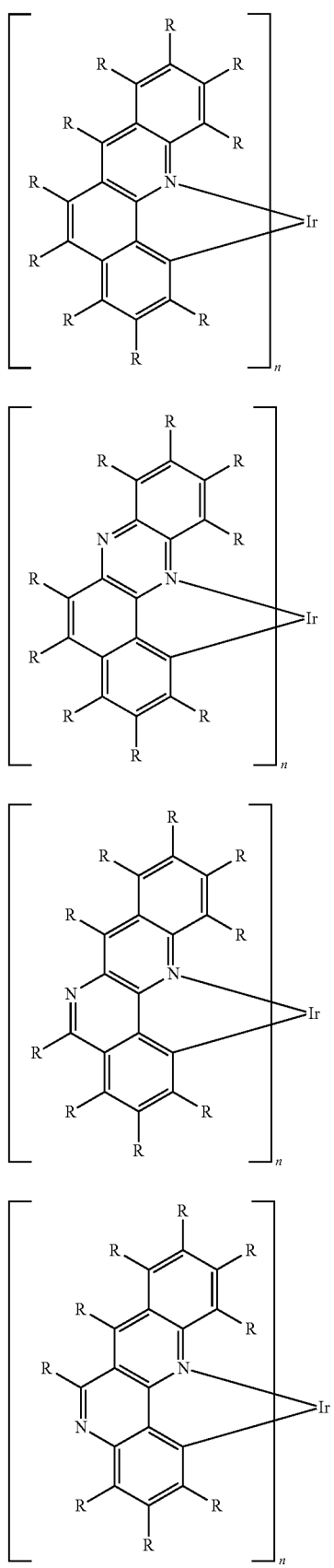
Formula (7-1)
Formula (7-2)
Formula (7-3)
Formula (7-4)

Formula (7-5)
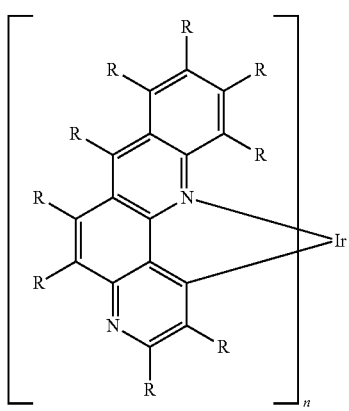
Formula (7-6)
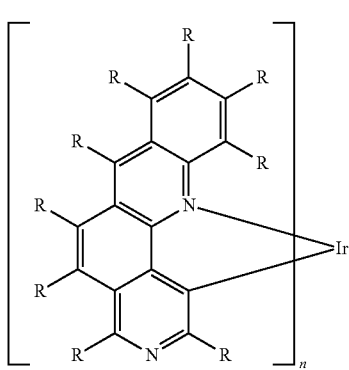
Formula (8-1)
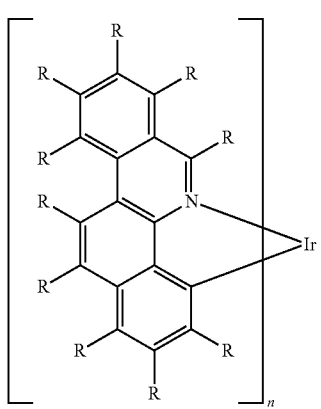
Formula (8-2)
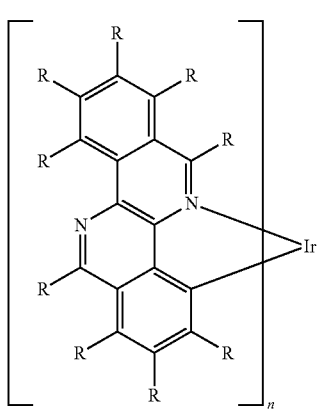
Formula (8-3)
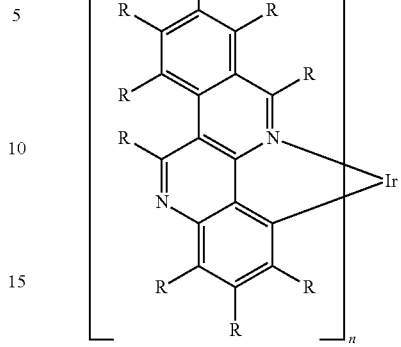
Formula (8-4)
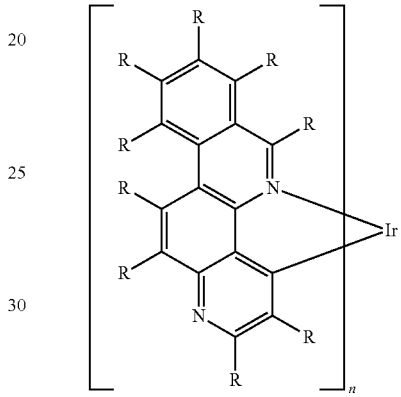
Formula (8-5)
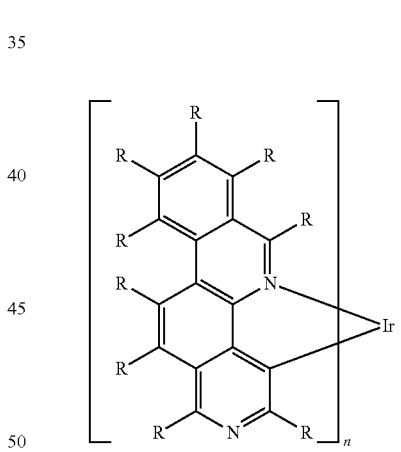
Formula (9-1)
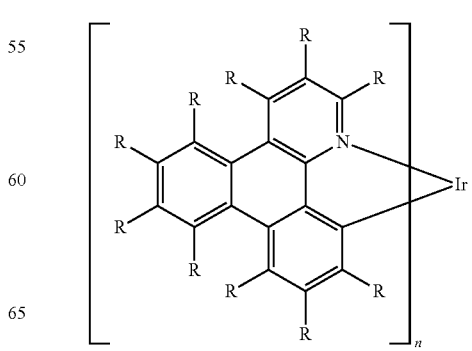

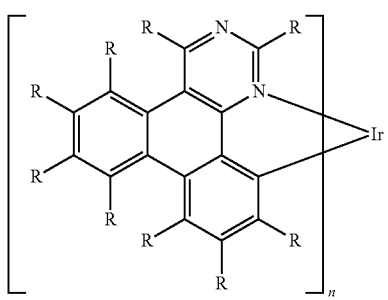
Formula (9-2)
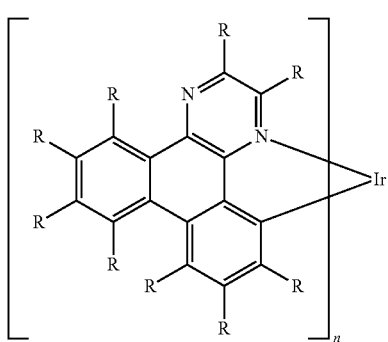
Formula (9-3)
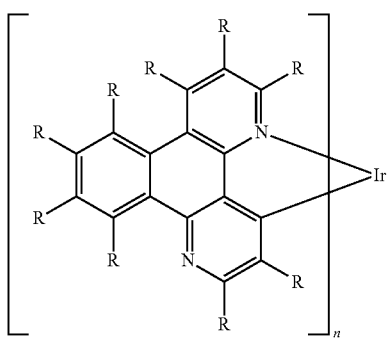
Formula (9-4)
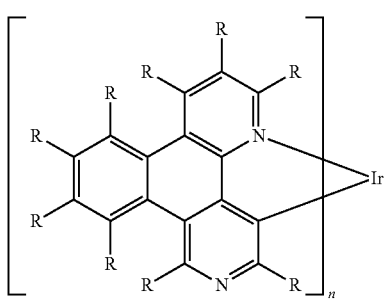
Formula (9-5)
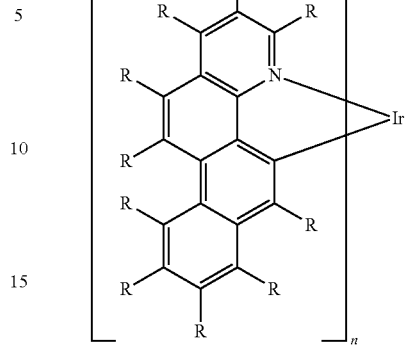
Formula (10-1)
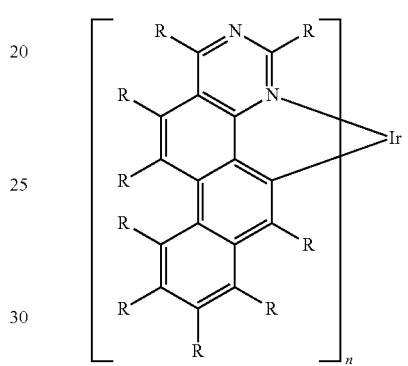
Formula (10-2)
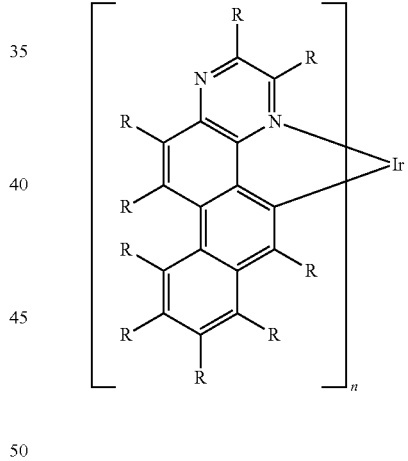
Formula (10-3)
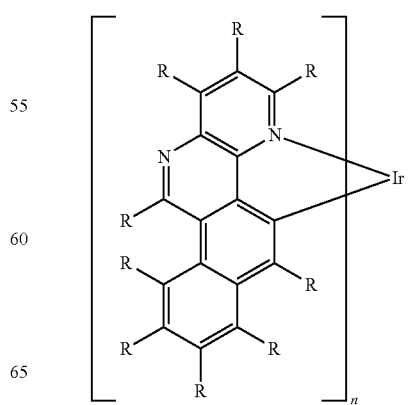
Formula (10-4)

Formula (10-5)
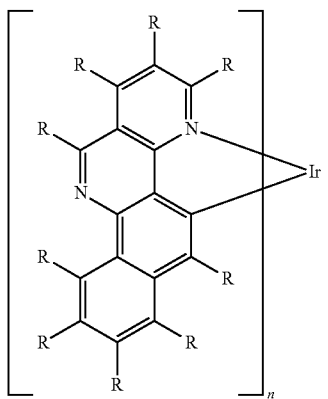
Formula (11-1)
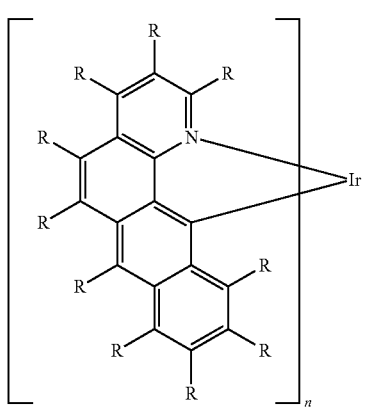
Formula (11-2)
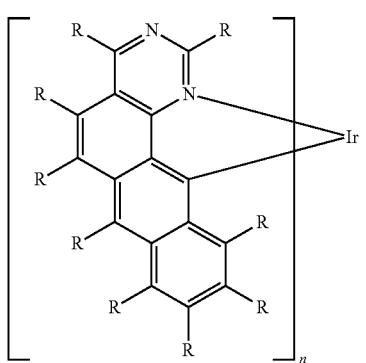
Formula (11-3)
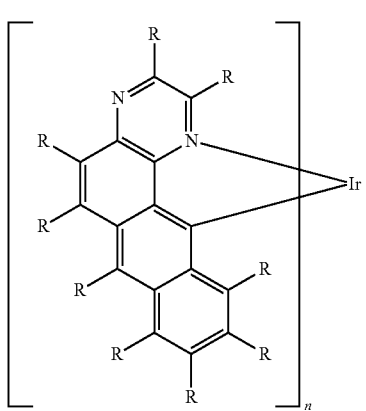
Formula (11-4)
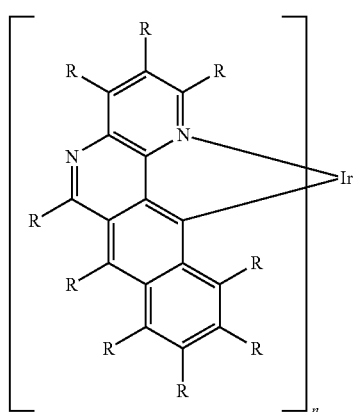
Formula (11-5)
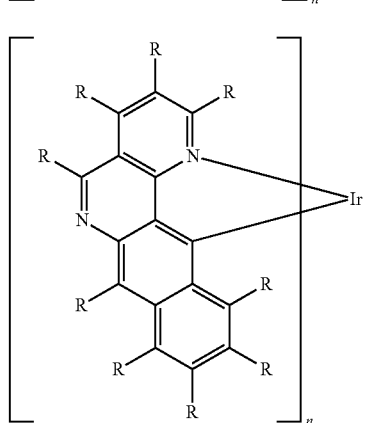
Formula (11-6)
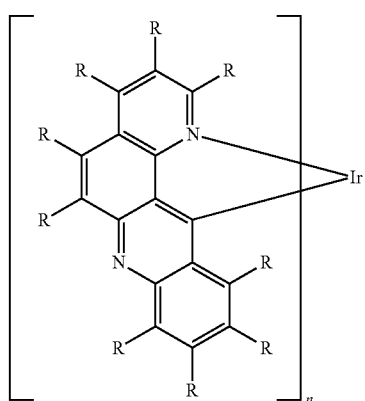
Formula (12-1)
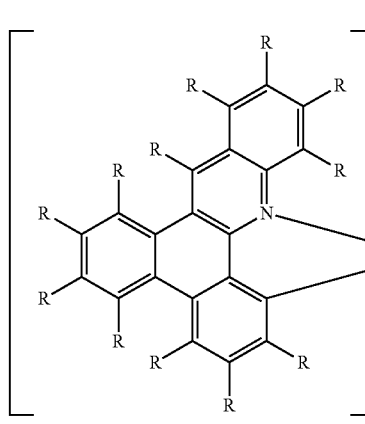

Formula (12-2)
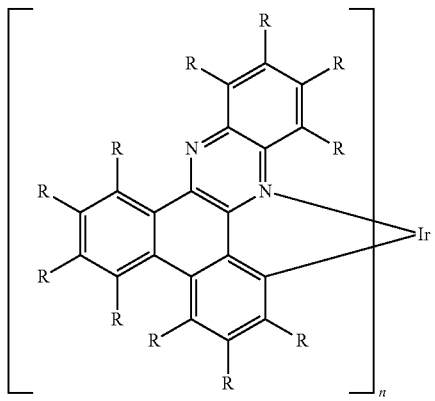
Formula (12-3)
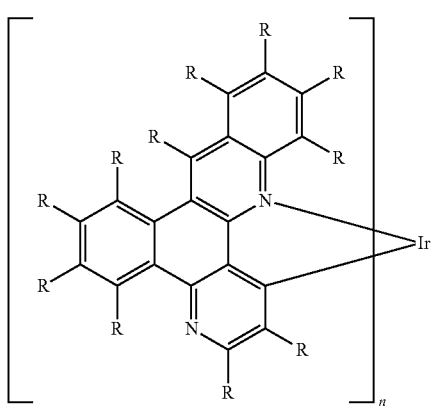
Formula (12-4)
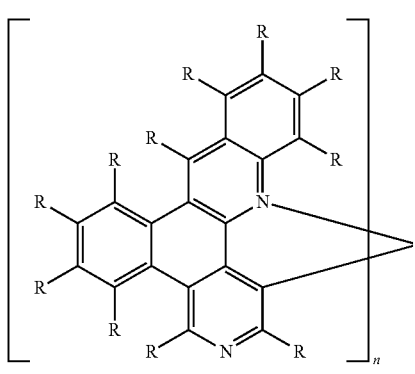
Formula (13-1)
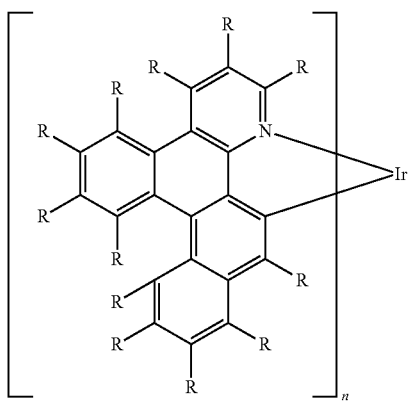
Formula (13-2)
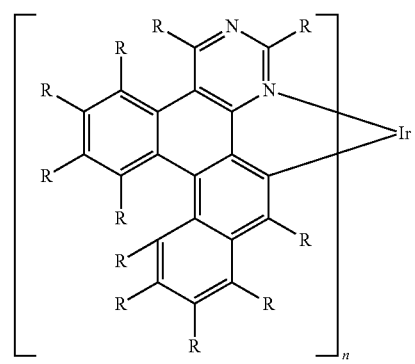
Formula (13-3)
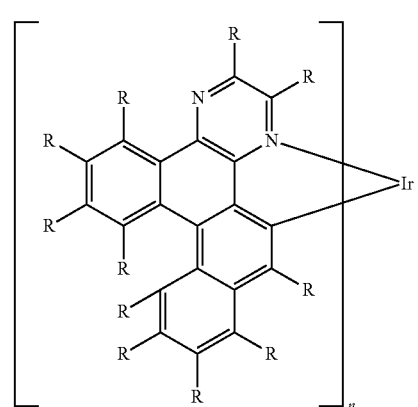
Formula (14-1)
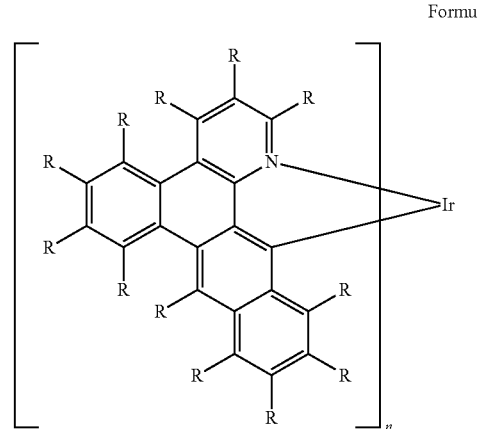
Formula (14-2)
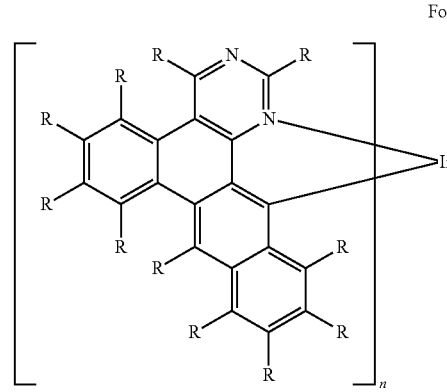

Formula (14-3)

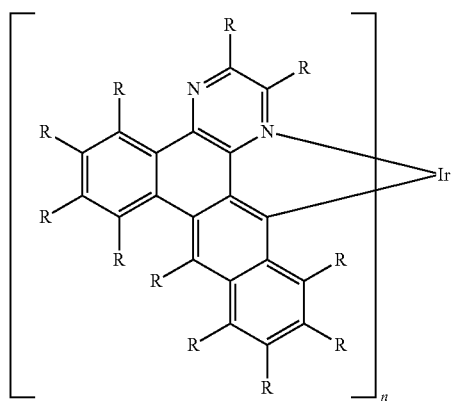

Formula (14-4)

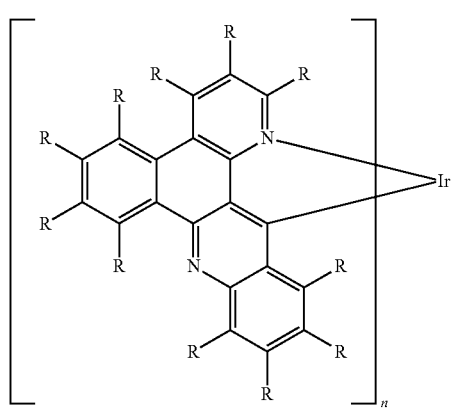

Formula (15-1)

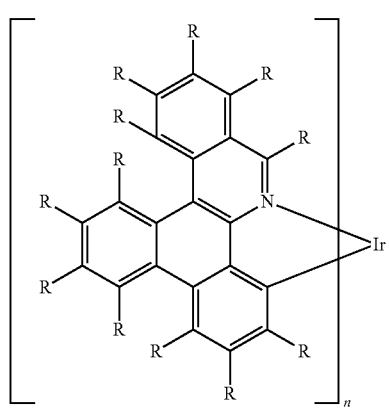

Formula (15-2)

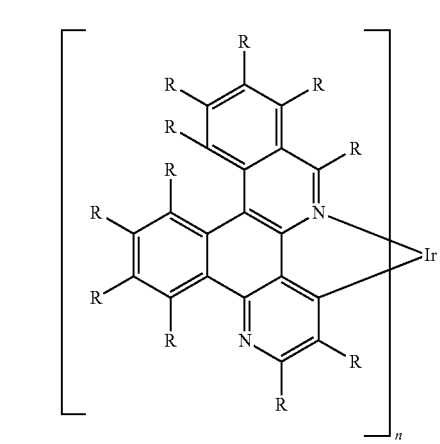

Formula (15-3)

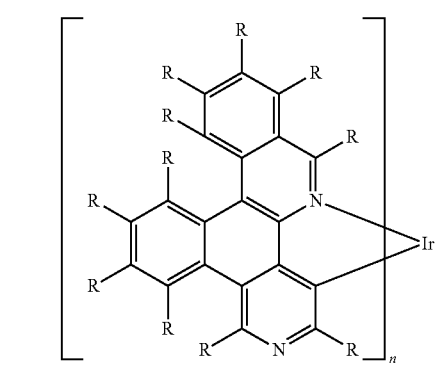

where the symbols and indices used have the definitions given above,

In one embodiment of the invention, it is preferable, if one of the atoms Y or, if present, X is N, when a substituent bonded adjacent to this nitrogen atom is an R group which is not hydrogen or deuterium.

In this case, this substituent R is preferably a group selected from $CF_3$, $OCF_3$, alkyl or alkoxy groups having 1 to 10 carbon atoms, especially branched or cyclic alkyl or alkoxy groups having 3 to 10 carbon atoms, a dialkylamino group having 2 to 10 carbon atoms, aromatic or heteroaromatic ring systems which may be substituted by one or more substituents $R^1$, or aralkyl or heteroaralkyl groups which may be substituted by one or more substituents $R^1$. These groups are sterically demanding groups. Further preferably, this R radical may also form a cycle with an adjacent R radical. In that case, the structures are preferably those of the formula (4) or (5), as present in accordance with the invention in the compounds of the present invention.

When the R radical adjacent to a nitrogen atom is an alkyl group, this alkyl group preferably has 3 to 10 carbon atoms. Preference is further given to a secondary or tertiary alkyl group in which the secondary or tertiary carbon atom is either bonded to the ligand directly or bonded to the ligand via a $CH_2$ group. More preferably, this alkyl group is selected from the structures of the following formulae (R-1) to (R-33), where the linkage of these groups to the ligand is also drawn in in each case:

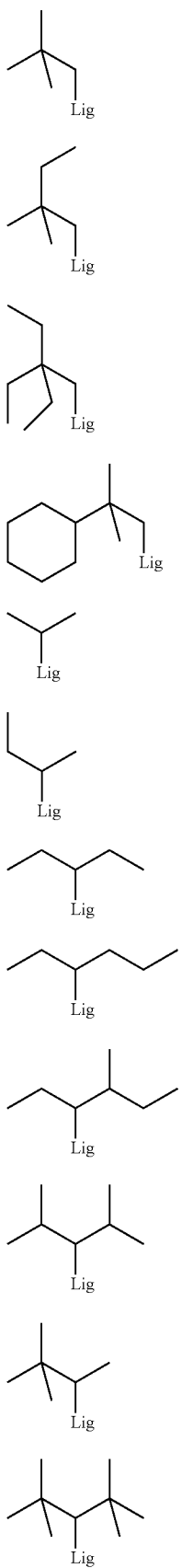
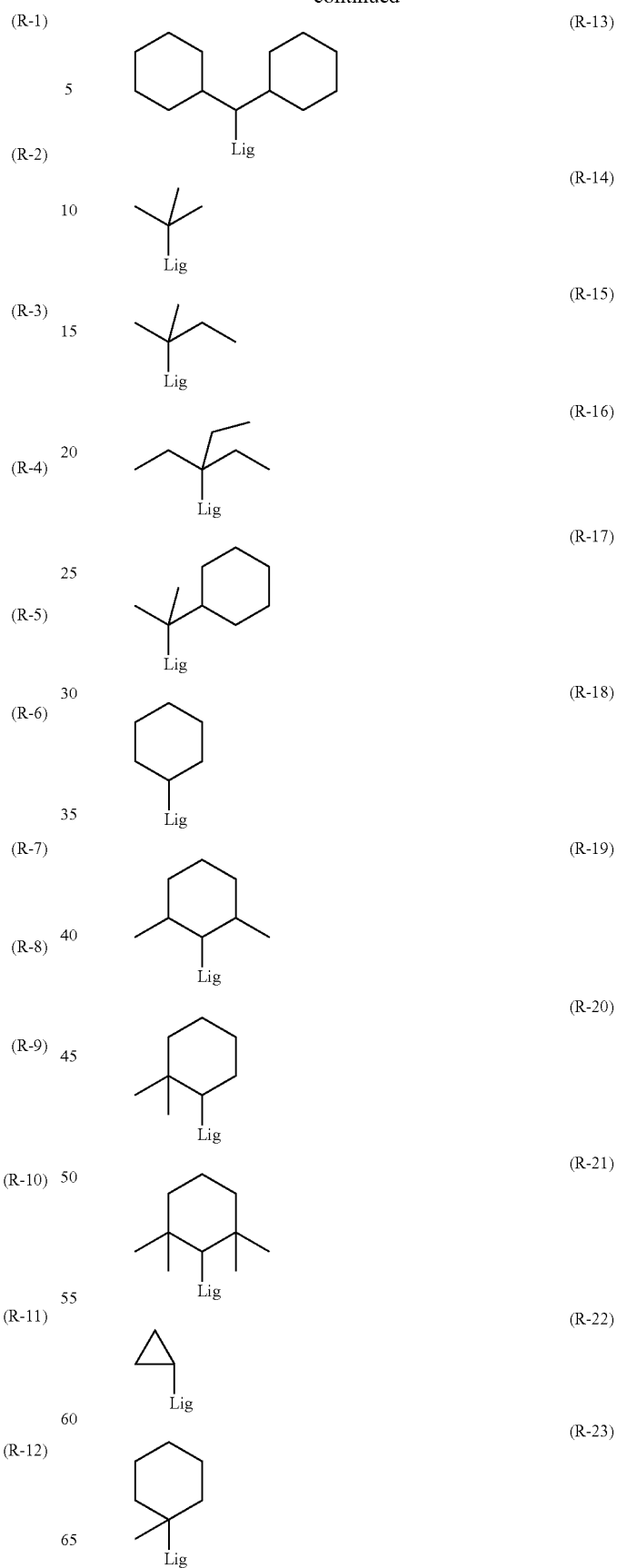

-continued

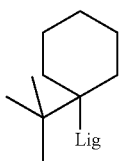 (R-24)

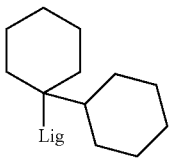 (R-25)

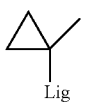 (R-26)

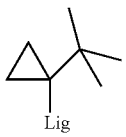 (R-27)

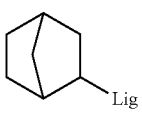 (R-28)

 (R-29)

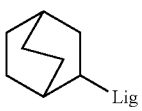 (R-30)

 (R-31)

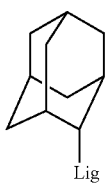 (R-32)

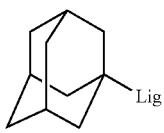 (R-33)

where Lig indicates the linkage of the alkyl group to the ligand.

When the R radical adjacent to a nitrogen atom is an alkoxy group, this alkoxy group preferably has 3 to 10 carbon atoms. This alkoxy group is preferably selected from the structures of the following formulae (R-34) to (R-47), where the linkage of these groups to the ligand is also drawn in in each case:

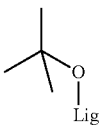 (R-34)

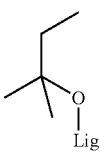 (R-35)

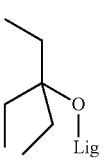 (R-36)

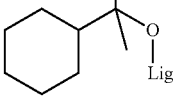 (R-37)

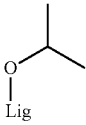 (R-38)

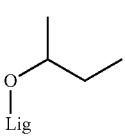 (R-39)

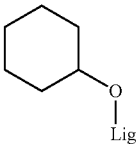 (R-40)

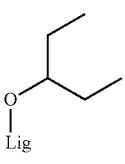 (R$^1$-41)

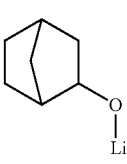 (R$^1$-42)

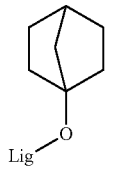 (R¹-43)

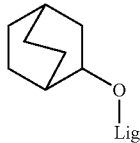 (R¹-44)

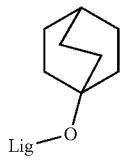 (R¹-45)

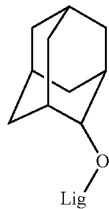 (R¹-46)

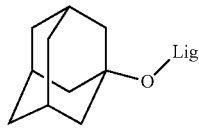 (R¹-47)

where Lig indicates the linkage of the alkoxy group to the ligand.

When the R radical adjacent to a nitrogen atom is a dialkylamino group, each of these alkyl groups preferably has 1 to 8 carbon atoms, more preferably 1 to 6 carbon atoms. Examples of suitable alkyl groups are methyl, ethyl or the structures shown above as groups (R-1) to (R-33). More preferably, the dialkylamino group is selected from the structures of the following formulae (R-48) to (R-55), where the linkage of these groups to the ligand is also drawn in in each case:

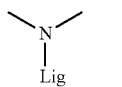 (R-48)

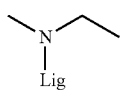 (R-49)

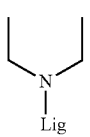 (R-50)

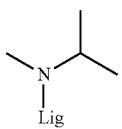 (R-51)

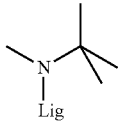 (R-52)

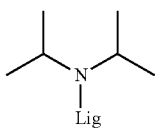 (R-53)

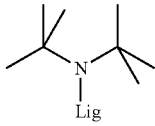 (R-54)

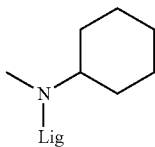 (R-55)

where Lig indicates the linkage of the dialkylamino group to the ligand.

When the R radical adjacent to a nitrogen atom is an aralkyl group, this aralkyl group is preferably selected from the structures of the following formulae (R-56) to (R-69), where the linkage of these groups to the ligand is also drawn in in each case:

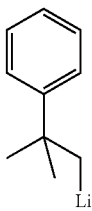 (R-56)

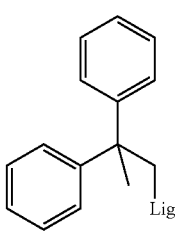 (R-57)

(R-58) 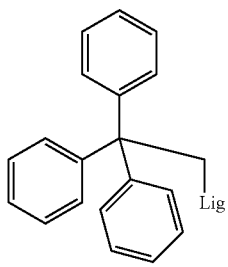

(R-59) 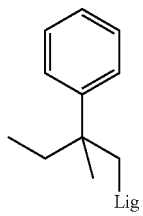

(R-60) 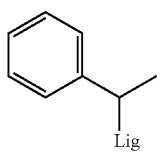

(R-61) 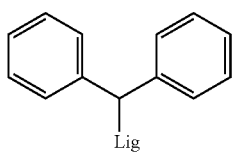

(R-62) 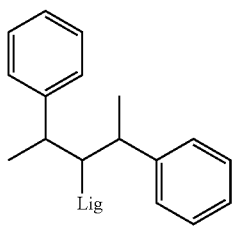

(R-63) 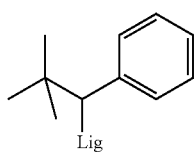

(R-64) 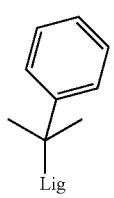

(R-65) 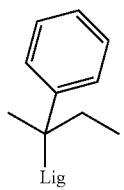

(R-66) 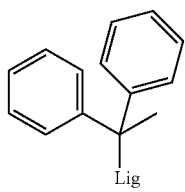

(R-67) 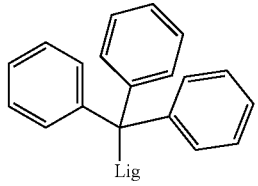

(R-68) 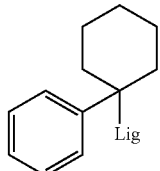

(R-69) 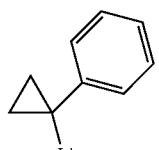

where Lig indicates the linkage of the aralkyl group to the ligand and the phenyl groups may each be substituted by one or more $R^1$ radicals.

When the R radical adjacent to a nitrogen atom is an aromatic or heteroaromatic ring system, this aromatic or heteroaromatic ring system preferably has 5 to 30 aromatic ring atoms, more preferably 5 to 24 aromatic ring atoms. In addition, this aromatic or heteroaromatic ring system preferably does not contain any aryl or heteroaryl groups in which more than two aromatic six-membered rings are fused directly to one another. More preferably, the aromatic or heteroaromatic ring system does not contain any fused aryl or heteroaryl groups at all, and most preferably contains only phenyl groups. In this case, the aromatic ring system is preferably selected from the structures of the following formulae (R-70) to (R-84), where the linkage of these groups to the ligand is also drawn in in each case:

(R-70) 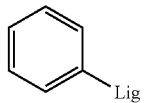

(R-71) 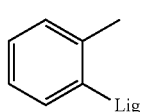

(R-72) 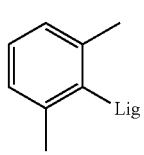

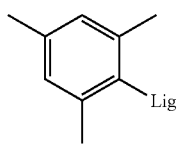 (R-73)
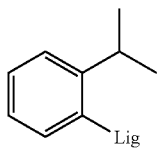 (R-74)
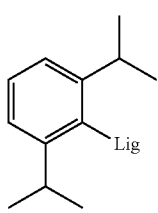 (R-75)
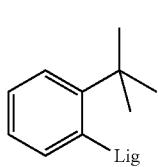 (R-76)
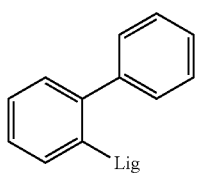 (R-77)
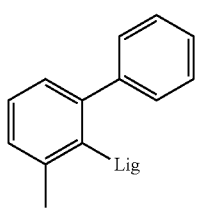 (R-78)
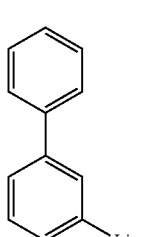 (R-79)
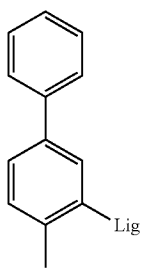 (R-80)
 (R-81)
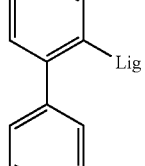 
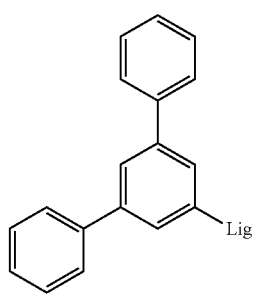 (R-82)
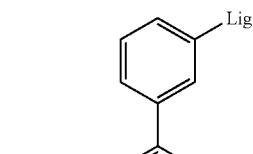 (R-83)
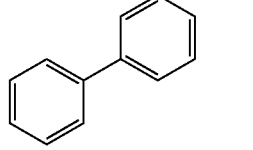
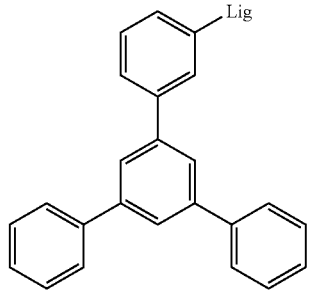 (R-84)
where Lig indicates the linkage of the aromatic ring system to the ligand and the phenyl groups may each be substituted by one or more $R^1$ radicals.
In addition, the heteroaromatic ring system is preferably selected from the structures of the following formulae (R-85) to (R-123), where the linkage of these groups to the ligand is also drawn in in each case:

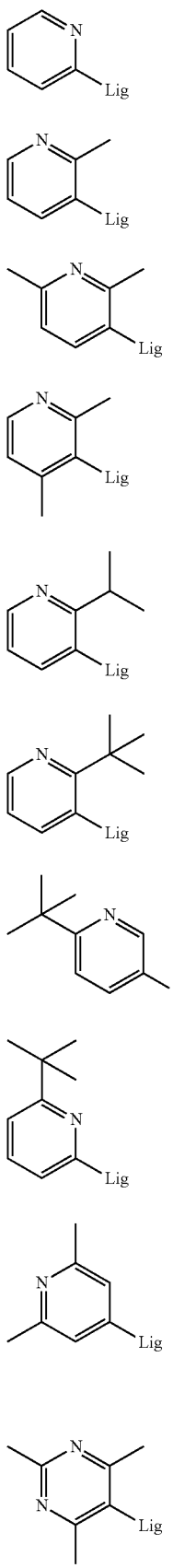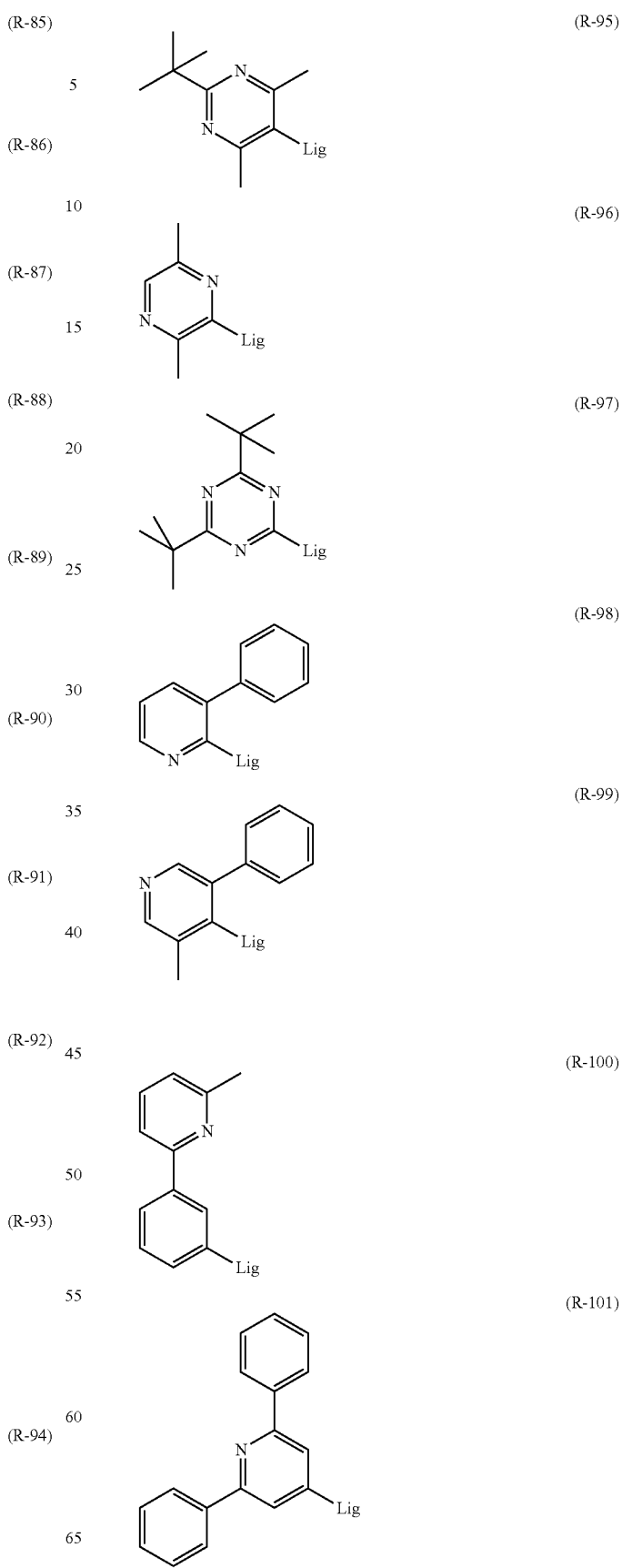

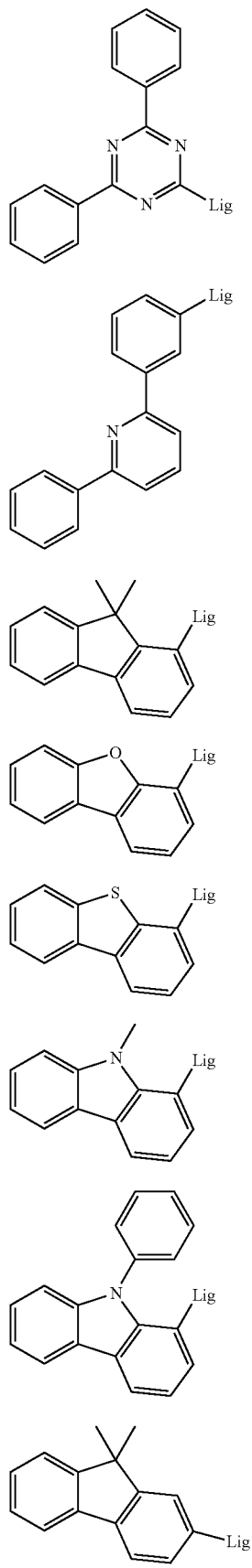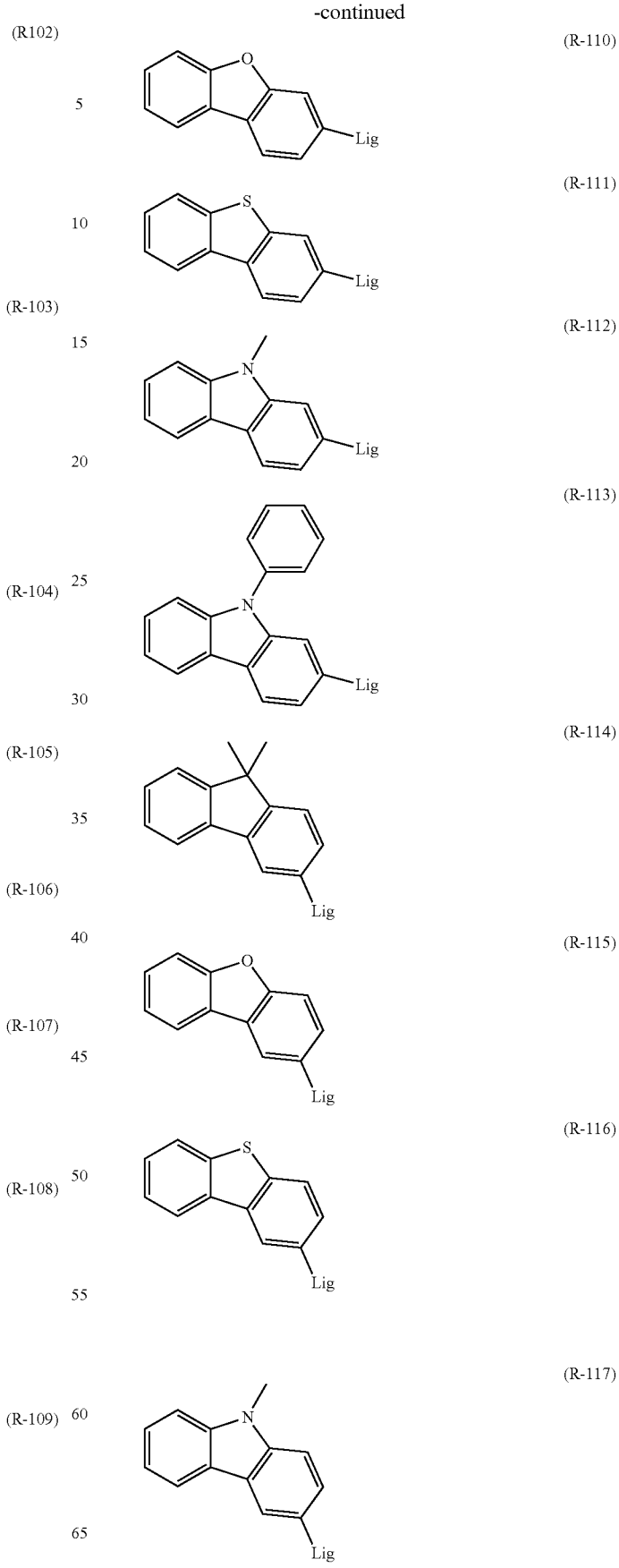

-continued (R-118) 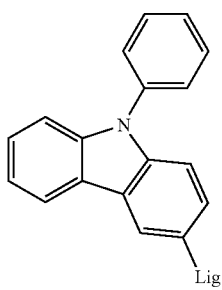

(R-119) 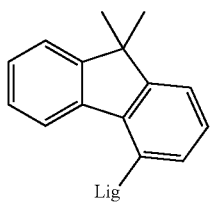

(R-120) 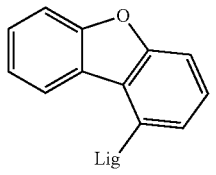

(R-121) 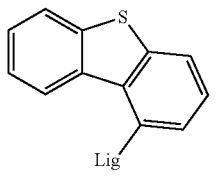

(R-122) 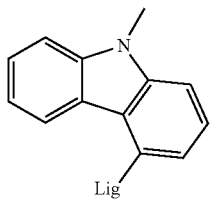

(R-123) 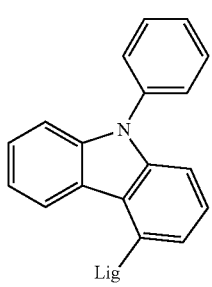

where Lig indicates the linkage of the heteroaromatic ring system to the ligand and the aromatic and heteroaromatic groups may each be substituted by one or more $R^1$ radicals.

The characterizing feature of the present invention is, as described above, that two adjacent Y groups and/or, if present, two adjacent X groups in the substructure of the formula (2) are CR and the respective R radicals together with the carbon atoms form a ring of the formula (4) or formula (5).

The groups of the formula (4) or (5) may be present in any position in the substructure of the formula (2) in which two Y groups or, if present, two X groups are bonded directly to one another. Preferred positions in which a group of the formula (4) or (5) is present are the substructures of the following formulae (6a) to (15h):

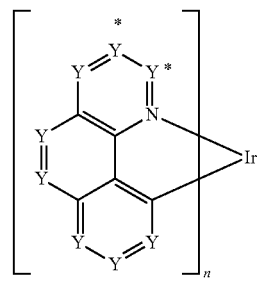

Formula (6a)

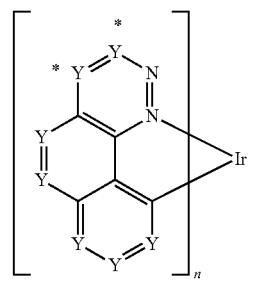

Formula (6b)

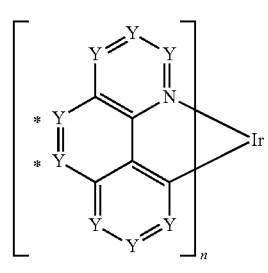

Formula (6c)

Formula (6d)

Formula (6e)

Formula (7a)
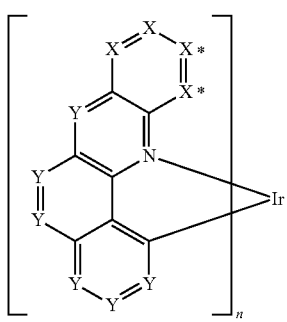
Formula (7b)
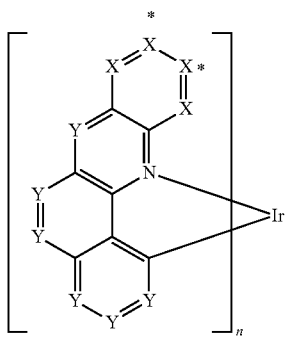
Formula (7c)
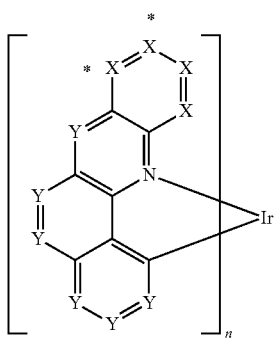
Formula (7d)
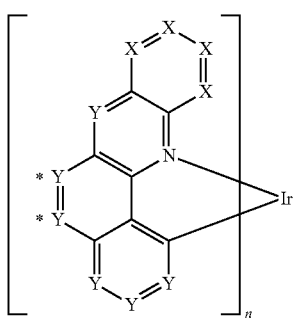
Formula (7e)
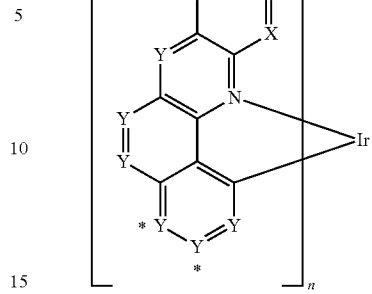
Formula (7f)
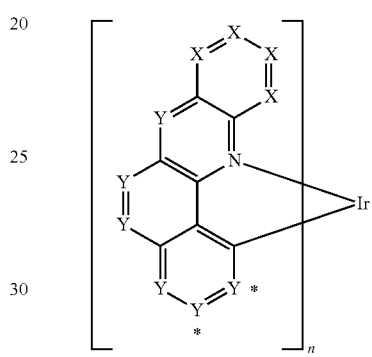
Formula (8a)
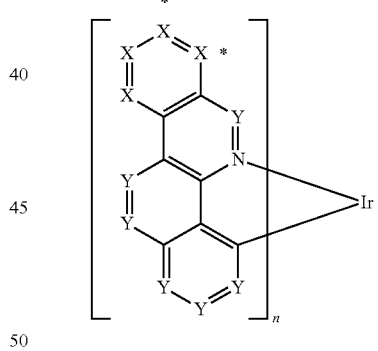
Formula (8b)
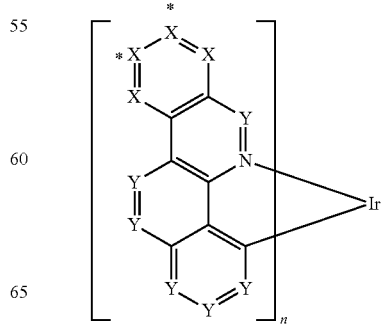

-continued
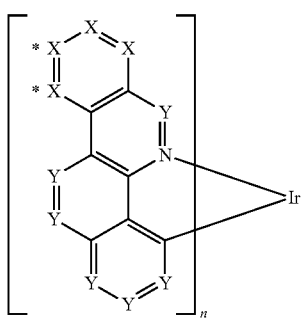
Formula (8c)
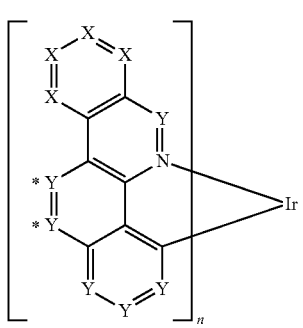
Formula (8d)
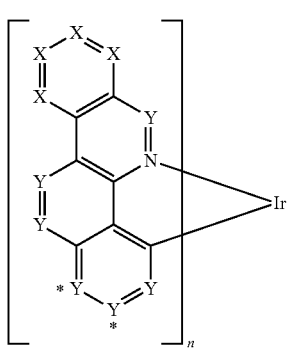
Formula (8e)
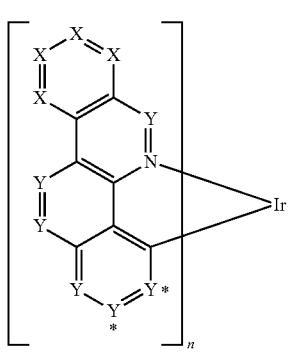
Formula (8f)
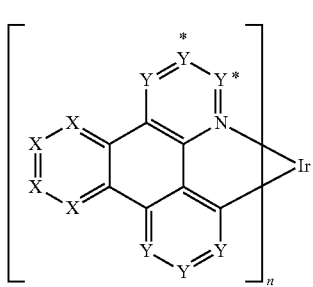
Formula (9a)
-continued
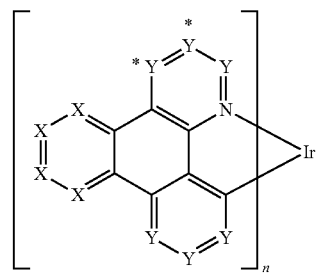
Formula (9b)
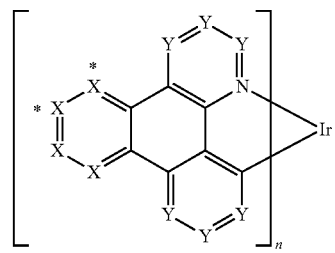
Formula (9c)
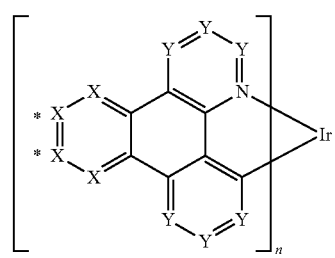
Formula (9d)
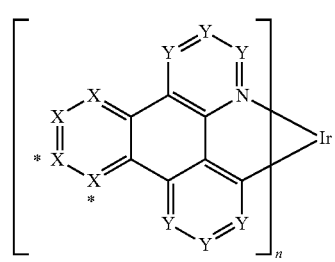
Formula (9e)
Formula (9f)
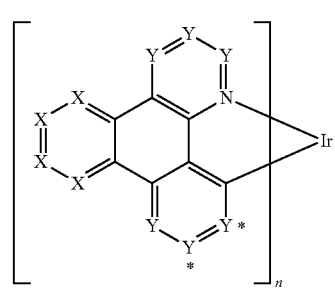
Formula (9g)

Formula (10a)
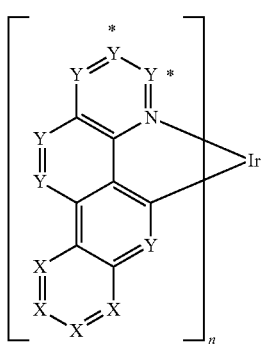
Formula (10b)
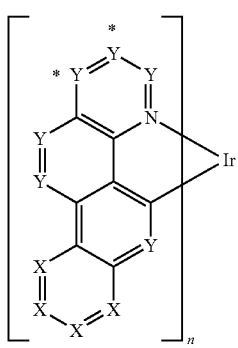
Formula (10c)
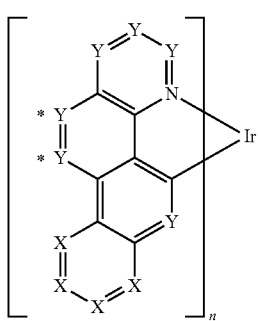
Formula (10d)
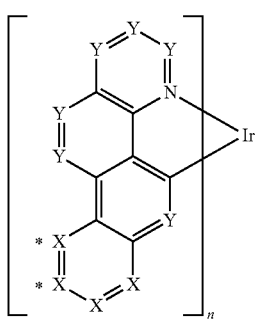
Formula (10e)
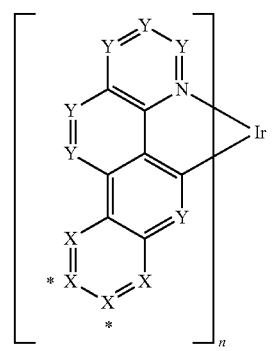
Formula (10f)
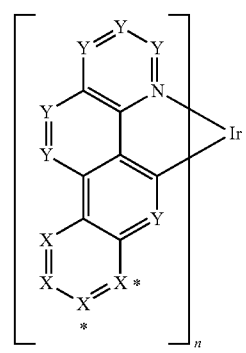
Formula (11a)
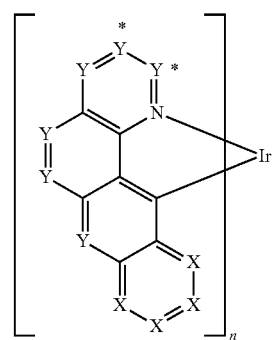
Formula (11b)
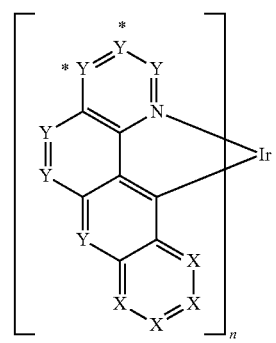

Formula (11c)
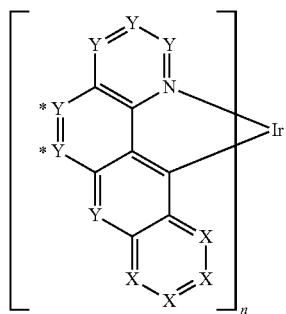
Formula (11d)
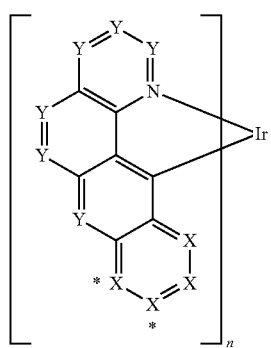
Formula (11e)
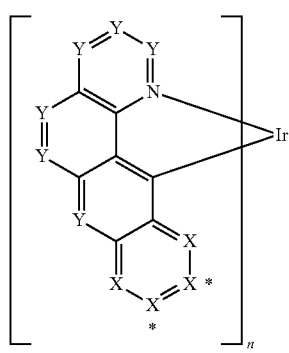
Formula (11f)
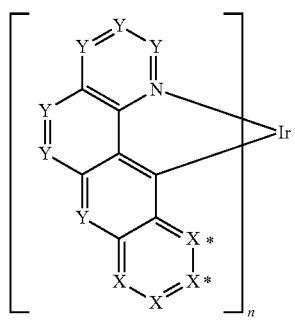
Formula (12a)
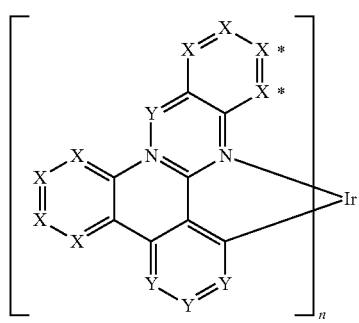
Formula (12b)
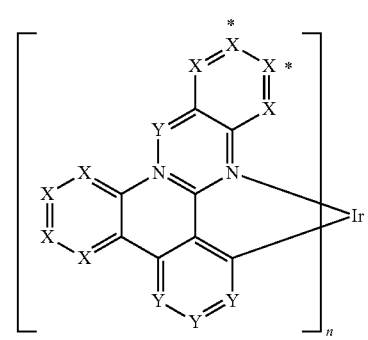
Formula (12c)
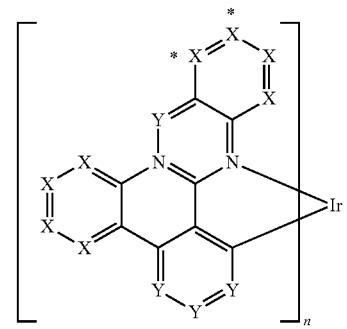
Formula (12d)
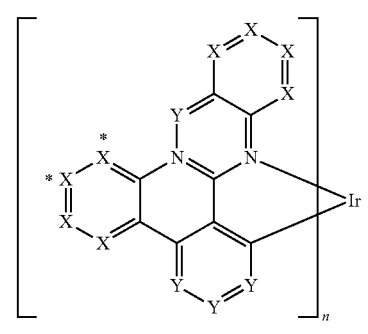
Formula (12e)
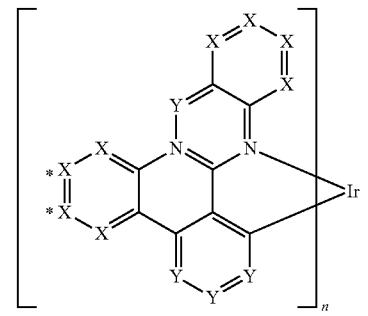
Formula (12f)
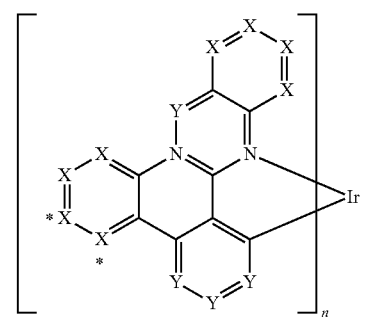

Formula (12g)
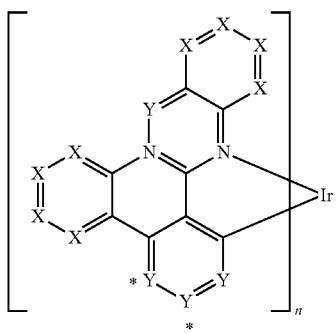
Formula (12h)
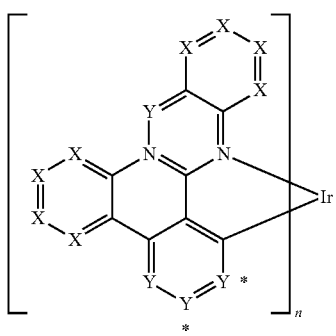
Formula (13a)
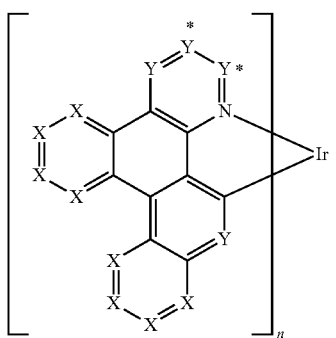
Formula (13b)
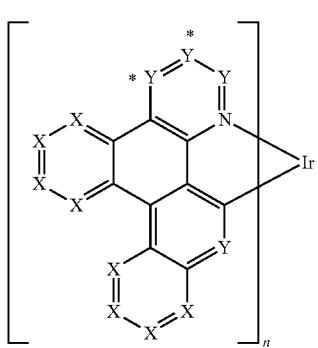
Formula (13c)
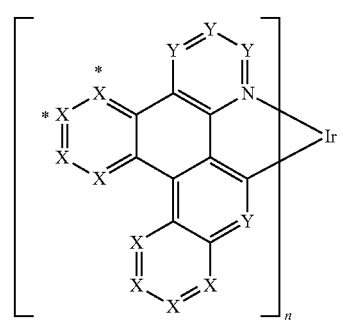
Formula (13d)
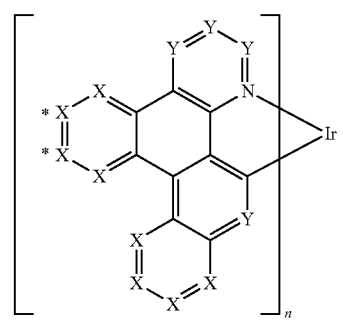
Formula (13e)
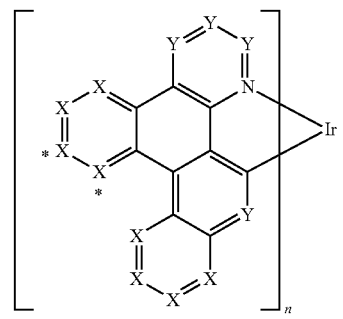
Formula (13f)
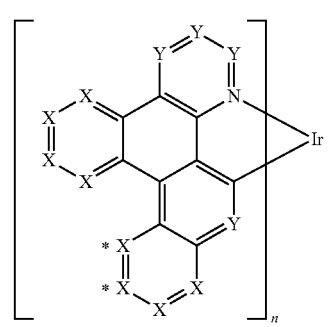
Formula (13g)

Formula (13h)
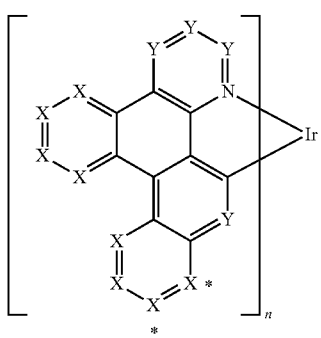
Formula (14a)
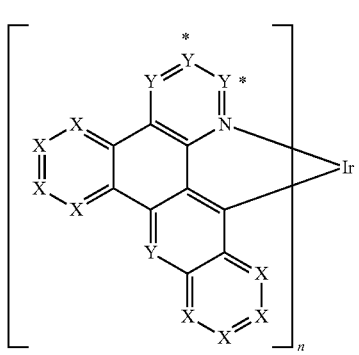
Formula (14b)
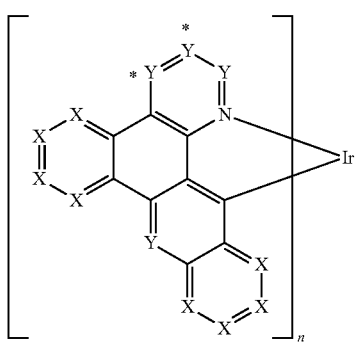
Formula (14c)
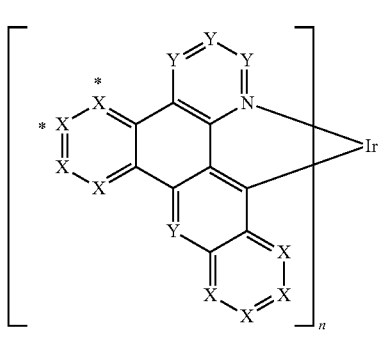
Formula (14d)
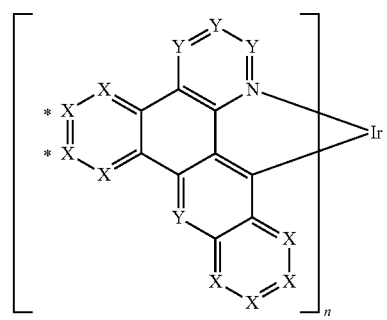
Formula (14e)
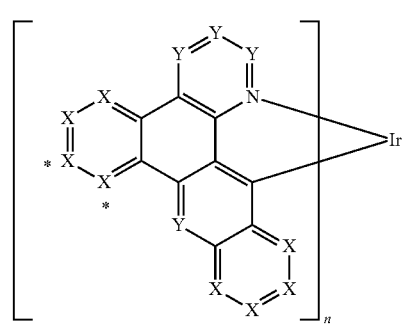
Formula (14f)
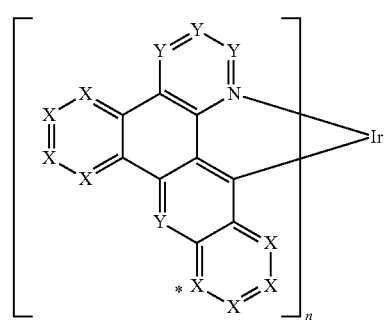
Formula (14g)
Formula (14h)
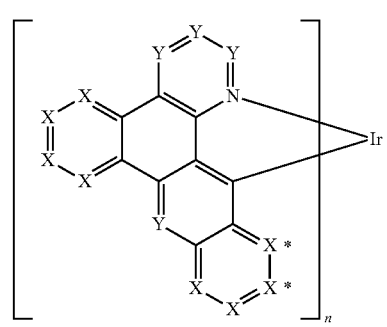

-continued

Formula (15a)
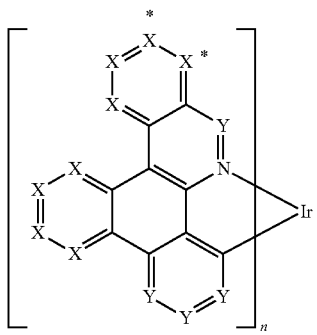

Formula (15b)
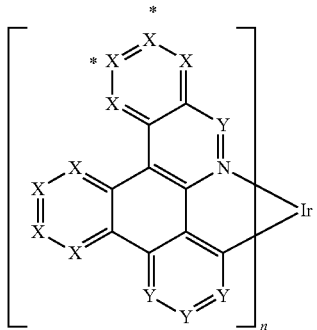

Formula (15c)
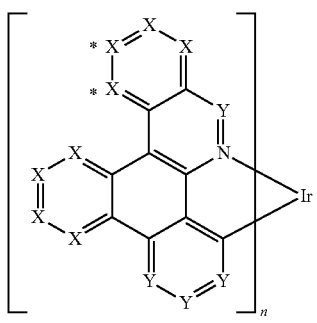

Formula (15d)
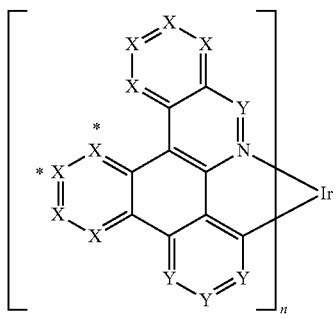

Formula (15e)
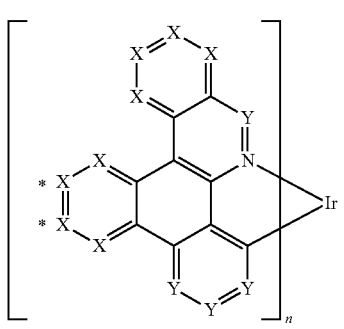

Formula (15f)
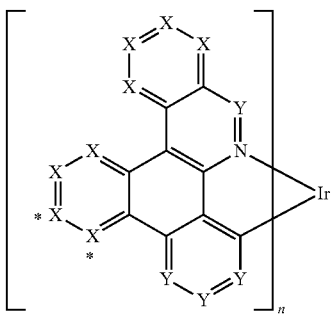

Formula (15g)
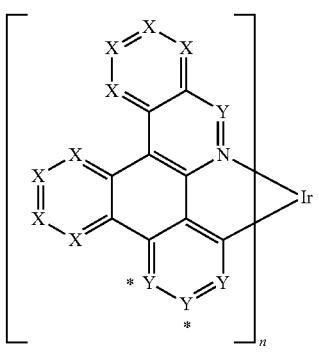

Formula (15h)

where the symbols and indices used are as defined above and * in each case indicates the position at which the two adjacent Y or X groups are CR and the respective R radicals together with the carbon atoms form a ring of the formula (4) or formula (5).

In the above-depicted structures of the formulae (4) and (5) and the further embodiments of these structures specified as preferred, a double bond is formed in a formal sense between the two carbon atoms. This is a simplification of the chemical structure since these two carbon atoms are incorporated into an aromatic or heteroaromatic system and hence the bond between these two carbon atoms is formally between the bonding level of a single bond and that of a double bond. The drawing of the formal double bond should thus not be interpreted so as to limit the structure; instead, it will be apparent to the person skilled in the art that this is an aromatic bond.

An essential feature in the groups of the formulae (4) and (5) is that they do not have any acidic benzylic protons. Benzylic protons are understood to mean protons which bind to a carbon atom bonded directly to the ligand.

The absence of acidic benzylic protons in formula (4) is achieved by virtue of $A^1$ and $A^3$, when they are $C(R^3)_2$, being defined such that $R^3$ is not hydrogen. The absence of acidic benzylic protons is achieved in formula (5) in that the structure is a bicyclic structure. Because of the rigid spatial arrangement, $R^1$, when it is H, is much less acidic than benzylic protons since the corresponding anion of the bicyclic structure is not mesomerically stabilized. Even when $R^1$ in formula (5) is H, this is therefore a non-acidic proton in the context of the present application.

In a preferred embodiment of the structure of formula (4), not more than one of the $A^1$, $A^2$ and $A^3$ groups is a heteroatom, especially O or $NR^3$, and the other two groups are $C(R^3)_2$ or $C(R^1)_2$, or $A^1$ and $A^3$ are the same or different at each instance and are O or $NR^3$ and $A^2$ is $C(R^1)_2$. In a particularly preferred embodiment of the invention, $A^1$ and $A^3$ are the same or different at each instance and are $C(R^3)_2$, and $A^2$ is $C(R^1)_2$ and more preferably $C(R^3)_2$. Preferred embodiments of the formula (4) are thus the structures of the formulae (4-A), (4-B), (4-C) and (4-D), and a particularly preferred embodiment of the formula (4-A) is the structure of the formula (4-E):

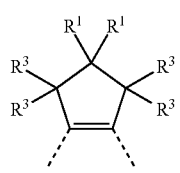
Formula (4-A)

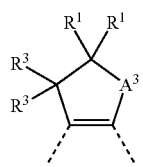
Formula (4-B)

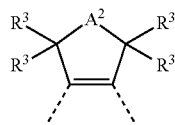
Formula (4-C)

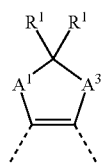
Formula (4-D)

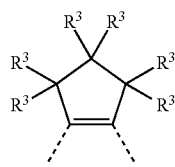
Formula (4-E)

where $R^1$ and $R^3$ are as defined above and $A^1$, $A^2$ and $A^3$ are the same or different at each instance and are O or $NR^3$.

In a preferred embodiment of the structure of formula (5), the $R^1$ radicals bonded to the bridgehead are H, D, F or $CH_3$. Further preferably, $A^2$ is $C(R^1)_2$ or O, and more preferably $C(R^3)_2$. Preferred embodiments of the formula (5) are thus structures of the formulae (5-A) and (5-B), and a particularly preferred embodiment of the formula (5-A) is a structure of the formula (5-C):

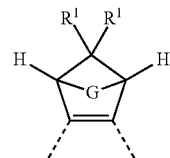
Formula (5-A)

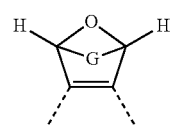
Formula (5-B)

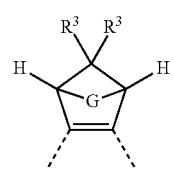
Formula (5-C)

where the symbols used are as defined above.

Further preferably, the G group in the formulae (5), (5-A), (5-B) and (5-C) is a 1,2-ethylene group which may be substituted by one or more $R^2$ radicals, where $R^2$ is preferably the same or different at each instance and is H or an alkyl group having 1 to 4 carbon atoms, or an ortho-arylene group which has 6 to 10 carbon atoms and may be substituted by one or more $R^2$ radicals, but is preferably unsubstituted, especially an ortho-phenylene group which may be substituted by one or more $R^2$ radicals, but is preferably unsubstituted.

In a further preferred embodiment of the invention, $R^3$ in the groups of the formulae (4) and (5) and in the preferred embodiments is the same or different at each instance and is F, a straight-chain alkyl group having 1 to 10 carbon atoms or a branched or cyclic alkyl group having 3 to 20 carbon atoms, where one or more nonadjacent $CH_2$ groups in each case may be replaced by $R^2C=CR^2$ and one or more hydrogen atoms may be replaced by D or F, or an aromatic or heteroaromatic ring system which has 5 to 14 aromatic ring atoms and may be substituted in each case by one or more $R^2$ radicals; at the same time, two $R^3$ radicals bonded to the same carbon atom may together form an aliphatic or aromatic ring system and thus form a spiro system; in addition, $R^3$ may form an aliphatic ring system with an adjacent R or $R^1$ radical.

In a particularly preferred embodiment of the invention, $R^3$ in the groups of the formulae (4) and (5) and in the preferred embodiments is the same or different at each instance and is F, a straight-chain alkyl group having 1 to 3 carbon atoms, especially methyl, or an aromatic or heteroaromatic ring system which has 5 to 12 aromatic ring atoms and may be substituted in each case by one or more $R^2$ radicals, but is preferably unsubstituted; at the same time, two $R^3$ radicals bonded to the same carbon atom may together form an aliphatic or aromatic ring system and thus form a spiro system; in addition, $R^3$ may form an aliphatic ring system with an adjacent R or $R^1$ radical.

Examples of particularly suitable groups of the formula (4) are the groups (4-1) to (4-69) listed below:

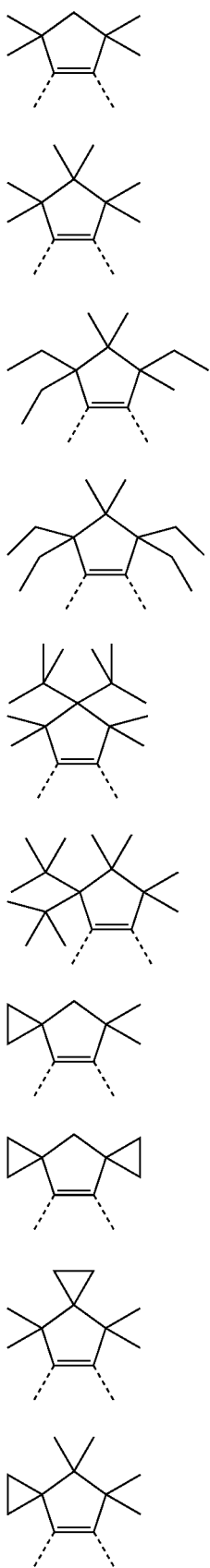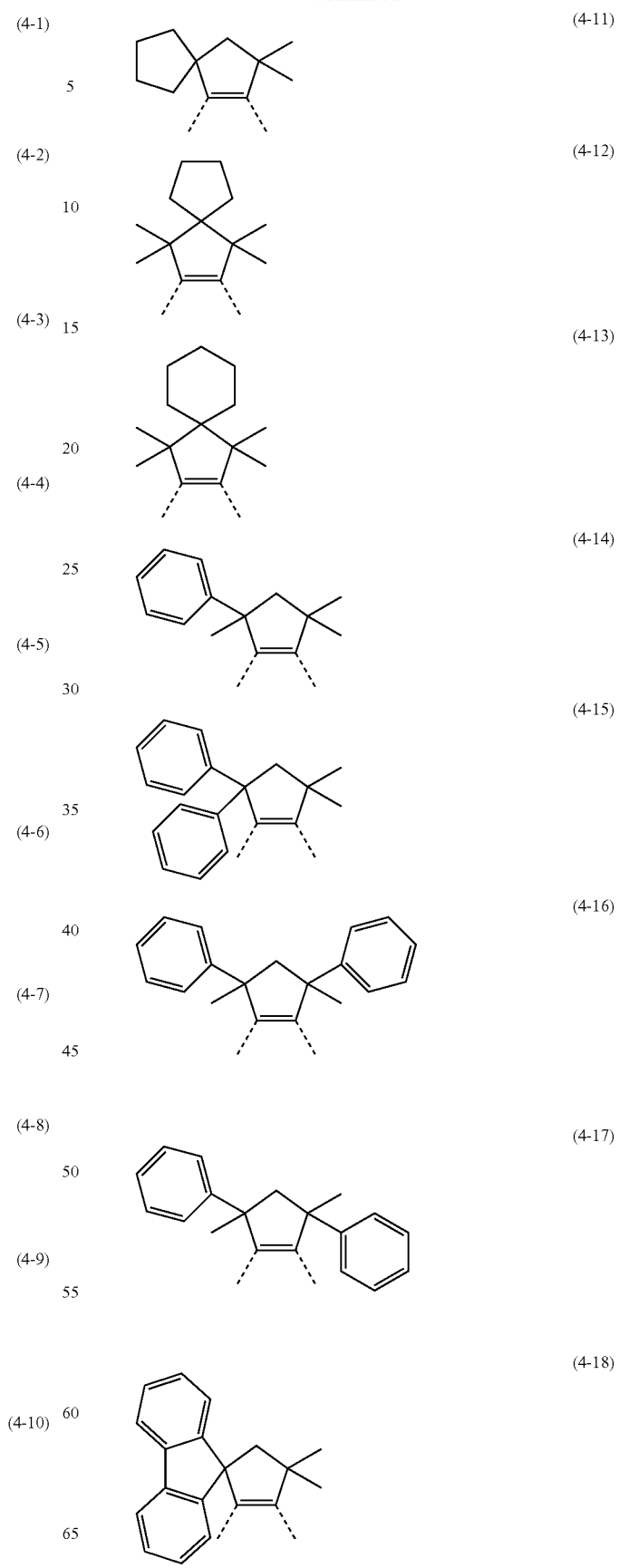

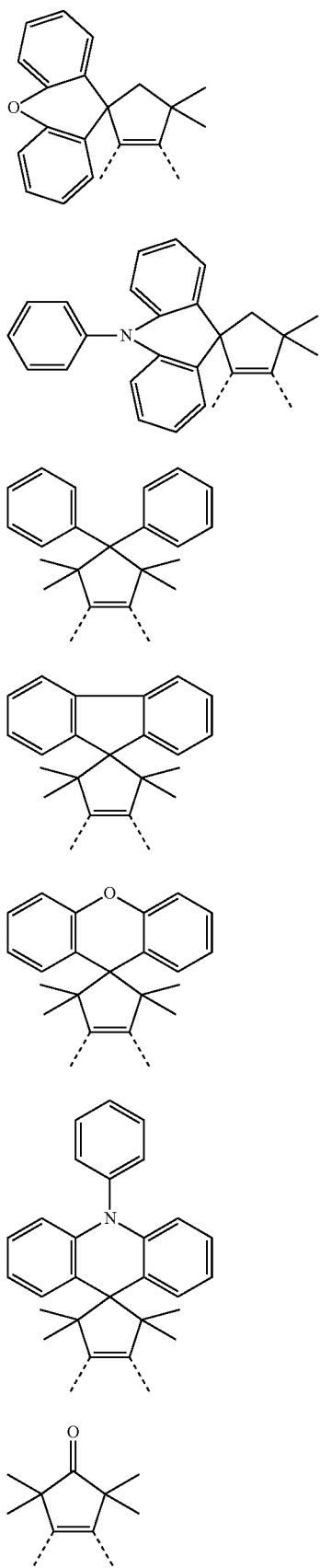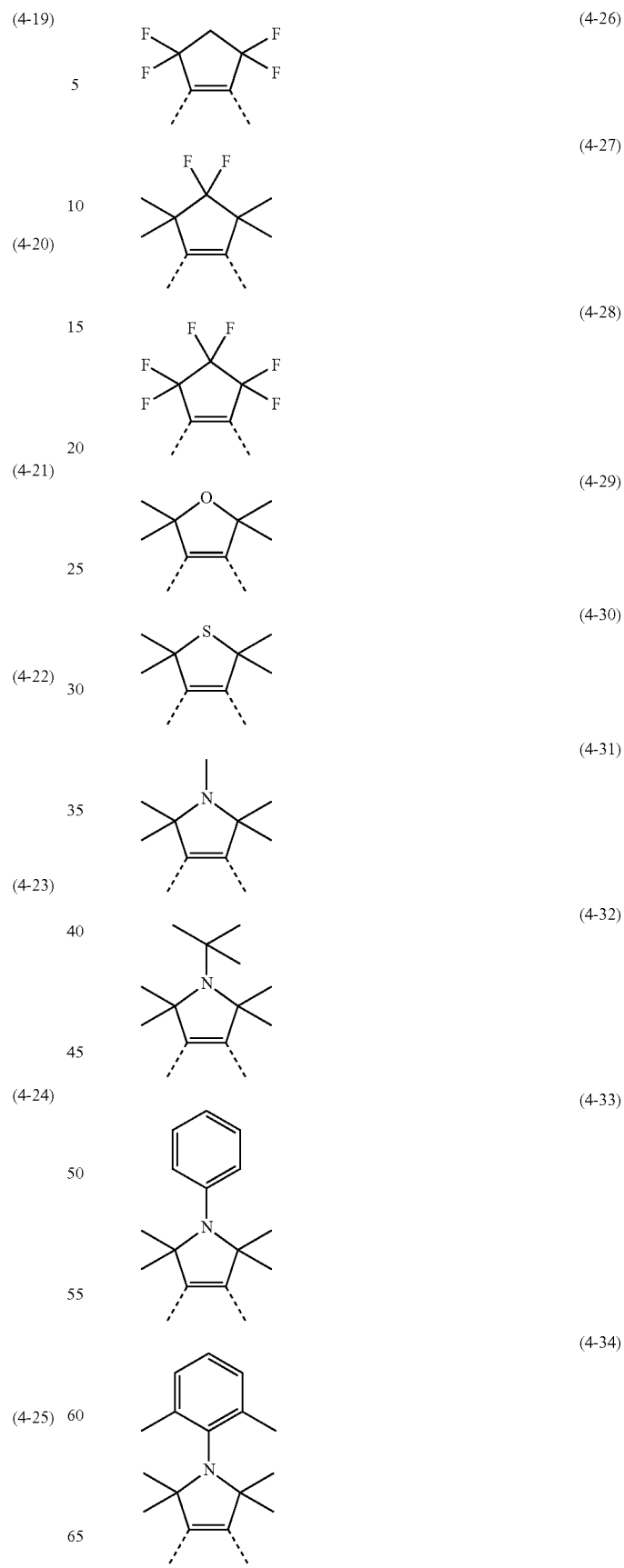

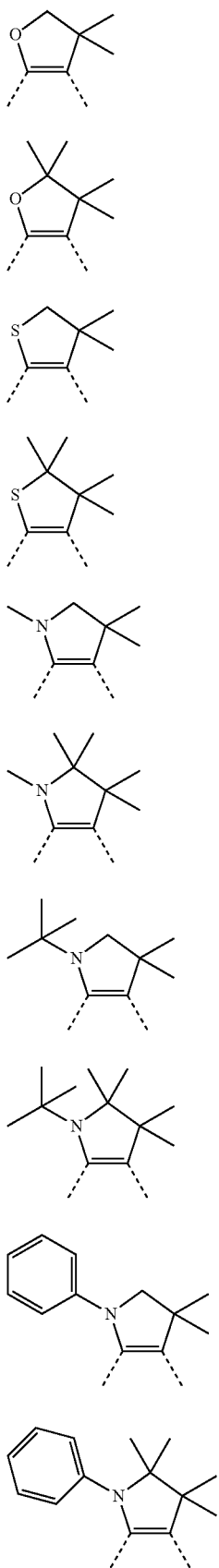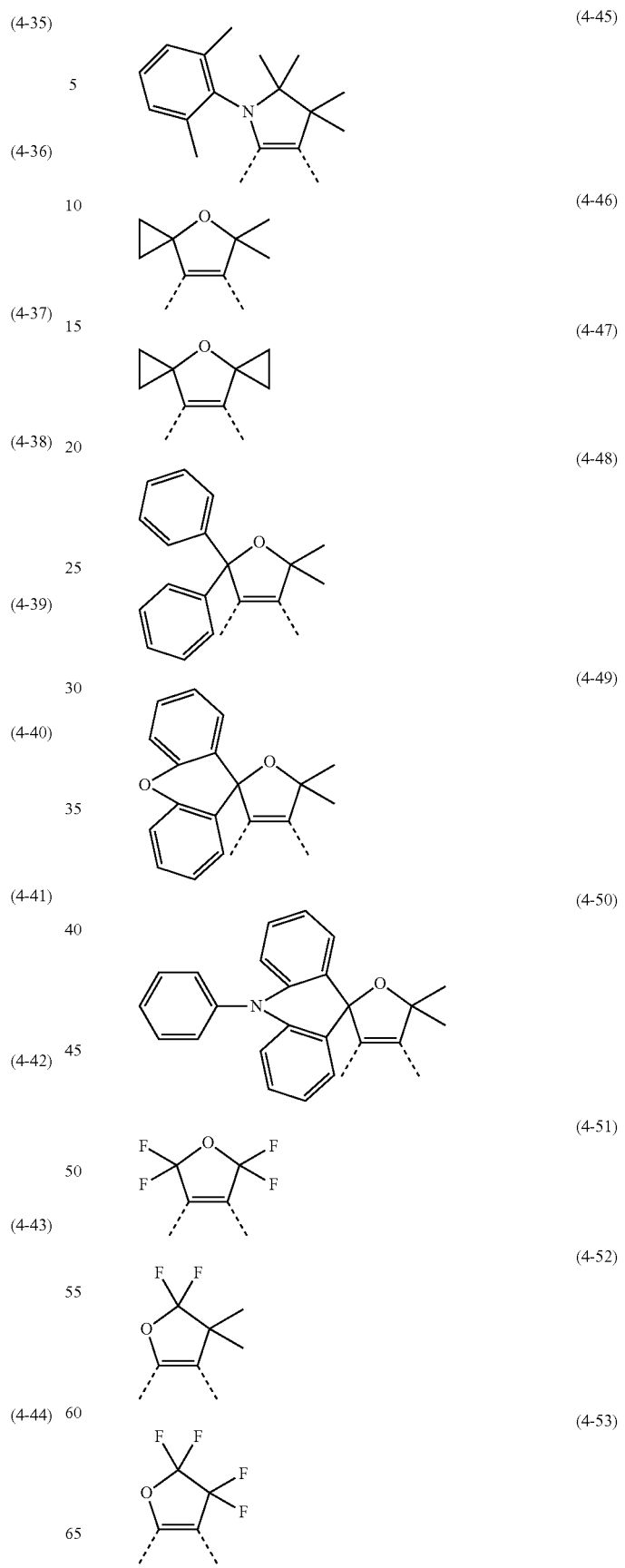

(4-54) 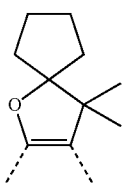
(4-55) 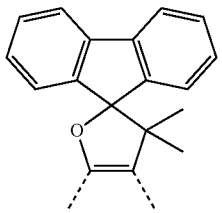
(4-56) 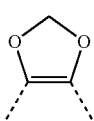
(4-57) 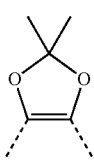
(4-58) 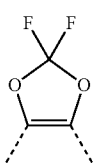
(4-59) 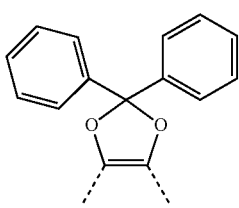
(4-60) 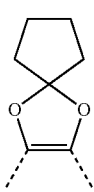
(4-61) 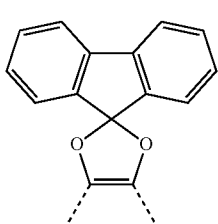
(4-62) 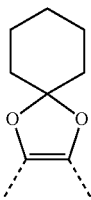
(4-63) 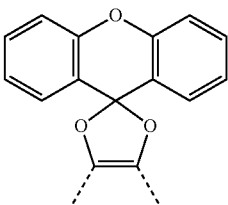
(4-64) 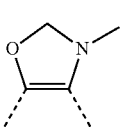
(4-65) 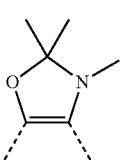
(4-66) 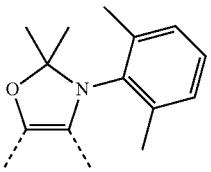
(4-67) 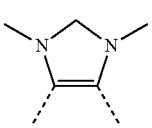
(4-68) 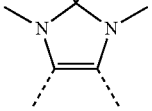
(4-69) 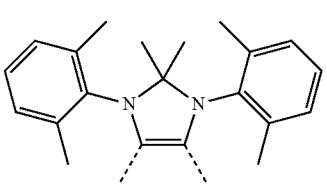
Examples of particularly suitable groups of the formula (5) are the groups (5-1) to (5-22) listed below:
(5-1) 

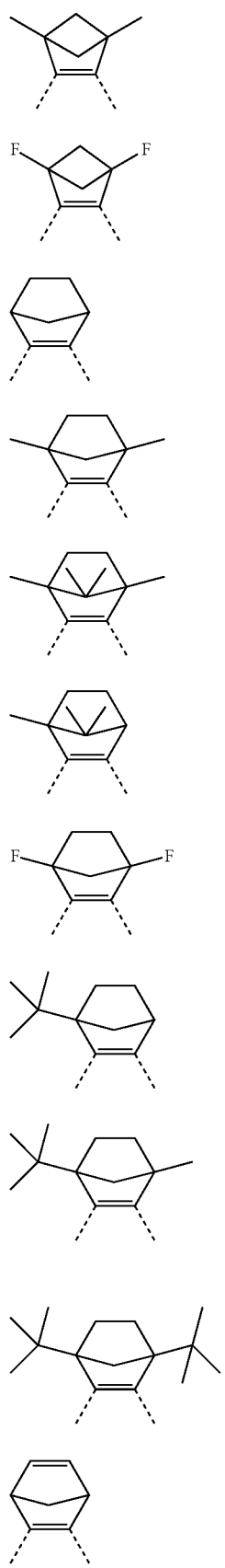
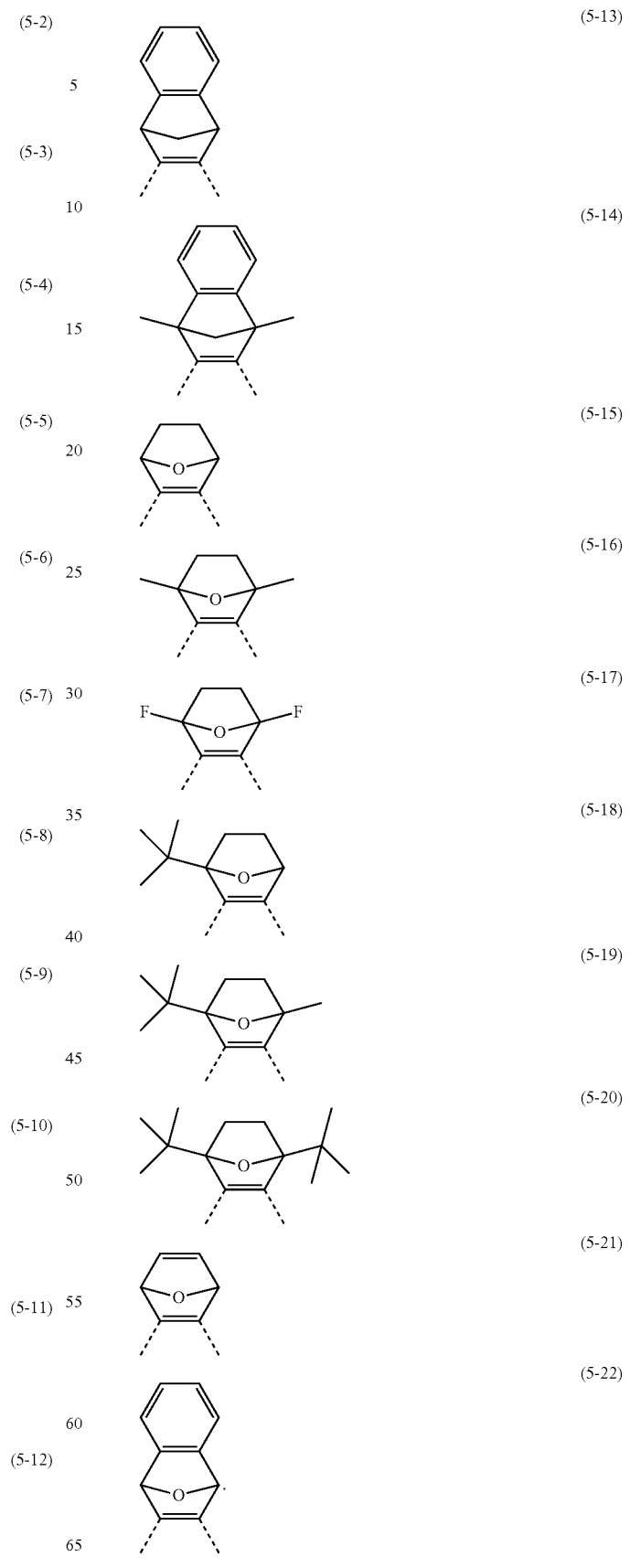

When still further or other R radicals are bonded within the substructure of the formula (2), these R radicals are the same or different at each instance and are preferably selected from the group consisting of H, D, F, N(R$^1$)$_2$, CN, Si(R$^1$)$_3$, C(=O)R$^1$, a straight-chain alkyl group having 1 to 10 carbon atoms or an alkenyl group having 2 to 10 carbon atoms or a branched or cyclic alkyl group having 3 to 10 carbon atoms, each of which may be substituted by one or more R$^1$ radicals, where one or more hydrogen atoms may be replaced by D or F, or an aromatic or heteroaromatic ring system which has 5 to 24 aromatic ring atoms and may be substituted in each case by one or more R$^1$ radicals; at the same time, two adjacent R radicals together or R together with R$^1$ may also form a mono- or polycyclic, aliphatic or aromatic ring system. More preferably, these R radicals are the same or different at each instance and are selected from the group consisting of H, D, F, a straight-chain alkyl group having 1 to 6 carbon atoms or a branched or cyclic alkyl group having 3 to 10 carbon atoms, where one or more hydrogen atoms may be replaced by F, or an aromatic or heteroaromatic ring system which has 5 to 18 aromatic ring atoms and may be substituted in each case by one or more R$^1$ radicals; at the same time, two adjacent R radicals together or R together with R$^1$ may also form a mono- or polycyclic, aliphatic or aromatic ring system. When the system is an aromatic or heteroaromatic ring system, it is preferable when the system does not contain more than two aromatic 6-membered rings fused directly to one another, and especially does not contain any aromatic 6-membered rings fused directly to one another at all.

There follows a description of preferred ligands L' as occur compounds of the formula (1). By definition, the ligands L' are mono- or bidentate ligands. The ligands L' are preferably uncharged, monoanionic, dianionic or trianionic ligands, more preferably uncharged or monoanionic ligands. Preference is given to bidentate ligands L'.

Preferred uncharged monodentate ligands L' are selected from carbon monoxide, nitrogen monoxide, alkyl cyanides, for example acetonitrile, aryl cyanides, for example benzonitrile, alkyl isocyanides, for example methyl isonitrile, aryl isocyanides, for example benzoisonitrile, amines, for example trimethylamine, triethylamine, morpholine, phosphines, especially halophosphines, trialkylphosphines, triarylphosphines or alkylarylphosphines, for example trifluorophosphine, trimethylphosphine, tricyclohexylphosphine, tri-tert-butylphosphine, triphenylphosphine, tris(pentafluorophenyl)phosphine, phosphites, for example trimethyl phosphite, triethyl phosphite, arsines, for example trifluoroarsine, trimethylarsine, tricyclohexylarsine, tri-tert-butylarsine, triphenylarsine, tris(pentafluorophenyl)arsine, stibines, for example trifluorostibine, trimethylstibine, tricyclohexylstibine, tri-tert-butylstibine, triphenylstibine, tris(pentafluorophenyl)stibine, nitrogen-containing heterocycles, for example pyridine, pyridazine, pyrazine, pyrimidine, triazine, and carbenes, especially Arduengo carbenes.

Preferred monoanionic monodentate ligands L' are selected from hydride, deuteride, the halides F$^-$, Cl$^-$, Br and I$^-$, alkylacetylides, for example methyl-C≡C$^-$, tert-butyl-C≡C$^-$, arylacetylides, for example phenyl-C≡C$^-$, cyanide, cyanate, isocyanate, thiocyanate, isothiocyanate, aliphatic or aromatic alkoxides, for example methoxide, ethoxide, propoxide, iso-propoxide, tert-butoxide, phenoxide, aliphatic or aromatic thioalkoxides, for example methanethiolate, ethanethiolate, propanethiolate, iso-propanethiolate, tert-thiobutoxide, thiophenoxide, amides, for example dimethylamide, diethylamide, di-iso-propylamide, morpholide, carboxylates, for example acetate, trifluoroacetate, propionate, benzoate, aryl groups, for example phenyl, naphthyl, and anionic nitrogen-containing heterocycles such as pyrrolide, imidazolide, pyrazolide. At the same time, the alkyl groups in these groups are preferably C$_1$-C$_{20}$-alkyl groups, more preferably C$_1$-C$_{10}$-alkyl groups, most preferably C$_1$-C$_4$-alkyl groups. An aryl group is also understood to mean heteroaryl groups. These groups are as defined above.

Preferred di- or trianionic ligands are O$^{2-}$, S$^{2-}$, carbides which lead to a coordination of the R—C≡M form, and nitrenes which lead to a coordination of the R—N=M form, where R is generally a substituent, and N$^{3-}$. Preferred uncharged or mono- or dianionic, bidentate or higher polydentate ligands L' are selected from diamines, for example ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, for example 2-[1-(phenylimino)ethyl]pyridine, 2-[1-(2-methylphenylimino)ethyl]pyridine, 2-[1-(2,6-di-iso-propylphenylimino)ethyl]pyridine, 2-[1-(methylimino)ethyl]pyridine, 2-[1-(ethylimino)ethyl]pyridine, 2-[(1-(iso-propylimino)ethyl]pyridine, 2-[1-(tert-butylimino)ethyl]pyridine, diimines, for example 1,2-bis(methylimino)ethane, 1,2-bis(ethylimino)ethane, 1,2-bis(iso-propylimino)ethane, 1,2-bis(tert-butylimino)ethane, 2,3-bis(methylimino)butane, 2,3-bis(ethylimino)butane, 2,3-bis(iso-propylimino)butane, 2,3-bis(tert-butylimino)butane, 1,2-bis(phenylimino)ethane, 1,2-bis(2-methylphenylimino)ethane, 1,2-bis(2,6-di-iso-propylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-di-iso-propylphenylimino)butane, 2,3-bis(2,6-di-tert-butylphenylimino)butane, heterocycles containing two nitrogen atoms, for example 2,2'-bipyridine, o-phenanthroline, diphosphines, for example bis(diphenylphosphino)methane, bis(diphenylphosphino)ethane, bis(diphenylphosphino)propane, bis(diphenylphosphino)butane, bis(dimethylphosphino)methane, bis(dimethylphosphino)ethane, bis(dimethylphosphino)propane, bis(diethylphosphino)methane, bis(diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, for example acetylacetone, benzoylacetone, 1,5-diphenylacetylacetone, dibenzoylmethane, bis(1,1,1-trifluoroacetyl)methane, 2,2,6,6-tetramethyl-3,5-heptanedione, 3-ketonates derived from 3-ketoesters, for example ethyl acetoacetate, carboxylates derived from aminocarboxylic acids, for example pyridine-2-carboxylic acid, quinoline-2-carboxylic acid, glycine, N,N-dimethylglycine, alanine, N,N-dimethylaminoalanine, salicyliminates derived from salicylimines, for example methylsalicylimine, ethylsalicylimine, phenylsalicylimine, dialkoxides derived from dialcohols, for example ethylene glycol, 1,3-propylene glycol, and dithiolates derived from dithiols, for example ethylene-1,2-dithiol, propylene-1,3-dithiol.

In a further preferred embodiment of the invention, the ligands L' are bidentate monoanionic ligands having, together with the iridium, a cyclometalated five-membered ring or six-membered ring having at least one iridium-carbon bond, especially a cyclometalated five-membered ring. These are especially ligands as generally used in the field of phosphorescent metal complexes for organic electroluminescent devices, i.e. ligands of the phenylpyridine, naphthylpyridine, phenylquinoline, phenylisoquinoline type, etc., each of which may be substituted by one or more R radicals. The person skilled in the art in the field of phosphorescent electroluminescent devices is aware of a multitude of such ligands, and will be able without exercising inventive skill to select further ligands of this kind as ligand L' for compounds of formula (1). It is generally the case that a particularly suitable combination for the purpose is that of two groups as shown by the formulae (16) to (43) which follow, where one group binds via an uncharged atom and the other group via a negatively charged atom. In this case, the uncharged atom is especially an uncharged nitrogen atom or a carbene carbon atom and the negatively charged atom is especially a negatively charged carbon atom, a negatively charged nitrogen atom or a negatively charged oxygen atom. The ligand L' can then be formed from the groups of the formulae (16) to (43) by virtue of these groups each binding to one another at the position indicated by #. The positions at which the groups coordinate to the metal are indicated by *. In addition, it is also possible here for two adjacent R radicals each bonded to the two groups of the formulae (16) to (43) to form an aliphatic or aromatic ring system with one another.

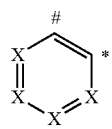

Formula (16)

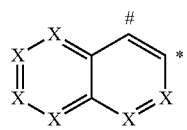

Formula (17)

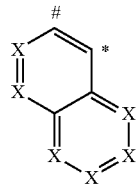

Formula (18)

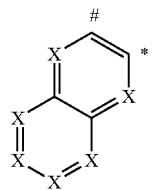

Formula (19)

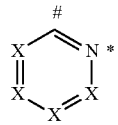

Formula (20)

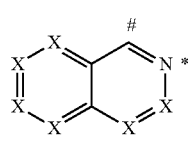

Formula (21)

-continued

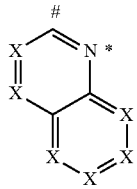

Formula (22)

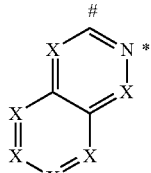

Formula (23)

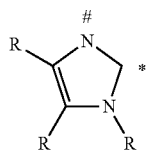

Formula (24)

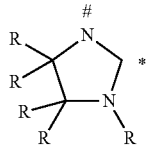

Formula (25)

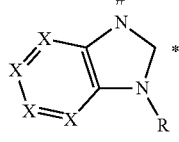

Formula (26)

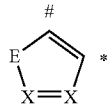

Formula (27)

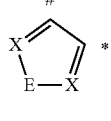

Formula (28)

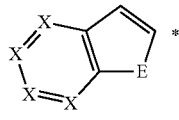

Formula (29)

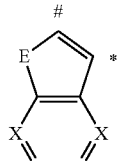

Formula (30)

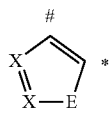

Formula (31)

-continued

Formula (32)
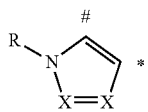

Formula (33)
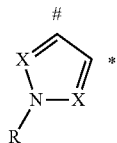

Formula (34)
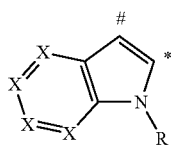

Formula (35)
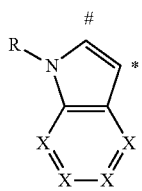

Formula (36)
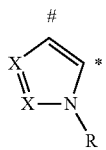

Formula (37)
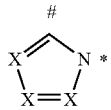

Formula (38)
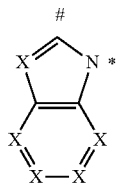

Formula (39)
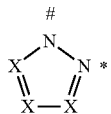

Formula (40)
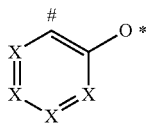

Formula (41)
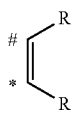

Formula (42)
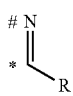

Formula (43)
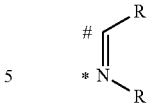

In these formulae, the symbols used have the same meaning as described above, E is O, S or $CR^2$, and preferably not more than two symbols X in each group are N, more preferably not more than one symbol X in each group is N. Most preferably, all symbols X are CR.

In a very particularly preferred embodiment of the invention, the ligand L' is a monoanionic ligand which is formed from two of the groups of the formula (16) to (43), where one of these groups coordinates to the iridium via a negatively charged carbon atom and the other of these groups via an uncharged nitrogen atom.

It may likewise be preferable when two adjacent symbols X in these ligands are a group of the abovementioned formula (4) or (5).

The further preferred R radicals in the structures detailed above are as defined for the R radicals of the ligand L.

The ligands L and L' may also be chiral depending on the structure. This is the case especially when they contain a bicyclic group of the formula (5) or when they contain substituents, for example alkyl, alkoxy, dialkylamino or aralkyl groups, having one or more stereocenters. Since the base structure of the complex may also be a chiral structure, the formation of diastereomers and multiple pairs of enantiomers is possible. In that case, the complexes of the invention include both the mixtures of the different diastereomers or the corresponding racemates and the individual isolated diastereomers or enantiomers.

The compounds of the invention may also be rendered soluble by suitable substitution, for example by comparatively long alkyl groups (about 4 to 20 carbon atoms), especially branched alkyl groups, or optionally substituted aryl groups, for example xylyl, mesityl or branched terphenyl or quaterphenyl groups. Such compounds are then soluble in sufficient concentration at room temperature in standard organic solvents to be able to process the complexes from solution, for example by printing methods.

The abovementioned preferred embodiments can be combined with one another as desired. In a particularly preferred embodiment of the invention, the abovementioned preferred embodiments apply simultaneously.

The metal complexes of the invention are preparable in principle by various processes. However, the processes described hereinafter have been found to be particularly suitable.

Therefore, the present invention further provides a process for preparing the inventive compounds of formula (1) by reacting the corresponding free ligands with iridium alkoxides of the formula (44), with iridium ketoketonates of the formula (45), with iridium halides of the formula (46) or with dimeric iridium complexes of the formula (47) or (48):

Formula (44)
$$Ir(OR^1)_n$$

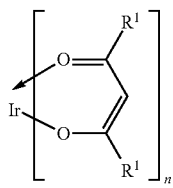

Formula (45)

IrHal$_n$

Formula (46)

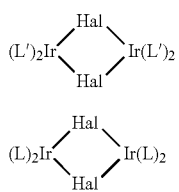

Formula (47)

(L)$_2$Ir⟨Hal⟩Ir(L)$_2$ Formula (48)

where the symbols and indices L', m, n and R$^1$ are as defined above and Hal=F, Cl, Br or I.

The synthesis can also be conducted by reacting the ligands L with iridium complexes of the formula [Ir(L')$_2$(HOMe)$_2$]A or [Ir(L')$_2$(NCMe)$_2$]A or by reacting the ligands L' with iridium complexes of the formula [Ir(L)$_2$(HOMe)$_2$]A or [Ir(L)$_2$(NCMe)$_2$]A, where A in each case is a non-coordinating anion, for example triflate, tetrafluoroborate, hexafluorophosphate, etc., in dipolar protic solvents, for example ethylene glycol, propylene glycol, glycerol, diethylene glycol, triethylene glycol, etc. It is likewise possible to use iridium compounds bearing both alkoxide and/or halide and/or hydroxyl and ketoketonate radicals. These compounds may also be charged. Corresponding iridium compounds of particular suitability as reactants are disclosed in WO 2004/085449. [IrCl$_2$(acac)$_2$]$^−$ is particularly suitable, for example Na[IrCl$_2$(acac)$_2$]. Further particularly suitable iridium reactants are iridium(III) tris(acetylacetonate) and iridium(II) tris(2,2,6,6-tetramethyl-3,5-heptanedionate).

The synthesis of the complexes is preferably conducted as described in WO 2002/060910 and in WO 2004/085449. Heteroleptic complexes can be synthesized, for example, according to WO 05/042548 as well. In this case, the synthesis can, for example, also be activated by thermal or photochemical means and/or by microwave radiation. In addition, the synthesis can also be conducted in an autoclave at elevated pressure and/or elevated temperature.

The reactions can in principle also be conducted without addition of solvents or melting aids in a melt of the corresponding ligands to be o-metalated. It is optionally possible to add solvents or melting aids. Suitable solvents are protic or aprotic solvents such as aliphatic and/or aromatic alcohols, for example methanol, ethanol, isopropanol, t-butanol, etc., oligo- and polyalcohols, for example ethylene glycol, propane-1,2-diol or glycerol, alcohol ethers, for example ethoxyethanol, diethylene glycol, triethylene glycol, polyethylene glycol, etc., ethers, for example di- and triethylene glycol dimethyl ether, diphenyl ether, etc., aromatic, heteroaromatic and/or aliphatic hydrocarbons, for example toluene, xylene, mesitylene, chlorobenzene, pyridine, lutidine, quinoline, isoquinoline, tridecane, hexadecane, etc., amides, for example DMF, DMAC, etc., lactams, for example NMP, sulfoxides, for example DMSO, or sulfones, for example dimethyl sulfone, sulfolane, etc. Suitable melting aids are compounds that are in solid form at room temperature but melt when the reaction mixture is heated and dissolve the reactants, so as to form a homogeneous melt. Particularly suitable are biphenyl, m-terphenyl, triphenyls, 1,2-, 1,3- or 1,4-bisphenoxybenzene, triphenylphosphine oxide, 18-crown-6, phenol, 1-naphthol, hydroquinone, etc.

For the processing of the inventive compounds from the liquid phase, for example by spin-coating or by printing methods, formulations of the inventive compounds are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be a further organic or inorganic compound which is likewise used in the electronic device, for example a matrix material. This further compound may also be polymeric.

The above-described complexes of formula (1) and the above-detailed preferred embodiments can be used as active component in an electronic device. The present invention therefore further provides for the use of a compound of formula (1) or according to one of the preferred embodiments in an electronic device. In addition, the compounds of the invention can be used for production of singlet oxygen, in photocatalysis or in oxygen sensors.

The present invention still further provides an electronic device comprising at least one compound of formula (1) or according to one of the preferred embodiments.

An electronic device is understood to mean any device comprising anode, cathode and at least one layer, said layer comprising at least one organic or organometallic compound. The electronic device of the invention thus comprises anode, cathode and at least one layer comprising at least one compound of the above-detailed formula (1). Preferred electronic devices are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) and organic laser diodes (O-lasers), comprising at least one compound of the above-detailed formula (1) in at least one layer. Particular preference is given to organic electroluminescent devices. Active components are generally the organic or inorganic materials introduced between the anode and cathode, for example charge injection, charge transport or charge blocker materials, but especially emission materials and matrix materials. The compounds of the invention exhibit particularly good properties as emission material in organic electroluminescent devices. A preferred embodiment of the invention is therefore organic electroluminescent devices.

The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers, charge generation layers and/or organic or inorganic p/n junctions. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. A preferred embodiment is three-layer systems where the three layers exhibit blue, green and orange or red emission (see, for example, WO 2005/011013), or systems having more than three emitting layers. A further preferred embodiment is two-layer systems where the two layers exhibit either blue and yellow emission or blue-green and orange emission. Two-layer systems are of interest especially for lighting applications. Embodiments of this kind are particularly suitable with the compounds of the invention, since they frequently exhibit yellow or orange emission. The white-emitting electroluminescent devices can be used for lighting applications or as a backlight for displays or with color filters as a display.

In a preferred embodiment of the invention, the organic electroluminescent device comprises the compound of formula (1) or the above-detailed preferred embodiments as emitting compound in one or more emitting layers.

When the compound of formula (1) is used as emitting compound in an emitting layer, it is preferably used in combination with one or more matrix materials. The mixture of the compound of formula (1) and the matrix material contains between 1% and 99% by volume, preferably between 2% and 90% by volume, more preferably between 3% and 40% by volume and especially between 5% and 15% by volume of the compound of formula (1), based on the overall mixture of emitter and matrix material. Correspondingly, the mixture contains between 99% and 1% by volume, preferably between 98% and 10% by volume, more preferably between 97% and 60% by volume and especially between 95% and 85% by volume of the matrix material(s), based on the overall mixture of emitter and matrix material.

The matrix material used may generally be any materials which are known for the purpose according to the prior art. The triplet level of the matrix material is preferably higher than the triplet level of the emitter.

Suitable matrix materials for the compounds of the invention are ketones, phosphine oxides, sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/1054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015, or bridged carbazole derivatives, for example according to US 2009/0136779, WO 2010/050778, WO 2011/042107 or WO 2011/088877.

It may also be preferable to use a plurality of different matrix materials as a mixture. Especially suitable for this purpose are mixtures of at least one electron-transporting matrix material and at least one hole-transporting matrix material or mixtures of at least two electron-transporting matrix materials or mixtures of at least one hole- or electron-transporting matrix material and at least one further material which has a large bandgap and is thus substantially electrically inert and is not involved to a substantial extent, if any, in the charge transport, as described, for example, in WO 2010/108579. A preferred combination is, for example, the use of an aromatic ketone or a triazine derivative with a triarylamine derivative or a carbazole derivative as mixed matrix for the metal complex of the invention.

It is further preferable to use a mixture of two or more triplet emitters together with a matrix. In this case, the triplet emitter having the shorter-wave emission spectrum serves as co-matrix for the triplet emitter having the longer-wave emission spectrum. For example, it is possible to use blue- or green-emitting triplet emitters as co-matrix for the inventive complexes of formula (1).

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent in order to enable the irradiation of the organic material (O-SC) or the emission of light (OLED/PLED, O-laser). A preferred structure uses a transparent anode. Preferred anode materials here are conductive mixed metal oxides. Particular preference is given to indium tin oxide (ITO) or indium zinc oxide (IZO). Preference is further given to conductive doped organic materials, especially conductive doped polymers.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an organic electroluminescent device, characterized in that one or more layers are coated by a sublimation process. In this case, the materials are applied by vapor deposition in vacuum sublimation systems at an initial pressure of typically less than $10^{-5}$ mbar, preferably less than $10^{-6}$ mbar. It is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing or offset printing, but more preferably LITI (light-induced thermal imaging, thermal transfer printing) or inkjet printing, For this purpose, soluble compounds are needed, which are obtained, for example, through suitable substitution.

The organic electroluminescent device can also be produced as a hybrid system by applying one or more layers from solution and applying one or more other layers by vapor deposition. For example, it is possible to apply an emitting layer comprising a compound of formula (1) and a matrix material from solution, and to apply a hole blocker layer and/or an electron transport layer thereto by vapor deposition under reduced pressure.

These methods are known in general terms to those skilled in the art and can be applied without difficulty to organic electroluminescent devices comprising compounds of formula (1) or the above-detailed preferred embodiments.

The electronic devices of the invention, especially organic electroluminescent devices, are notable for the following surprising advantages over the prior art:

1. Organic electroluminescent devices comprising compounds of formula (1) as emitting materials have a very good lifetime. More particularly, they have a better lifetime than electroluminescent devices which contain analogous compounds but do not contain a fused-on aliphatic five-membered ring of the formula (4) or (5).
2. Organic electroluminescent devices comprising compounds of formula (1) as emitting materials have a very good efficiency. More particularly, they have a better efficiency than electroluminescent devices which contain analogous compounds but do not contain a fused-on aliphatic five-membered ring of the formula (4) or (5).
3. Organic electroluminescent devices comprising compounds of formula (1) as emitting materials have a very low operating voltage.

These abovementioned advantages are not accompanied by a deterioration in the further electronic properties.

The invention is illustrated in detail by the examples which follow, without any intention of restricting it thereby. The person skilled in the art will be able to use the details given, without exercising inventive skill, to prepare further compounds of the invention and use them in electronic devices, and will thus be able to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from VWR, Sigma-ALDRICH or ABCR. The numbers for the compounds known from the literature, some of which are also stated in square brackets, are the CAS numbers of the compounds.

2,3-Substituted Benzo[h]Quinolines—Synthesis Methods

General Method:

An aromatic o-aminocarbaldehyde (400 mmol) is dissolved in 1.1 of dry 1,4-dioxane at 60° C. and the entire apparatus is carefully purged with inert gas. A (bi)cyclic α-methylene ketone (600 mmol, 1.5 eq) and potassium tert-butoxide (400 mmol, 1 eq) are added and the reaction mixture is heated to 90° C. until the reactant has been entirely depleted. After cooling, the reaction is diluted with water and extracted with ethyl acetate. The organic phases are combined, washed with water and saturated NaCl solution and freed of the solvent under reduced pressure. The residue is taken up in 1 of dichloromethane and filtered through silica gel. For further removal of secondary components, recrystallization is effected from methanol and column chromatography purification is effected using silica gel with ethyl acetate/heptane.

Example: Ligand 1 (L1)

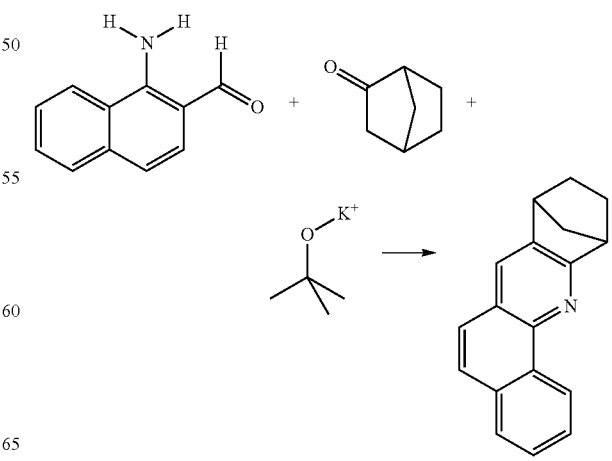

1-aminonaphthalene-2-carbaldehyde (407 mmol, 69.7 g), norcamphor (611 mmol, 67.3 g, 1.5 eq) and, as base, potassium tert-butoxide (407 mmol, 45.7 g) are converted by the general method. For removal of secondary components, recrystallization is effected from methanol and column chromatography purification is effected using silica gel with ethyl acetate/heptane (1:5). 63.7 g (259 mmol, 64%) of a colorless solid are obtained.

The reactants reacted with one another by the general method may be the o-aminocarbaldehydes and (bi)cyclic α-methylene ketones specified in the following tables:

| Ex. | o-Aminocarbaldehyde | (Bi)cyclic α-methylene ketone | Ligand | Yield |
|-----|---------------------|-------------------------------|--------|-------|
| L1  | 176853-41-1         | 497-38-1                      |        | 64%   |
| L2  |                     | 38857-63-5                    |        | 53%   |
| L3  |                     | 4694-11-5                     |        | 33%   |
| L4  |                     | 180690-80-6                   |        | 40%   |

-continued
| Ex. | o-Amino-carbaldehyde | (Bi)cyclic α-methylene ketone | Ligand | Yield |
|---|---|---|---|---|
| L5 | 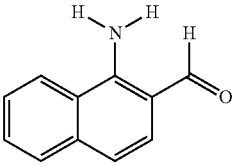 [SMILES: Nc1c(C=O)ccc2ccccc12] | 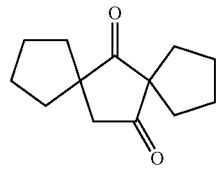  31934-44-8 | 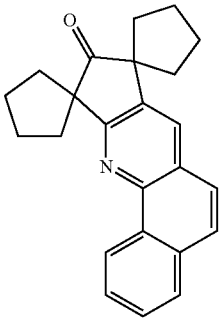 [SMILES: O=C1C2(CCCC2)c2cc3ccc4ccccc4c3nc2C12CCCC2] | 11% |
| L6 | 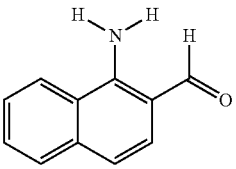 [SMILES: Nc1c(C=O)ccc2ccccc12] | 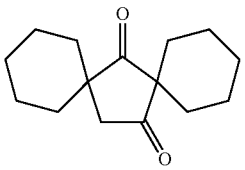  31934-45-9 | 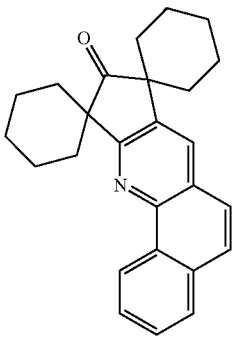 [SMILES: O=C1C2(CCCCC2)c2cc3ccc4ccccc4c3nc2C12CCCCC2] | 9% |
| L7 | 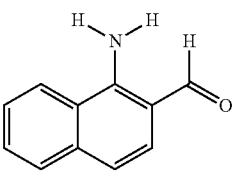 [SMILES: Nc1c(C=O)ccc2ccccc12] | 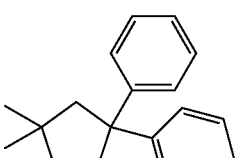  202203-04-1 | 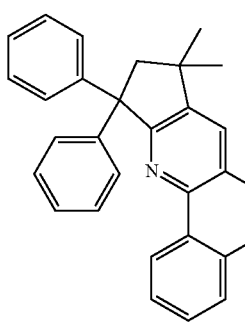 | 43% |
| L8 | 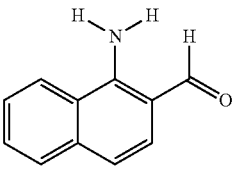 [SMILES: Nc1c(C=O)ccc2ccccc12] | 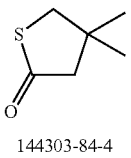  144303-84-4 | 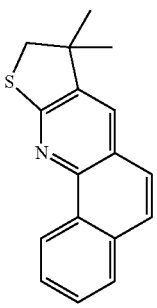 [SMILES: CC1(C)CSc2nc3c(ccc4ccccc43)cc21] | 53% |

-continued
| Ex. | o-Amino-carbaldehyde | (Bi)cyclic α-methylene ketone | Ligand | Yield |
|---|---|---|---|---|
| L9 | 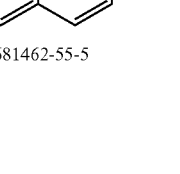 681462-55-5 |  | 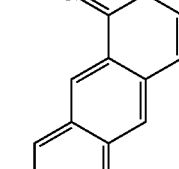 | 30% |
| L10 | 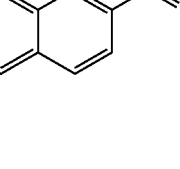 |  | 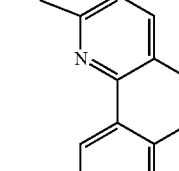 | 36% |
| L11 | 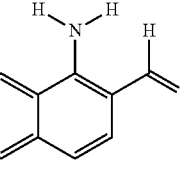 | 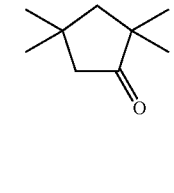 | 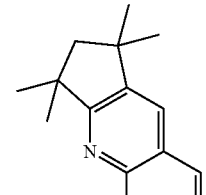 | 24% |
| L12 | 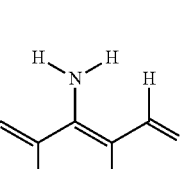 | 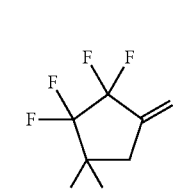 | 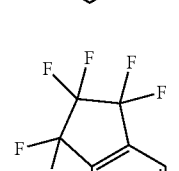 | 29% |

-continued
| Ex. | o-Amino-carbaldehyde | (Bi)cyclic α-methylene ketone | Ligand | Yield |
|---|---|---|---|---|
| L13 | 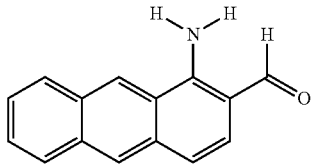 | 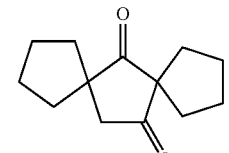 | 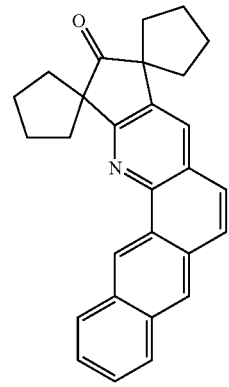 [SMILES: O=C1C2(CCCC2)c2cc3ccc4cc5ccccc5cc4c3nc2C12CCCC2] | 30% |
| L14 | 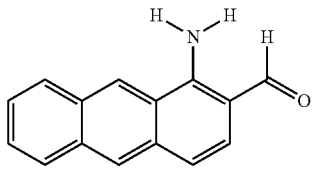 [SMILES: Nc1c(C=O)ccc2cc3ccccc3cc12] | 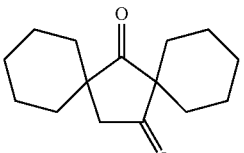 | 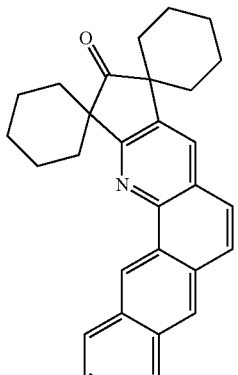 | 32% |
| L15 | 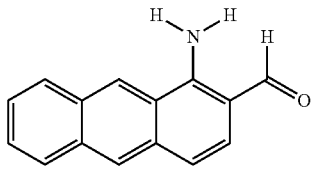 [SMILES: Nc1c(C=O)ccc2cc3ccccc3cc12] | 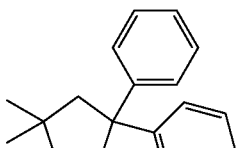 | 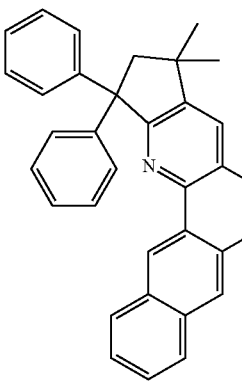 | 30% |
| L16 | 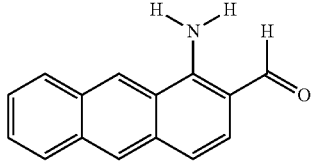 [SMILES: Nc1c(C=O)ccc2cc3ccccc3cc12] | 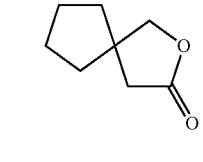 | 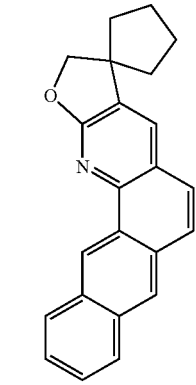 [SMILES: c1ccc2cc3c(ccc4cc5c(nc43)OCC53CCCC3)cc2c1] | 26% |

-continued

| Ex. | o-Amino-carbaldehyde | (Bi)cyclic α-methylene ketone | Ligand | Yield |
|---|---|---|---|---|
| L17 | | | | 39% |
| L18 | 427375-46-0 | | | 36% |
| L19 | | | | 23% |
| L20 | | | | 38% |

-continued

| Ex. | o-Amino-carbaldehyde | (Bi)cyclic α-methylene ketone | Ligand | Yield |
|---|---|---|---|---|
| L21 | | | | 31% |
| L22 | | | | 22% |
| L23 | | | | 24% |
| L24 | | | | 27% |

-continued
| Ex. | o-Amino-carbaldehyde | (Bi)cyclic α-methylene ketone | Ligand | Yield |
|---|---|---|---|---|
| L25 | 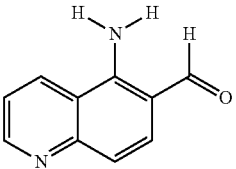 [SMILES: Nc1c(C=O)ccc2ncccc12] | 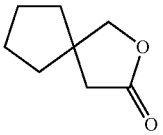 | 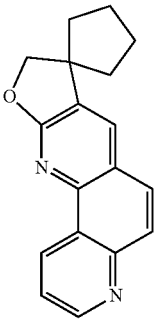 [SMILES: c1cnc2ccc3cc4c(nc3c2c1)OCC41CCCC1] | 32% |
| L26 | 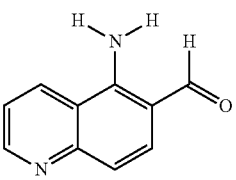 [SMILES: Nc1c(C=O)ccc2ncccc12] | 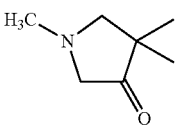 | 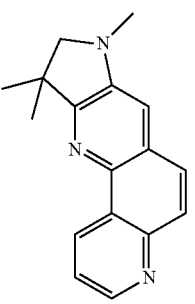 [SMILES: CN1CC(C)(C)c2nc3c(ccc4ncccc43)cc21] | 37% |
| L27 | 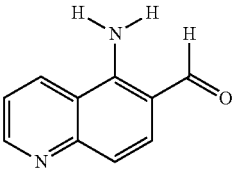 [SMILES: Nc1c(C=O)ccc2ncccc12] | 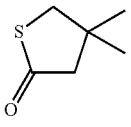 | 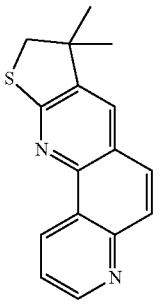 [SMILES: CC1(C)CSc2nc3c(ccc4ncccc43)cc21] | 29% |
| L28 | 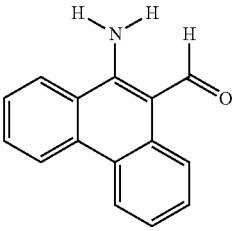
1224954-00-0 | 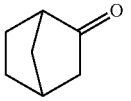 | 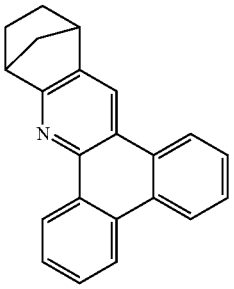 [SMILES: c1ccc2c(c1)c1ccccc1c1nc3c(cc21)C1CCC3C1] | 58% |
| L29 | 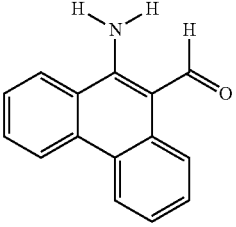 [SMILES: Nc1c(C=O)c2ccccc2c2ccccc12] | 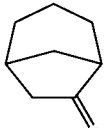 | 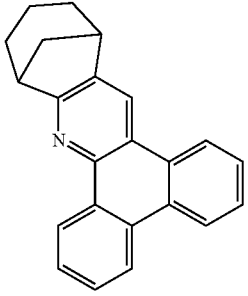 [SMILES: c1ccc2c(c1)c1ccccc1c1nc3c(cc21)C1CCCC3C1] | 48% |

| Ex. | o-Amino-carbaldehyde | (Bi)cyclic α-methylene ketone | Ligand | Yield |
|---|---|---|---|---|
| L30 | 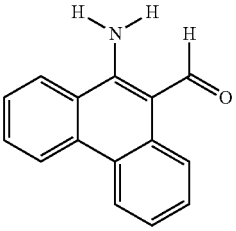 [SMILES: Nc1c(C=O)c2ccccc2c2ccccc12] | 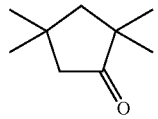 | 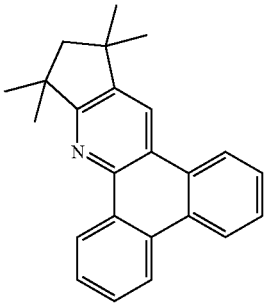 [SMILES: CC1(C)CC(C)(C)c2nc3c4ccccc4c4ccccc4c3cc21] | 37% |
| L31 | 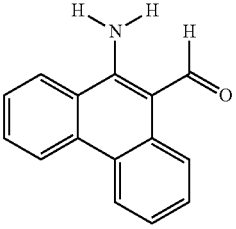 [SMILES: Nc1c(C=O)c2ccccc2c2ccccc12] | 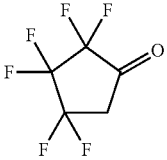 | 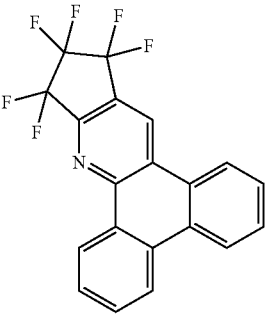 [SMILES: FC1(F)c2cc3c4ccccc4c4ccccc4c3nc2C(F)(F)C1(F)F] | 32% |
| L32 | 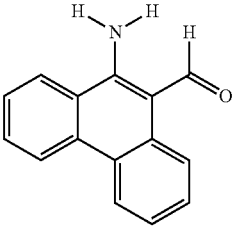 [SMILES: Nc1c(C=O)c2ccccc2c2ccccc12] | 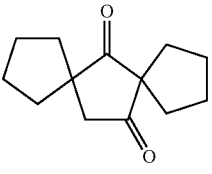 [SMILES: O=C1CC2(CCCC2)C(=O)C12CCCC2] | 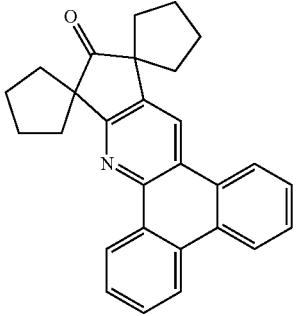 [SMILES: O=C1C2(CCCC2)c2cc3c4ccccc4c4ccccc4c3nc2C12CCCC2] | 34% |
| L33 | 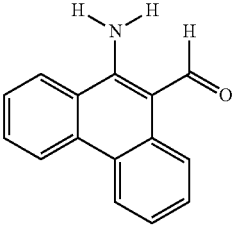 [SMILES: Nc1c(C=O)c2ccccc2c2ccccc12] | 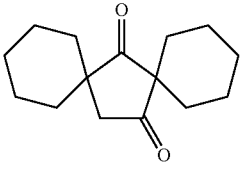 [SMILES: O=C1CC2(CCCCC2)C(=O)C12CCCCC2] | 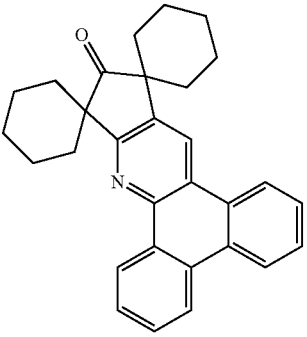 [SMILES: O=C1C2(CCCCC2)c2cc3c4ccccc4c4ccccc4c3nc2C12CCCCC2] | 35% |

| Ex. | o-Amino-carbaldehyde | (Bi)cyclic α-methylene ketone | Ligand | Yield |
|---|---|---|---|---|
| L34 | | | | 36% |
| L35 | | | | 31% |
| L36 | | | | 71% |
3,4-substituted benzo[h]quinolines
Reaction Scheme:
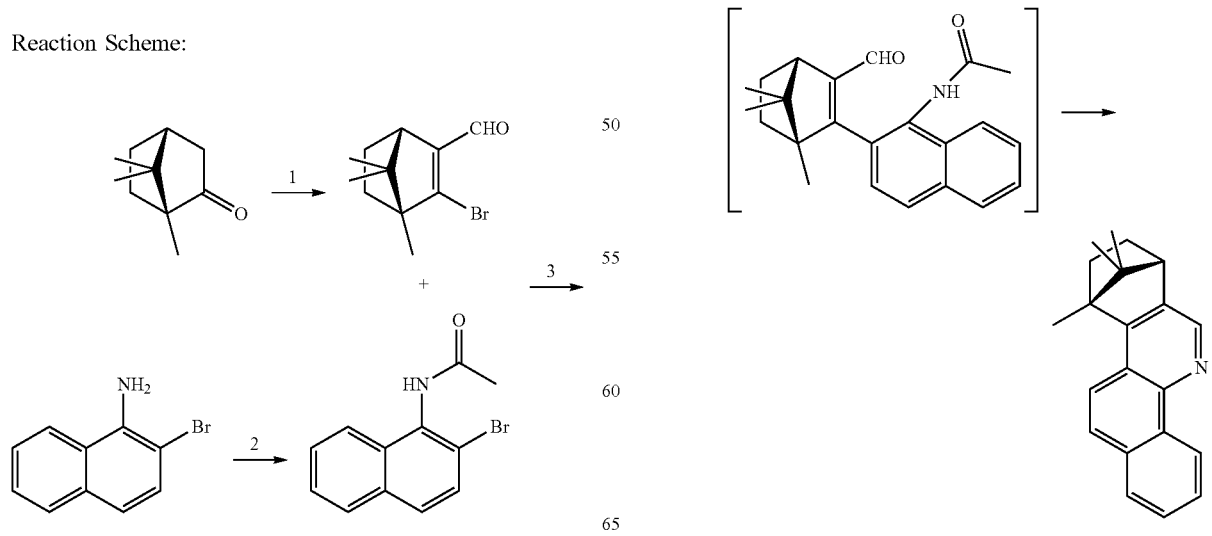

Synthesis Methods
General Method for Step 1: Conversion of an α-methylene Ketone to a Bromoalkenecarbaldehyde A mixture of DMF (25 mL) and chloroform (80 mL) is cooled to 0° C. and inertized. 5.8 mL (60 mmol) of PBr$_3$ in 10 mL of chloroform are slowly added dropwise and the reaction mixture is stirred at room temperature for 2 h. The suspension is heated to reflux and the ketone (50 mmol) in 15 mL of chloroform is slowly added dropwise. The reaction is boiled under reflux for a further 12 h, cooled down and added gradually to a 1 M NaOH solution. The mixture is extracted repeatedly with diethyl ether and dried over sodium sulfate, and the solvent is removed under reduced pressure.

Example for S2:

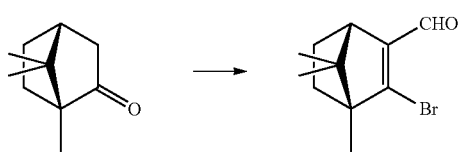

A mixture of DMF (25 mL) and chloroform (80 mL) is cooled to 0° C. and inertized. 5.8 mL (60 mmol) of PBr$_3$ in 10 mL of chloroform are slowly added dropwise and the reaction mixture is stirred at room temperature for 2 h. The suspension is heated to reflux and the (+)-camphor (50 mmol, 7.6 g) in 15 mL of chloroform is slowly added dropwise. The mixture is boiled under reflux for a further 12 h, cooled down and added gradually to a 1 M NaOH solution. The mixture is extracted repeatedly with diethyl ether and dried over sodium sulfate, and the solvent is removed under reduced pressure. The oil obtained is purified further by means of a vacuum distillation. A pale yellow oil is obtained in a yield of 24% (2.92 g, 12 mmol). The following (bi)cyclic α-methylene ketones can be converted to bromoalkenecarbaldehydes by the general method in the yield reported:

| Ex. | Methylene ketone | Bromoalkene-carbaldehyde | Yield |
|---|---|---|---|
| S1 | 497-38-1 | | 27% |
| S2 | 464-49-3 | | 24% |
| S3 | 464-48-2 | | 15% |
| S4 | 10309-50-9 | | 8% |
| S5 | 38857-63-5 | | 21% |
| S6 | 4694-11-5 | | 14% |
| S7 | 180690-80-6 | | 44% |
| S8 | 31934-44-8 | | 13% |
| S9 | 31934-45-9 | | 10% |
| S10 | 1628-18-8 | | 22% |

| Ex. | Methylene ketone | Bromoalkene-carbaldehyde | Yield |
|---|---|---|---|
| S11 | 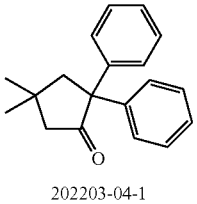 [SMILES: CC1(C)CC(=O)C(c2ccccc2)(c2ccccc2)C1] 202203-04-1 | 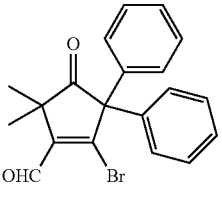 [SMILES: CC1(C)C(=O)C(c2ccccc2)(c2ccccc2)C(Br)=C1C=O] | 15% |
| S12 | 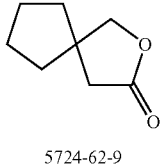 5724-62-9 | 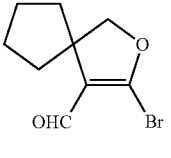 [SMILES: O=CC1=C(Br)OCC12CCCC2] | 12% |
| S13 | 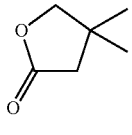 13861-97-7 | 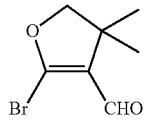 | 16% |
| S14 | 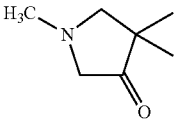 16348-93-9 | 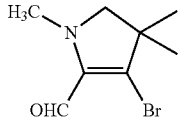 | 15% |
| S15 | 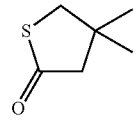 144303-84-4 | 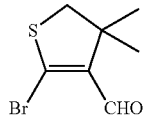 | 17% |

General Method for Step 2: N-acetylation of an o-aminobromonaphthalene

A 1-amino-2-bromoaromatic (100 mmol) is added in portions and with good stirring to an initial charge of acetic anhydride (2.1 mL, 20 mmol) cooled to 0° C. The ice bath is removed and the reaction mixture is heated to reflux for 30 minutes. After cooling, the acetic acid and the excess acetic anhydride are distilled off under reduced pressure. The residue is dissolved in dichloromethane or ethyl acetate and filtered through a silica gel column, such that the 1-(N-acetylamino)-2-bromoaromatic is obtained in 80%-95% yield.

Example for S100:

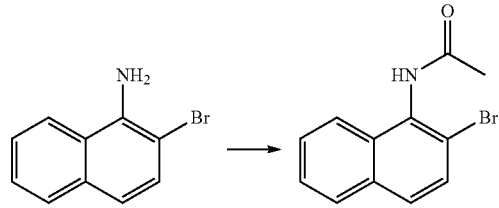

8.5 mL of acetic anhydride (90 mmol, 2 eq) are initially charged and cooled to 0° C. 10 g (45 mmol) of 2-bromoaminonaphthalene are added in small portions. The reaction mixture is allowed to warm up gradually to room temperature, then heated under reflux for 1 h. The mixture is cooled and the acetic acid or the excess acetic anhydride is distilled off under reduced pressure. The residue is dissolved in ethyl acetate and filtered through a silica gel column. 10.5 g (88%, 39.8 mmol) of a white solid are obtained.

The following N-acetylbromoaromatics can be obtained by the general method in the yield reported:

| Ex. | Amino-2-bromoaromatic | N-Acetylamino-2-bromoaromatic | Yield |
|---|---|---|---|
| S100 | 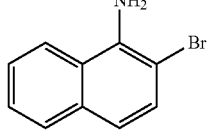 771-14-2 | 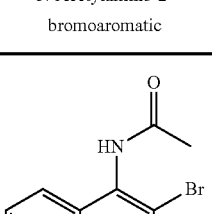 | 88% |
| S101 | 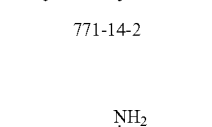 1240642-73-2 | 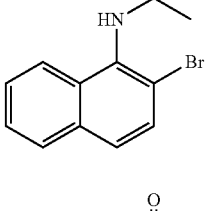 | 85% |
| S102 | 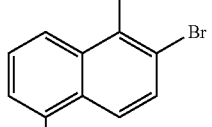 664364-38-9 | 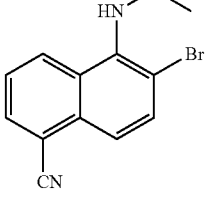 | 92% |
| S103 | 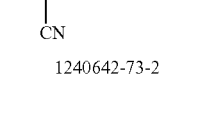 180411-17-0 | 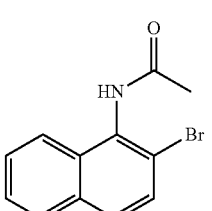 | 89% |
| S104 | 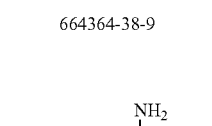 51670-76-9 | 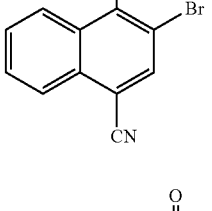 | 95% |

| Ex. | Amino-2-bromoaromatic | N-Acetylamino-2-bromoaromatic | Yield |
|---|---|---|---|
| S105 | MeO, MeO, NH₂, Br (180411-16-9) | MeO, MeO, HN-C(O)CH₃, Br | 80% |

General Method for Step 3: Coupling of the Bromoalkenecarbaldehyde with 1-(N-Acetylamino)-2-bromonaphthalene and Subsequent Cyclization A mixture of bromoalkenecarbaldehyde (5 mmol), the 1-(N-acetylamino)-2-bromoaromatic (5 mmol) from step 2, copper powder (2.6 g, 41 mmol) and Pd(PPh$_3$)$_4$ (577 mg, 0.5 mmol) is dissolved in 15 mL of dry DMSO and carefully inertized. The reaction mixture is heated to 85° C. for 12 h, then anhydrous K$_2$CO$_3$ is added and the mixture is heated for a further 6 h. The reaction mixture is cooled down and diluted with 100 mL of ethyl acetate. The mixture is filtered, and the filtrate is washed with water, dried over sodium sulfate and freed of the solvent under reduced pressure. The residue is purified by column chromatography and a colorless powder is obtained in 35%-65% yield.

Example for L501

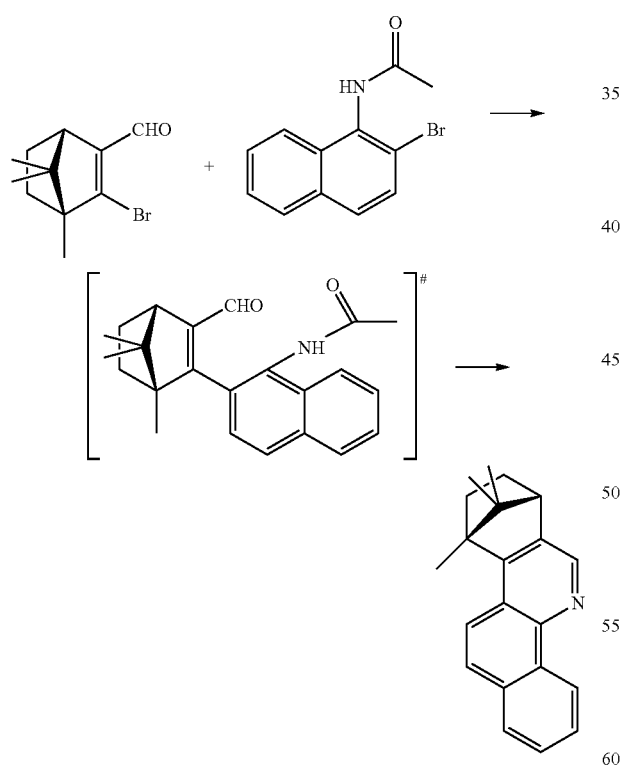

A mixture of bromoalkenecarbaldehyde (S2, 1.22 g, 5 mmol), the 1-(N-acetylamino)-2-bromonaphthalene (S100, 1.32 g, 5 mmol), copper powder (2.6 g, 41 mmol) and Pd(PPh$_3$)$_4$ (577 mg, 0.5 mmol) is dissolved in 15 mL of dry DMSO and carefully inertized. The reaction mixture is heated to 85° C. for 12 h, then anhydrous K$_2$CO$_3$ is added and the mixture is heated for a further 6 h. The reaction mixture is cooled down and diluted with 100 mL of ethyl acetate. The mixture is filtered, and the filtrate is washed with water, dried over sodium sulfate and freed of the solvent under reduced pressure. The residue is purified by column chromatography (silica gel, eluent: heptane/EA 3:1), and a colorless powder is obtained in 65% yield (1.13 g, 3.2 mmol).

The synthons S1-S15 can be used to prepare the following ligands by the general method:

| Ex. | Methylene ketone | Reactant 2 | Ligand | Yield |
|---|---|---|---|---|
| L500 | S1 | S100 | (structure) | 59% |
| L501 | S2 | S100 | (structure) | 65% |
| L502 | S3 | S100 | (structure) | 66% |
| L503 | S4 | S100 | (structure) | 49% |

| Ex. | Methylene ketone | Reactant 2 | Ligand | Yield |
|---|---|---|---|---|
| L504 | S5 | S100 | 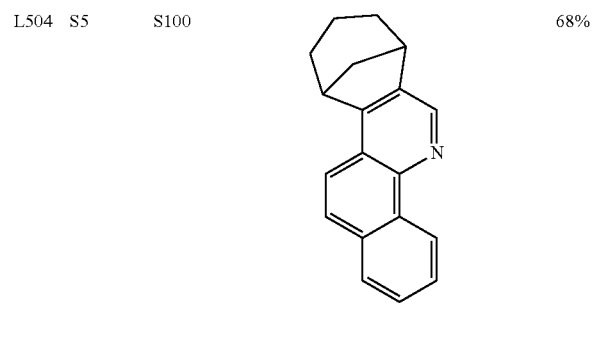 | 68% |
| L505 | S6 | S100 | 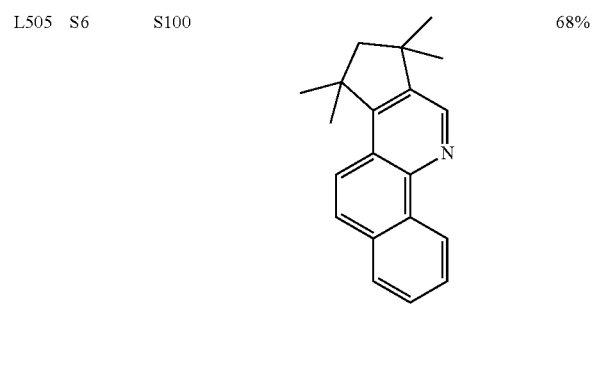 | 68% |
| L506 | S7 | S100 | 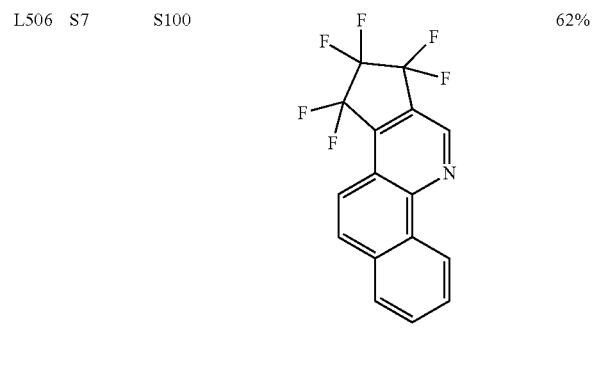 | 62% |
| L507 | S8 | S100 | 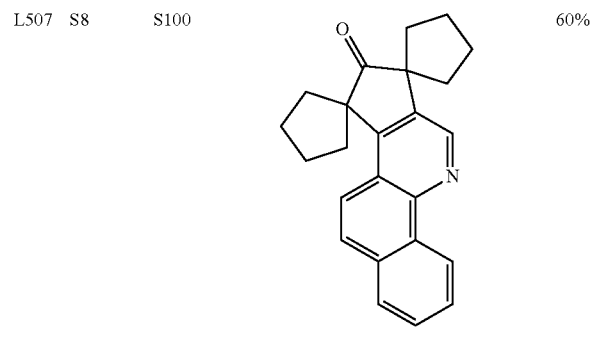 | 60% |
| L508 | S9 | S100 | 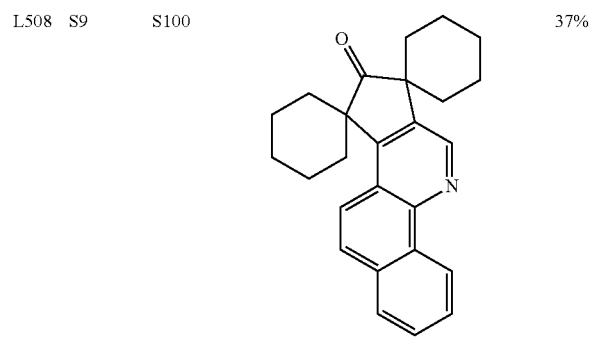 | 37% |
| L509 | S10 | S100 | 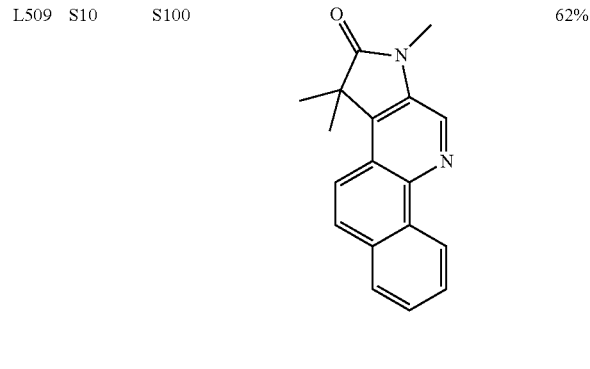 | 62% |
| L510 | S11 | S100 | 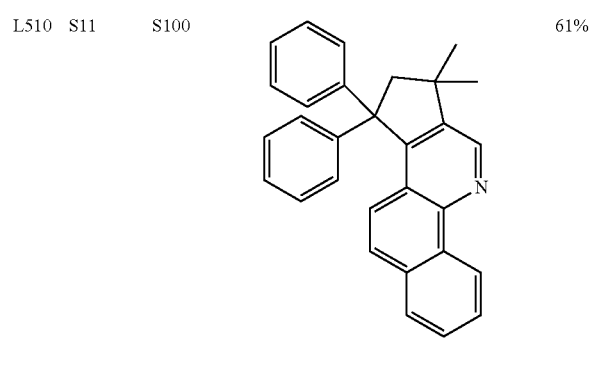 | 61% |
| L511 | S12 | S100 | 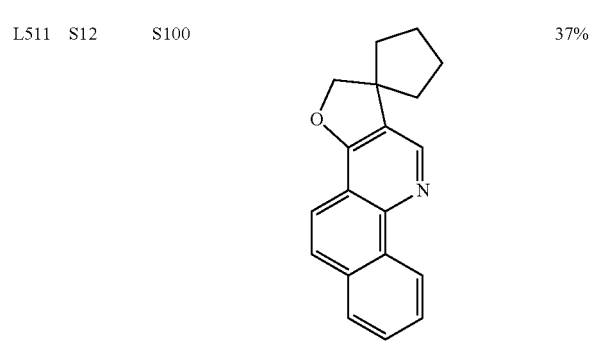 | 37% |

| Ex. | Methylene ketone | Reactant 2 | Ligand | Yield |
|---|---|---|---|---|
| L512 | S13 | S100 | 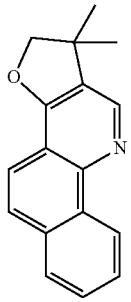 [SMILES: CC1(C)COc2c1cnc1c2ccc2ccccc21] | 38% |
| L513 | S14 | S100 | 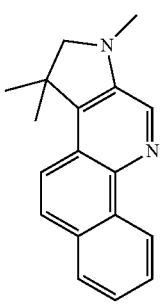 [SMILES: CN1CC(C)(C)c2c1cnc1c2ccc2ccccc21] | 43% |
| L514 | S15 | S100 | 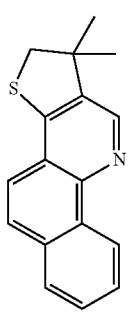 [SMILES: CC1(C)CSc2c1cnc1c2ccc2ccccc21] | 47% |
| L515 | S1 | S101 | 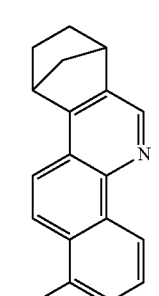 | 52% |
| L516 | S2 | S101 | 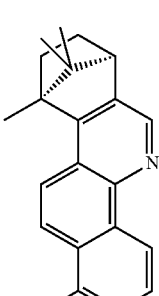 | 58% |
| Ex. | Methylene ketone | Reactant 2 | Ligand | Yield |
|---|---|---|---|---|
| L517 | S3 | S101 | 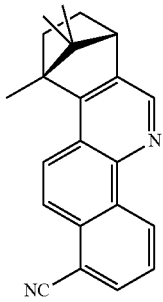 [SMILES: CC1(C)[C@@H]2CC[C@@]1(C)c1c2cnc2c1ccc1c(C#N)cccc12] | 37% |
| L518 | S4 | S101 | | 48% |
| L519 | S5 | S101 | 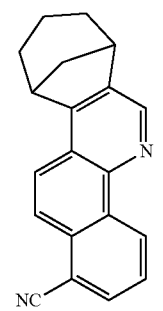 | 71% |
| L520 | S6 | S101 | 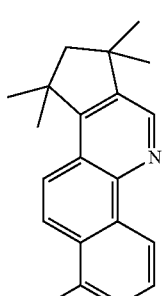 | 54% |
| L521 | S7 | S101 | 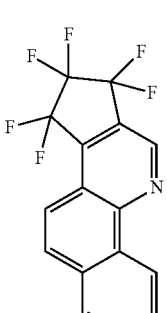 | 67% |

| Ex. | Methylene ketone | Reactant 2 | Ligand | Yield |
|---|---|---|---|---|
| L522 | S8 | S101 | 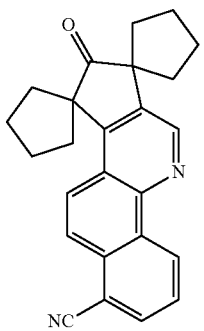 [SMILES: N#Cc1cccc2c1ccc1c3c(cnc12)C1(CCCC1)C(=O)C31CCCC1] | 51% |
| L523 | S9 | S101 | 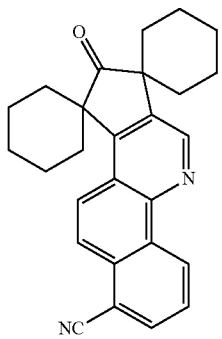 [SMILES: N#Cc1cccc2c1ccc1c3c(cnc12)C1(CCCCC1)C(=O)C31CCCCC1] | 53% |
| L524 | S10 | S101 | 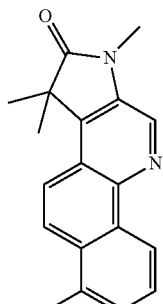 | 41% |
| L525 | S11 | S101 | 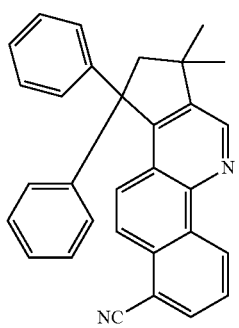 [SMILES: CC1(C)CC(c2ccccc2)(c2ccccc2)c2c1cnc1c2ccc2c(C#N)cccc21] | 51% |
| L526 | S12 | S101 | 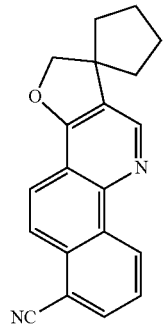 [SMILES: N#Cc1cccc2c1ccc1c3c(cnc12)C1(CCCC1)CO3] | 56% |
| L527 | S13 | S101 | 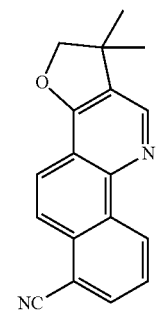 [SMILES: CC1(C)COc2c1cnc1c2ccc2c(C#N)cccc21] | 61% |
| L528 | S14 | S101 | 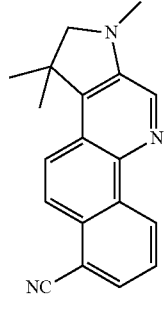 [SMILES: CN1CC(C)(C)c2c1cnc1c2ccc2c(C#N)cccc21] | 41% |
| L529 | S15 | S101 | 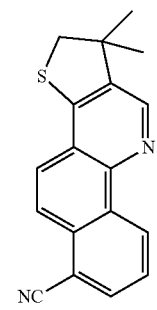 [SMILES: CC1(C)CSc2c1cnc1c2ccc2c(C#N)cccc21] | 59% |
| L530 | S1 | S102 | 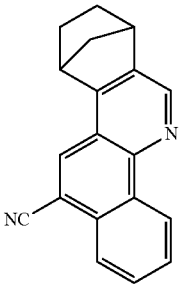 | 65% |

-continued
| Ex. | Methylene ketone | Reactant 2 | Ligand | Yield |
|---|---|---|---|---|
| L531 | S2 | S102 | 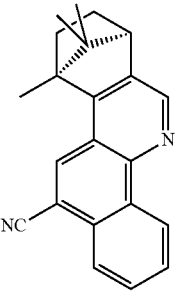 | 45% |
| L532 | S3 | S102 | 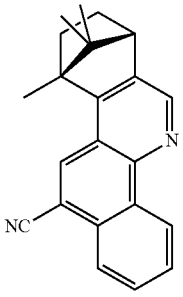 [SMILES: CC1(C)[C@@H]2CC[C@@]1(C)c1c2cnc2c1cc(C#N)c1ccccc12] | 47% |
| L533 | S4 | S102 | 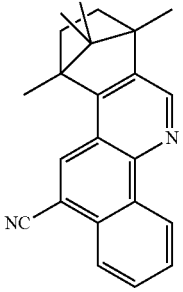 | 56% |
| L534 | S5 | S102 | 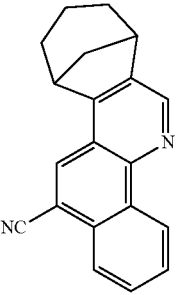 | 68% |
| L535 | S6 | S102 | 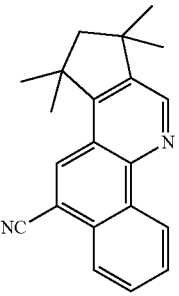 [SMILES: CC1(C)CC(C)(C)c2c1cnc1c2cc(C#N)c2ccccc21] | 72% |
-continued
| Ex. | Methylene ketone | Reactant 2 | Ligand | Yield |
|---|---|---|---|---|
| L536 | S7 | S102 | 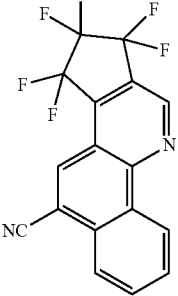 | 55% |
| L537 | S8 | S102 | 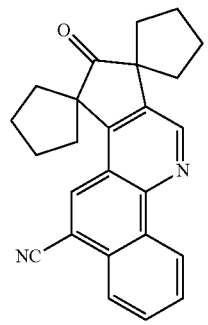 [SMILES: N#Cc1cc2c3c(cnc2c2ccccc12)C1(CCCC1)C(=O)C31CCCC1] | 56% |
| L538 | S9 | S102 | 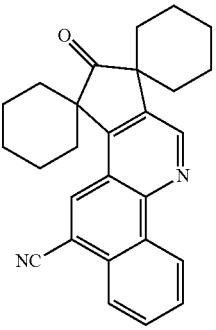 [SMILES: N#Cc1cc2c3c(cnc2c2ccccc12)C1(CCCCC1)C(=O)C31CCCCC1] | 57% |
| L539 | S10 | S102 | 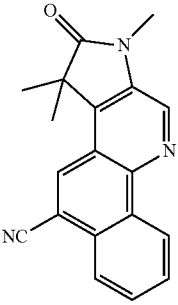 [SMILES: CN1C(=O)C(C)(C)c2c1cnc1c2cc(C#N)c2ccccc21] | 44% |

-continued

| Ex. | Methylene ketone | Reactant 2 | Ligand | Yield |
|---|---|---|---|---|
| L540 | S11 | S102 | | 36% |
| L541 | S12 | S102 | | 42% |
| L542 | S13 | S102 | | 53% |
| L543 | S14 | S102 | | 67% |
| L544 | S15 | S102 | | 67% |

-continued

| Ex. | Methylene ketone | Reactant 2 | Ligand | Yield |
|---|---|---|---|---|
| L545 | S1 | S103 | | 35% |
| L546 | S2 | S103 | | 63% |
| L547 | S3 | S103 | | 68% |
| L548 | S4 | S103 | | 64% |

| Ex. | Methylene ketone | Reactant 2 | Ligand | Yield |
|---|---|---|---|---|
| L549 | S5 | S103 | 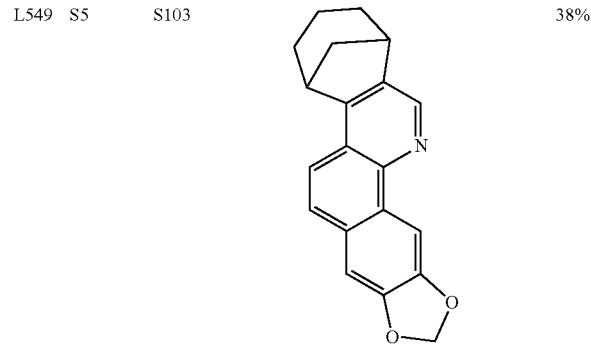 | 38% |
| L550 | S6 | S103 | 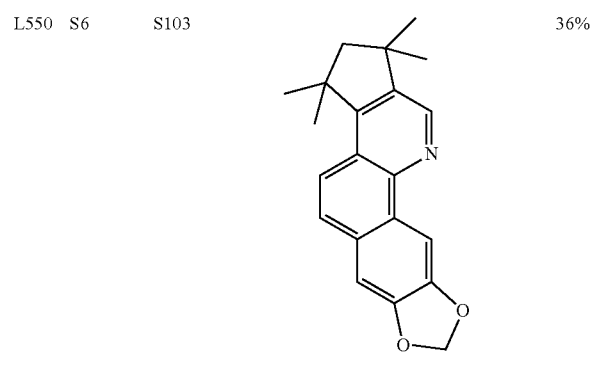 | 36% |
| L551 | S7 | S103 | 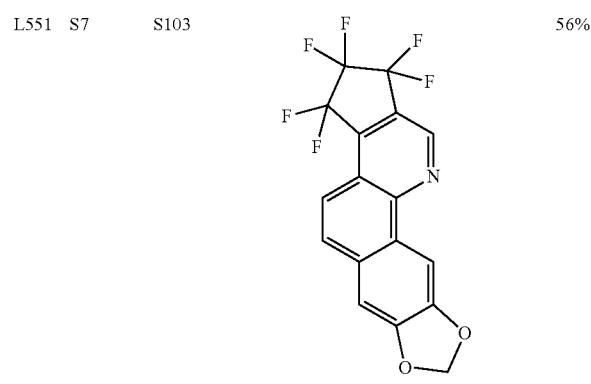 | 56% |
| L552 | S8 | S103 | 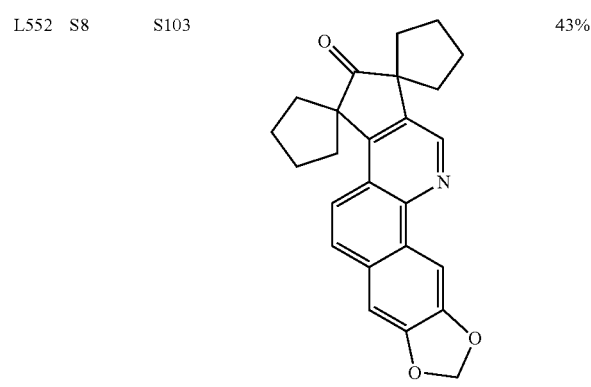 | 43% |
| L553 | S9 | S103 | 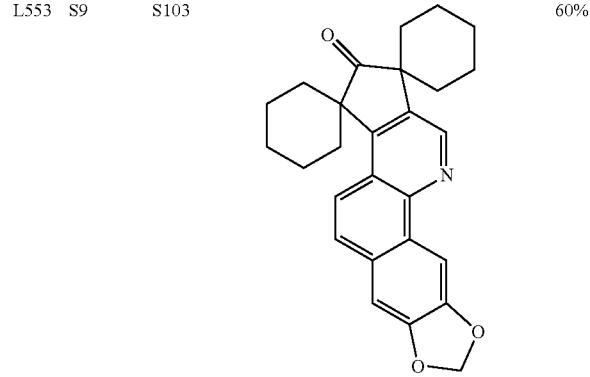 | 60% |
| L554 | S10 | S103 | 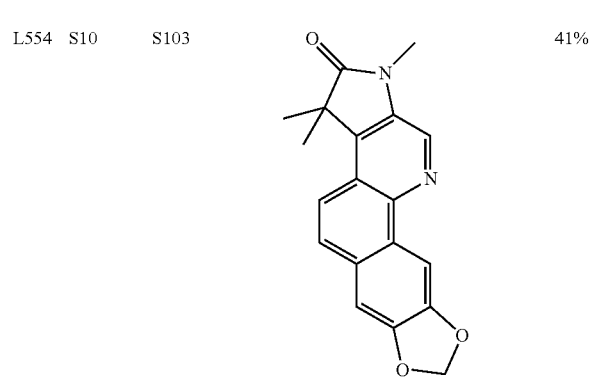 | 41% |
| L555 | S11 | S103 | 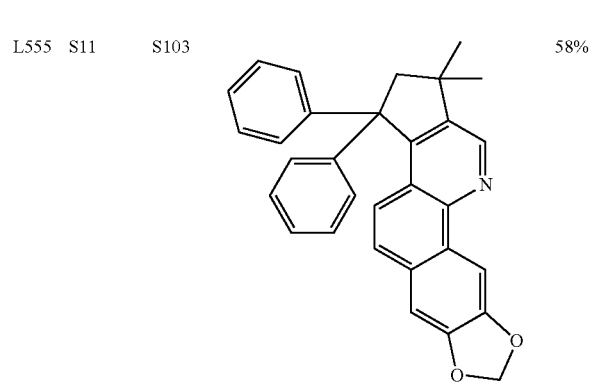 | 58% |
| L556 | S12 | S103 | 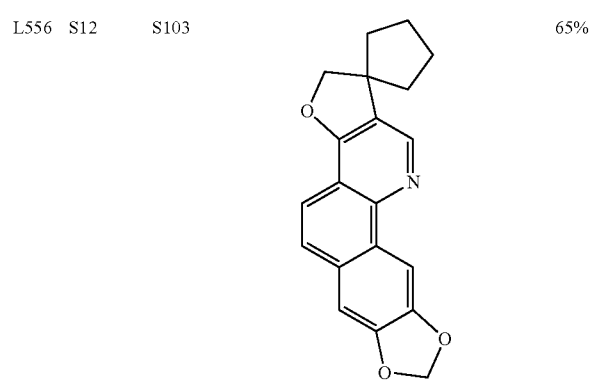 | 65% |

| Ex. | Methylene ketone | Reactant 2 | Ligand | Yield |
|---|---|---|---|---|
| L557 | S13 | S103 | 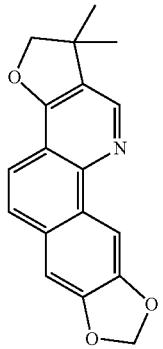 | 35% |
| L558 | S14 | S103 | 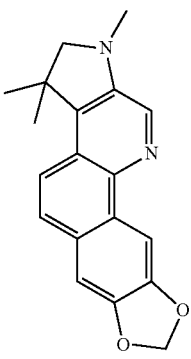 [SMILES: CN1CC(C)(C)c2c1cnc1c2ccc2cc3c(cc21)OCO3] | 38% |
| L559 | S15 | S103 | 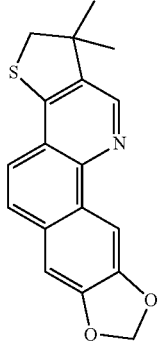 | 53% |
| L560 | S1 | S104 | 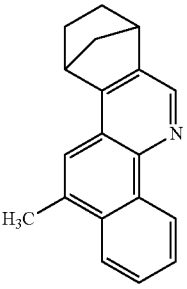 [SMILES: Cc1cc2c3c(cnc2c2ccccc12)C1CCC3C1] | 56% |
| Ex. | Methylene ketone | Reactant 2 | Ligand | Yield |
|---|---|---|---|---|
| L561 | S2 | S104 | 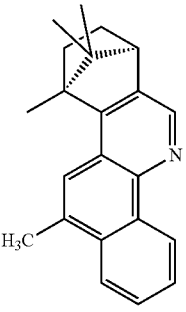 [SMILES: Cc1cc2c3c(cnc2c2ccccc12)[C@@H]1CC[C@@]3(C)C1(C)C] | 36% |
| L562 | S3 | S104 | 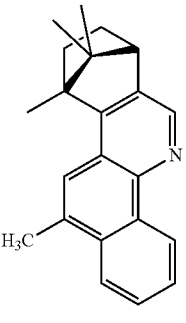 | 63% |
| L563 | S4 | S104 | 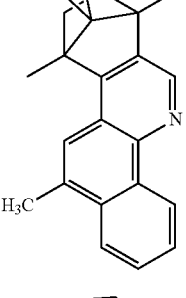 | 36% |
| L564 | S5 | S104 | 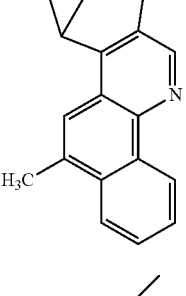 | 64% |
| L565 | S6 | S104 | | 65% |

-continued

| Ex. | Methylene ketone | Reactant 2 | Ligand | Yield |
|---|---|---|---|---|
| L566 | S7 | S104 | | 66% |
| L567 | S8 | S104 | | 58% |
| L568 | S9 | S104 | | 51% |
| L569 | S10 | S104 | | 60% |
| L570 | S11 | S104 | | 65% |
| L571 | S12 | S104 | | 55% |
| L572 | S13 | S104 | | 44% |
| L573 | S14 | S104 | | 40% |
| L574 | S15 | S104 | | 58% |

-continued
| Ex. | Methylene ketone | Reactant 2 | Ligand | Yield |
|---|---|---|---|---|
| L575 | S1 | S105 | 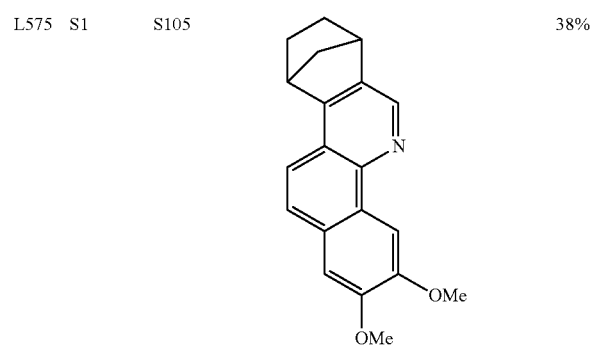 | 38% |
| L576 | S2 | S105 | 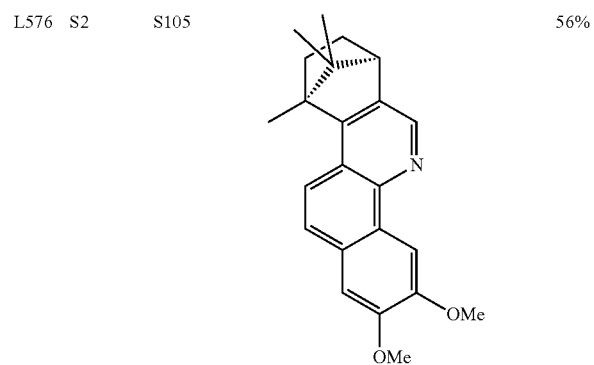 | 56% |
| L577 | S3 | S105 | 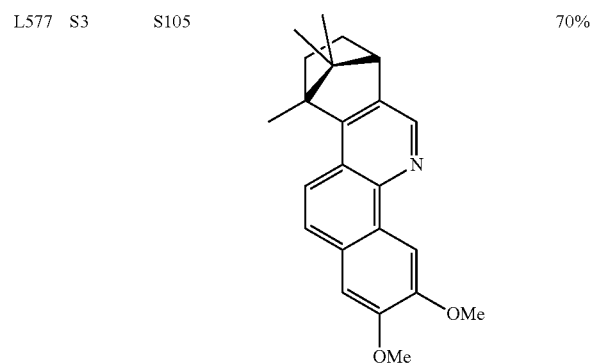 | 70% |
| L578 | S4 | S105 | 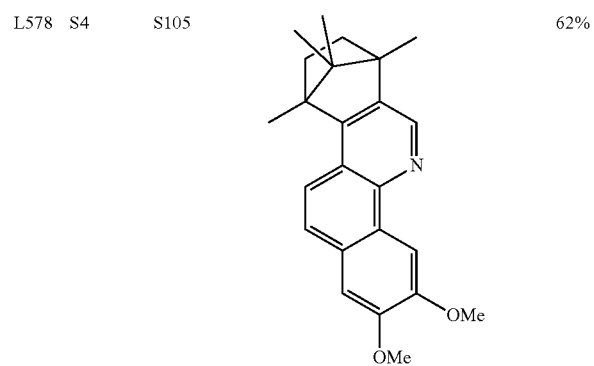 | 62% |
-continued
| Ex. | Methylene ketone | Reactant 2 | Ligand | Yield |
|---|---|---|---|---|
| L579 | S5 | S105 | 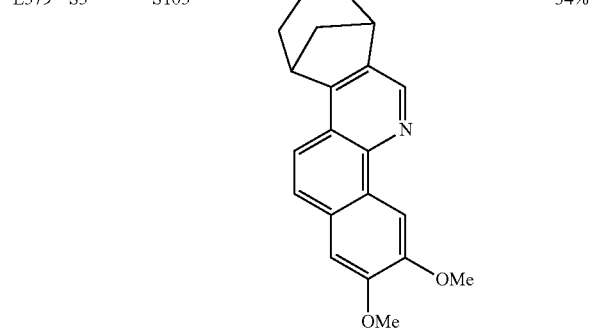 | 34% |
| L580 | S6 | S105 | 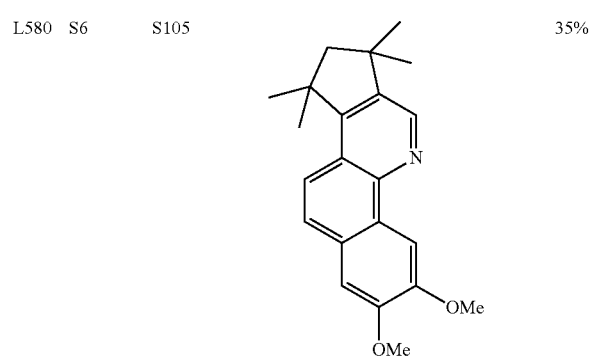 | 35% |
| L581 | S7 | S105 | 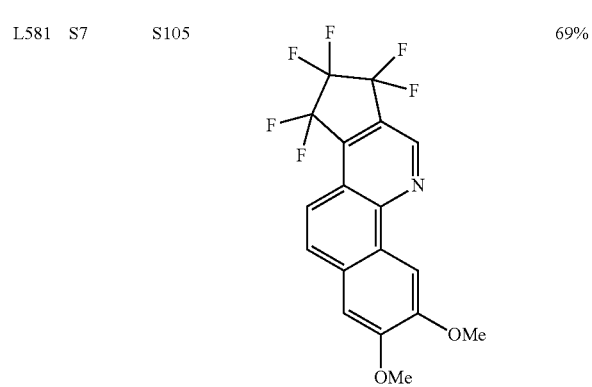 | 69% |
| L582 | S8 | S105 | 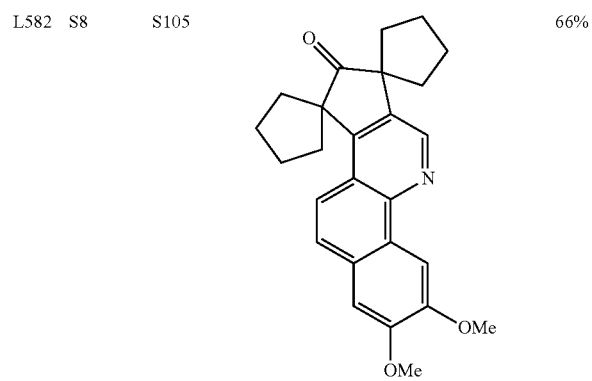 | 66% |

-continued

| Ex. | Methylene ketone | Reactant 2 | Ligand | Yield |
|---|---|---|---|---|
| L583 | S9 | S105 | (structure) | 50% |
| L584 | S10 | S105 | (structure) | 42% |
| L585 | S11 | S105 | (structure) | 60% |
| L586 | S12 | S105 | (structure) | 39% |
| L587 | S13 | S105 | (structure) | 48% |
| L588 | S14 | S105 | (structure) | 64% |
| L589 | S15 | S105 | (structure) | 49% |

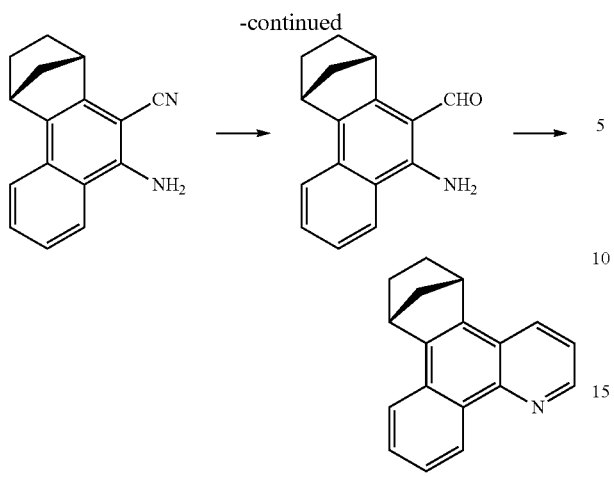

General Methods:
Step 1: Coupling of an Aliphatic Ketone with Malonitrile

The ketone (50 mmol), malonitrile (50 mmol, 1 eq), ammonium acetate (0.75 g, 10 mmol, 0.2 eq) and acetic acid (2.3 mL, 40 mmol, 0.8 eq) are initially charged, and 45 mL of anhydrous benzene are added. The reaction mixture is boiled under reflux on a water separator until no reactants are detectable any longer. After cooling, the mixture is washed with water and saturated $NaHCO_3$ solution and dried over magnesium sulfate. The benzene is drawn off under reduced pressure and the residue is recrystallized from heptane.

Example: Coupling of the Phenyl Ketone with Malonitrile

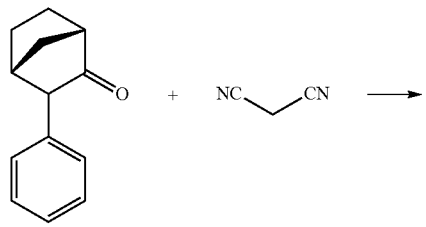

7485-53-2    109-77-3

(1S,4R)-3-Phenylbicyclo[2.2.1]heptan-2-one (9.3 g, 50 mmol), malonitrile (3.3 g, 50 mmol), ammonium acetate (0.75 g, 10 mmol) and acetic acid (2.3 mL, 40 mmol) are initially charged, and 45 mL of anhydrous benzene are added. The reaction mixture is boiled reflux on a water separator for 4 h. After cooling, the mixture is washed with water and saturated $NaHCO_3$ solution and dried over magnesium sulfate. The benzene is drawn off under reduced pressure and the residue is recrystallized from heptane. 5.8 g (40 mmol, 81%) of a colorless solid are obtained.

Step 2: Cyclization

The reactant (35 mmol) is dissolved gradually in concentrated sulfuric acid (25 mL) at 5° C. and stirred at room temperature overnight. The reaction mixture is added to ice and the precipitated solid is filtered off, washed with water and dried. The product is recrystallized repeatedly from methanol.

Example: Cyclization

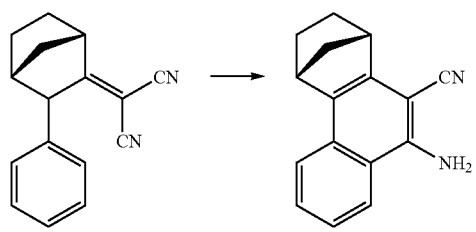 [SMILES: N#CC(C#N)=C1C(c2ccccc2)[C@@H]2CC[C@H]1C2 ; N#Cc1c2c(c3ccccc3c1N)[C@@H]1CC[C@H]2C1]

The reactant (5 g, 35 mmol) is dissolved gradually in concentrated sulfuric acid (25 mL) at 5° C. and stirred at room temperature overnight. The reaction mixture is added to ice and the precipitated solid is filtered off, washed with water and dried. The product is recrystallized repeatedly from methanol. 3.5 g (14 mmol, 40%) of the product are obtained.

Step 3: Reduction of the o-Aminonitrile to o-Aminocarbaldehyde

The ortho-aminonitrile (10 mmol) is dissolved in 25 mL of anhydrous dichloromethane and cooled to 0° C. A 1 M solution of DIBAL-H in toluene (15 mmol, 1.5 eq) is slowly added dropwise and the solution is stirred at room temperature for 24 h. The reaction mixture is diluted with anhydrous diethyl ether and cooled to 0° C. 0.6 mL of water, then 0.6 mL of a 15% aqueous NaOH solution, then another 1.5 mL of water are gradually and cautiously added dropwise, and the solution is stirred for 15 minutes. Anhydrous magnesium sulfate is added, and the mixture is stirred for a further 15 minutes and filtered. The solvents are removed under reduced pressure and the crude product is purified by column chromatography with a mixture of dichloromethane/heptane.

Example: Hydrolysis

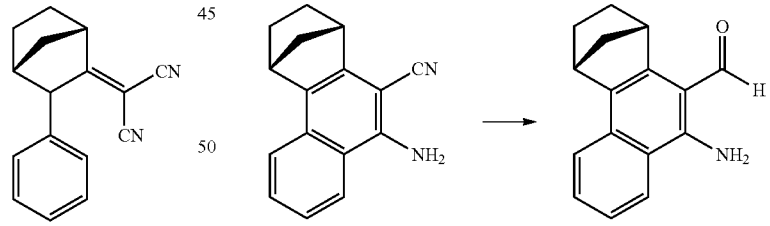

The ortho-aminonitrile (2.34 g, 10 mmol) is dissolved in 25 mL of anhydrous dichloromethane and cooled to 0° C. A 1 M solution of DIBAL-H in toluene (15 mL, 15 mmol, 1.5 eq) is slowly added dropwise and the solution is stirred at room temperature for 24 h. The reaction mixture is diluted with anhydrous diethyl ether and cooled to 0° C. 0.6 mL of water, then 0.6 mL of a 15% aqueous NaOH solution, then another 1.5 mL of water are gradually and cautiously added dropwise, and the solution is stirred for 15 minutes. Anhydrous magnesium sulfate is added, and the mixture is stirred for a further 15 minutes and filtered. The solvents are removed under reduced pressure and the crude product is purified by column chromatography with a mixture of dichloromethane/heptane (1:1). A colorless solid is obtained in 67% yield (1.69 g, 6.7 mmol).

Step 4: Conversion of the Ortho-aminocarbaldehyde to the 5,6-substituted Benzo[h]Quinoline To an initial charge of the o-aminocarbaldehyde (4 mmol) and acetaldehyde (4 mmol, 1 eq) are added 15 mL of dry ethanol. Pulverulent potassium hydroxide (4.8 mmol, 1.2 eq) are added gradually and the reaction mixture is stirred under reflux for 24 h. On completion of conversion, the solution is cooled down, dichloromethane is added and the mixture is filtered through Celite. The organic phase is washed with water, dried over magnesium sulfate and freed of the solvent under reduced pressure. The product is purified by column chromatography.

Example: Cyclization to Give L1000

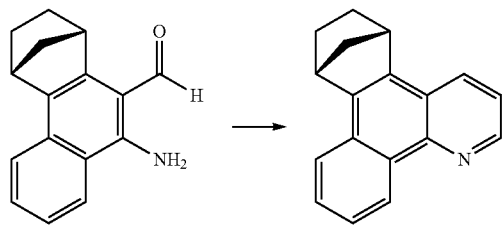 [SMILES: Nc1c(C=O)c2c(c3ccccc13)[C@@H]1CC[C@H]2C1 ; c1ccc2c(c1)c1c(c3cccnc32)[C@H]2CC[C@@H]1C2]

To an initial charge of the o-aminocarbaldehyde (1 g, 4 mmol) and acetaldehyde (177 mg, 0.225 mL, 4 mmol) are added 15 mL of dry ethanol. Pulverulent potassium hydroxide (0.27 g, 4.8 mmol, 1.2 eq) are added gradually and the reaction mixture is stirred under reflux for 24 h. On completion of conversion, the solution is cooled down and dichloromethane is added and the mixture is filtered through Celite. The organic phase is washed with water, dried over magnesium sulfate and freed of the solvent under reduced pressure. The product is purified by column chromatography and gives 0.71 g (2.9 mmol, 74%) of a colorless solid.

By conducting the general methods, it is possible to prepare the following ligands:

| Ex. | Ketone | Ligand | Yield over 4 stages |
|---|---|---|---|
| L1000 | (10472-46-5) | | 8.4% |
| L1001 | (68146-12-3) | | 9.3% |
| L1002 | (30557-98-3) | | 7.9% |

7,8-substituted benzo[h]quinolines

Reaction Scheme:

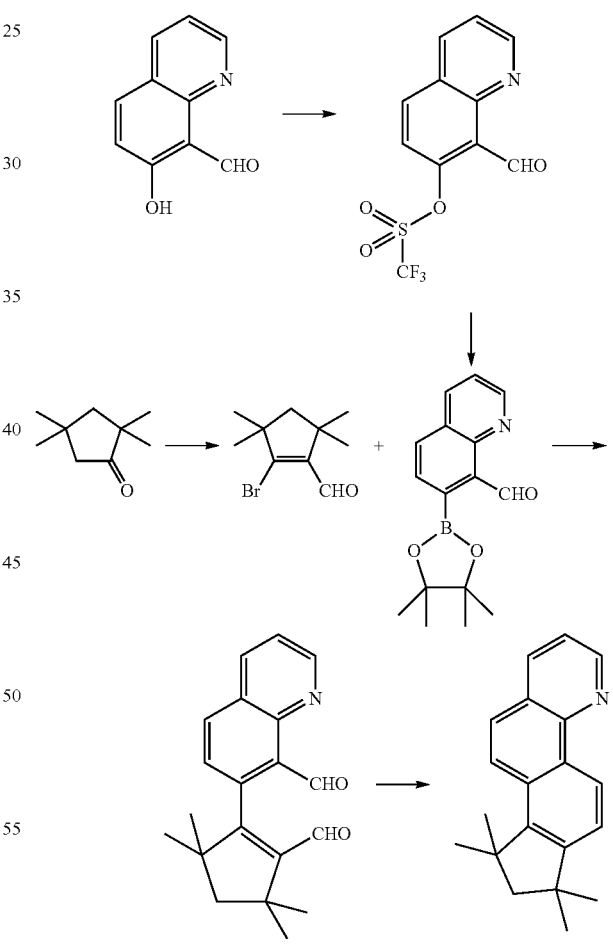

Synthesis Methods:
General Method: Conversion of an o-phenol Carbaldehyde to an o-trifluoromethanesulfonic Acid Carbaldehyde The hydroxyquinolinecarbaldehyde (50 mmol) is dissolved in 25 mL of dichloromethane and cooled to 0° C. A solution, cooled to 0° C., of pyridine (12.6 mL, 75 mmol, 1.5 eq) and trifluoromethanesulfonic anhydride (8.1 mL, 100 mmol, 2 eq) is slowly added dropwise within 15 minutes and the reaction mixture is stirred at room temperature for 12-24 h. The reaction is stopped by adding 60 mL of water and the organic phase is removed. The aqueous phase is extracted repeatedly with diethyl ether and the combined organic phases are dried over magnesium sulfate. The solvent is removed under reduced pressure and the residue is purified by column chromatography.
Example:

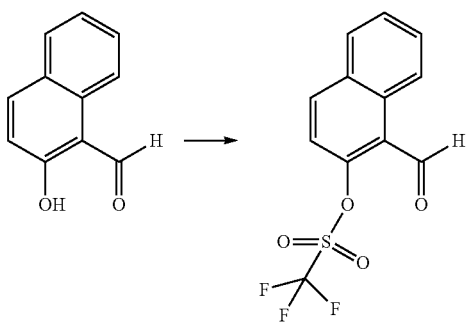 [SMILES: O=Cc1c(O)ccc2ccccc12 ; O=Cc1c(OS(=O)(=O)C(F)(F)F)ccc2ccccc12]

The 2-hydroxynaphthalenecarbaldehyde (8.61 g, 50 mmol) is dissolved in 25 mL of dichloromethane and cooled to 0° C. A solution, cooled to 0° C., of pyridine (12.6 mL, 75 mmol, 1.5 eq) and trifluoromethanesulfonic anhydride (8.1 mL, 100 mmol, 2 eq) is slowly added dropwise within 15 minutes and the reaction mixture is stirred at room temperature for 24 h. The reaction is stopped by adding 60 mL of water and the organic phase is removed. The aqueous phase is extracted repeatedly with diethyl ether and the combined organic phases are dried over magnesium sulfate. The solvent is removed under reduced pressure and the residue is purified by column chromatography. 11.4 g (75%, 37.5 mmol) of a colorless oil is obtained.
Step 2: Conversion of the o-trifluoromethanesulfonic Acid Carbaldehyde to a Pinacolboranecarbaldehyde A mixture of PdCl$_2$(dppf)$_2$ (220 mg, 0.3 mmol, 0.03 eq), the trifluoromethanesulfonic acid carbaldehyde (10 mmol), triethylamine (4.2 mL, 30 mmol) and pinacolborane (2.2 mL, 15 mmol) is carefully inertized and dissolved in 40 mL of dioxane. The reaction mixture is heated to 80° C. for 3-12 h, cooled down, diluted with water and extracted with toluene. The organic phases are washed with water and saturated NaCl solution, dried over magnesium sulfate and freed of the solvent under reduced pressure. The residue is purified by column chromatography.
Example:

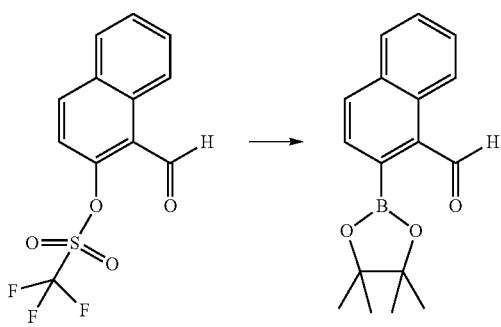 [SMILES: O=Cc1c(OS(=O)(=O)C(F)(F)F)ccc2ccccc12 ; CC1(C)OB(c2ccc3ccccc3c2C=O)OC1(C)C]

A mixture of PdCl$_2$(dppf)$_2$ (220 mg, 0.3 mmol, 0.03 eq), 2-trifluoromethanesulfonylnaphthalenecarbaldehyde (2.48 g, 10 mmol), triethylamine (4.2 mL, 30 mmol) and pinacolborane (2.2 mL, 15 mmol) is carefully inertized and dissolved in 40 mL of dioxane. The reaction mixture is heated to 80° C. for 12 h, cooled down, diluted with water and extracted with toluene. The organic phases are washed with water and saturated NaCl solution, dried over magnesium sulfate and freed of the solvent under reduced pressure. The residue is purified by column chromatography (EA/heptane 1:10), and 1.84 g (65%, 6.5 mmol) of a colorless oil are obtained.
Step 3: Coupling of the pinacolboranecarbaldehyde with the bromoalkenecarbaldehyde 5.5 mmol of the bromoalkenecarbaldehyde, 5.5 mmol (1 eq) of pinacolboranecarbaldehyde and 10.5 mmol (1.9 eq) of potassium phosphate are initially charged, suspended in 25 mL of toluene, 25 mL of dioxane and 25 mL of water, and inertized. Added to this suspension are 45 mg of tri-o-tolylphosphine (0.15 mmol) and then 6 mg of palladium(II) acetate (0.025 mmol), and the reaction mixture is heated under reflux for 24 h. After cooling, the reaction mixture is diluted with toluene, and the organic phases are removed, washed with water, filtered through silica gel and dried over magnesium sulfate. The solvent is removed under reduced pressure. The residue is purified by column chromatography.
Example:

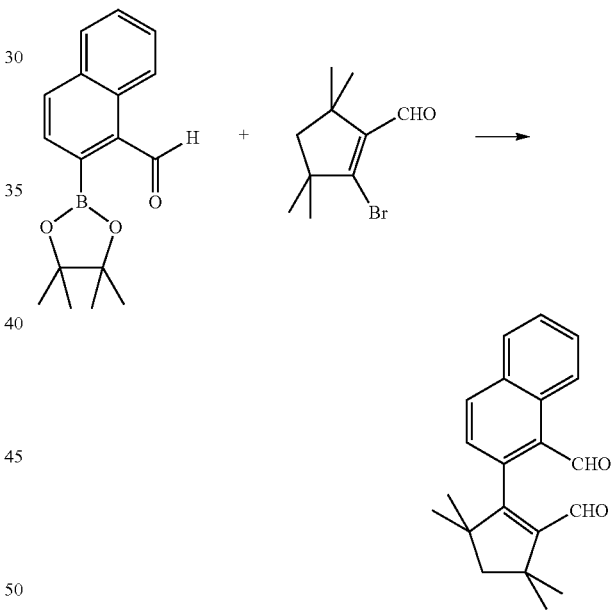

1.27 g (5.5 mmol) of the bromoalkenecarbaldehyde S6, 1.55 g (5.5 mmol, 1 eq) of pinacolboranecarbaldehyde and 2.23 g (10.5 mmol, 1.9 eq) of potassium phosphate are initially charged, suspended in 25 mL of toluene, 25 mL of dioxane and 25 mL of water, and inertized. Added to this suspension are 45 mg (0.15 mmol) of tri-o-tolylphosphine and then 6 mg (0.025 mmol) of palladium(II) acetate, and the reaction mixture is heated under reflux for 24 h. After cooling, the reaction mixture is diluted with toluene, and the organic phases are removed, washed with water, filtered through silica gel and dried over magnesium sulfate. The toluene is removed under reduced pressure. The residue is separated by column chromatography (ethyl acetate/heptane 1:9), and 1.52 g (4.95 mmol, 95%) of a colorless solid are obtained.

Step 4: McMurry Coupling of the Biscarbaldehyde

To a suspension of activated zinc dust (3.2 g, 49 mmol) in 60 mL of THF which has been cooled to 0° C. and inertized are slowly added dropwise 3 mL (27.4 mmol) of TiCl$_4$. The suspension is heated under reflux for 2 h and cooled to 0° C., and a solution of the bisaldehyde (5.3 mmol) in 20 mL of THF is added dropwise within 30 minutes. The reaction mixture is gradually warmed up to room temperature, then heated under reflux for two hours. After cooling, the solution is poured into a saturated potassium carbonate solution which has been cooled to 0° C. and extracted with dichloromethane. The organic phases are combined and washed with water and saturated NaCl solution. The mixture is dried over sodium sulfate, the solvent is removed under reduced pressure and purification is effected by column chromatography.

Example L1500:

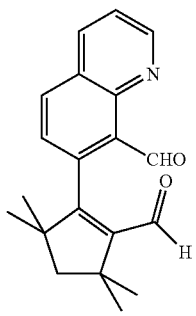  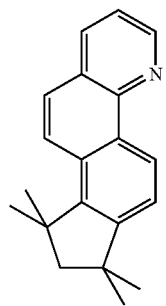

To a suspension of activated zinc dust (3.2 g, 49 mmol) in 60 mL of THF which has been cooled to 0° C. and inertized are slowly added dropwise 3 mL (27.4 mmol) of TiCl$_4$. The suspension is heated under reflux for 2 h and cooled to 0° C., and a solution of the bisaldehyde (1.63 g, 5.3 mmol) in 20 mL of THF is added dropwise within 30 minutes. The reaction mixture is gradually warmed up to room temperature, then boiled under reflux for two hours. After cooling, the solution is poured into a saturated potassium carbonate solution which has been cooled to 0° C. and extracted with dichloromethane. The organic phases are combined and washed with water and saturated NaCl solution. The mixture is dried over sodium sulfate, the solvent is removed under reduced pressure, purification is effected by column chromatography (silica gel, ethyl acetate/heptane 1:5) and 1.13 g (4.09 mmol, 73%) of a colorless solid are obtained.

By coupling the synthons S1-S15 with 7-(4,4,5,5-tetramethyl-[1,3,2]dioxaborolan-2-yl)quinoline-8-carbaldehyde, it is possible to obtain the following ligands:

| Ex. | Bromoalkene-carbaldehyde | Ligand | Yield over 4 stages |
|---|---|---|---|
| L1500 | S6 | | 55% |
| L1501 | S1 | | 47% |
| L1502 | S2 | | 48% |
| L1503 | S3 | | 40% |
| L1504 | S4 | | 54% |
| L1505 | S5 | | 40% |

| Ex. | Bromoalkene-carbaldehyde | Ligand | Yield over 4 stages |
|---|---|---|---|
| L1506 | S7 | | 55% |
| L1507 | S11 | | 50% |
| L1508 | S12 | | 57% |
| L1509 | S13 | | 40% |
| L1510 | S14 | | 51% |
| L1511 | S15 | | 45% |

Synthesis of the Metal Complexes

1) Homoleptic Tris-facial Iridium Complexes:

Variant A: Trisacetylacetonatoiridium(III) as Iridium Reactant

A mixture of 10 mmol of trisacetylacetonatoiridium(III) [15635-87-7], 40-60 mmol of the ligand L, optionally 1 g of an inert high-boiling additive as melting aid or solvent, for example hexadecane, m-terphenyl, triphenylene, diphenyl ether, 3-phenoxytoluene, 1,2-, 1,3-, 1,4-bisphenoxybenzene, triphenylphosphine oxide, sulfolane, 18-crown-6, triethylene glycol, glycerol, polyethylene glycols, phenol, 1-naphthol, etc., and a glass-ensheathed magnetic stirrer bar are sealed by melting under reduced pressure ($10^{-5}$ mbar) into a thick-wall 50 mL glass ampoule. The ampoule is heated at the temperature specified for the time specified, in the course of which the molten mixture is stirred with the aid of a magnetic stirrer bar. In order to prevent sublimation of the ligands at colder points in the ampoule, the whole ampoule has to have the temperature specified. Alternatively, the synthesis can be effected in a stirred autoclave with a glass insert. After cooling (CAUTION: the ampoules are usually under pressure!), the ampoule is opened, the sinter cake is stirred with 100 g of glass beads (diameter 3 mm) in 100 mL of a suspension medium (the suspension medium is chosen such that the ligand has good solubility but the metal complex has sparing solubility therein; typical suspension media are methanol, ethanol, dichloromethane, acetone, THF, ethyl acetate, toluene, etc.) for 3 h and mechanically digested in the process. The fine suspension is decanted off from the glass beads, and the solids are filtered off with suction, washed with 50 mL of the suspension medium and dried under reduced pressure. The dry solid is placed in a continuous hot extractor on an Alox bed of height 3-5 cm (Alox, basic, activity level 1) and then extracted with an extractant (initial charge of about 500 mL; the extractant is chosen such that the complex has good solubility in the hot extractant and sparing solubility in the cold extractant; particularly suitable extractants are hydrocarbons such as toluene, xylenes, mesitylene, naphthylene, o-dichlorobenzene, tetrahydrofuran, dichloromethane, 1,2-dichloroethane, 1,1,2,2-tetrachloroethane, chloroform, carbon tetrachloride). After the extraction has ended, the extractant is concentrated under reduced pressure to about 100 mL. Metal complexes having too good a solubility in the extractant are made to crystallize by dropwise addition of 200 mL of methanol. The solid from the suspension thus obtained is filtered off with suction, washed once with about 50 mL of methanol and dried. After drying, the purity of the metal complex is determined by means of NMR and/or HPLC. If the purity is below 99.5%, the hot extraction step is repeated, omitting the Alox bed from the 2nd extraction onward. Once the purity of 99.5%-99.9% has been attained, the metal complex is heat-treated or sublimed. The heat treatment is effected under high vacuum (p about $10^{-6}$ mbar) within the temperature range of about 200-300° C. The sublimation is effected under high vacuum (p about $10^{-6}$ mbar) within the temperature range of about 230-400° C., the sublimation preferably being conducted in the form of a fractional sublimation. Complexes having good solubility in organic solvents can alternatively also be chromatographed on silica gel.

If ligands of the C1 point group are used in racemic form, the fac metal complexes derived are obtained as a diastereomer mixture. The enantiomer pair of the C3 point group generally has much lower solubility in the extractant than that of the C1 point group, which consequently accumulates in the mother liquor. Separation of the diastereomers in this way is frequently possible. In addition, the diastereomers can also be separated by chromatography. If the ligands of the C1 point group are used in enantiomerically pure form, the Δ-Λ-diastereomer pair of the C3 point group forms.

Variant B: Tris(2,2,6,6-tetramethyl-3,5-heptanedionato)iridium(III) as iridium reactant Procedure analogous to variant A, except using 10 mmol of tris(2,2,6,6-tetramethyl-3,5-heptanedionato)iridium [99581-86-9] in place of 10 mmol of trisacetylacetonatoiridium(III) [15635-87-7]. The use of this reactant is advantageous since the purity of the crude product obtained is frequently better than in variant A. In addition, the pressure buildup in the ampoule is frequently not as significant.

Variant C: Sodium [cis,trans-dichloro(bisacetylacetonato]irdate(III) as iridium reactant A mixture of 10 mmol of sodium [cis,trans-dichloro(bisacetylacetonato]iridate(II) [876296-21-8] and 60 mmol of the ligand in 50 mL of ethylene glycol, propylene glycol or diethylene glycol is heated under gentle reflux under a gentle argon stream for the time specified. After cooling to 60° C., the mixture is diluted while stirring with a mixture of 50 mL of ethanol and 50 mL of 2 N hydrochloric acid and stirred for a further 1 h, and the precipitated solids are filtered off, washed three times with 30 mL each time of ethanol and then dried under reduced pressure. Purification by hot extraction or chromatography and fractional sublimation as described in A.

| Ex. | Ligand | Ir complex Diastereomer | Variant Reaction medium Reaction temperature Reaction time Susp. medium Extractant | Yield % |
|---|---|---|---|---|
| Ir(L1)$_3$ | L1 | 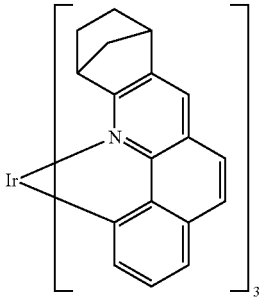 | A — 270° C. 48 h acetone o-xylene | 35 |
| Ir(L2)$_3$ | L2 | Ir(L2)$_3$ | as Ir(L1)$_3$ | 12 |
| Ir(L8)$_3$ | L8 | 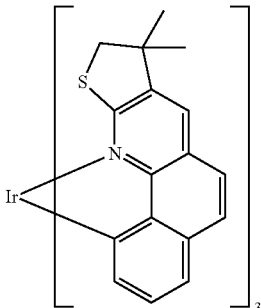 | A — 260° C. 48 h ethanol o-xylene | 34 |

-continued

| Ex. | Ligand | Ir complex Diastereomer | Variant Reaction medium Reaction temperature Reaction time Susp. medium Extractant | Yield % |
|---|---|---|---|---|
| Ir(L9)₃ | L9 | | A — 290° C. 48 h ethyl acetate o-xylene | 14 |
| Ir(L10)₃ | L10 | Ir(L10)₃ | as Ir(L9)₃ | 32 |
| Ir(L16)₃ | L16 | | C — 320° C. 48 h ethanol o-xylene | 27 |
| Ir(L17)₃ | L17 | | A — 300° C. 36 h ethanol o-xylene | 33 |

-continued

| Ex. | Ligand | Ir complex Diastereomer | Variant Reaction medium Reaction temperature Reaction time Susp. medium Extractant | Yield % |
|---|---|---|---|---|
| Ir(L18)$_3$ | L18 | | A — 280° C. ethyl acetate o-xylene | 24 |
| Ir(L19)$_3$ | L19 | | A — 290° C. 60 h ethyl acetate o-xylene | 27 |
| Ir(L25)$_3$ | L25 | | A — 260° C. 24 h ethyl acetate o-xylene | 32 |
| Ir(L26)$_3$ | L26 | | A — 290° C. 48 h ethyl acetate o-xylene | 27 |

-continued

| Ex. | Ligand | Ir complex Diastereomer | Variant Reaction medium Reaction temperature Reaction time Susp. medium Extractant | Yield % |
|---|---|---|---|---|
| Ir(L27)$_3$ | L27 | | A — 290° C. 24 h methanol o-xylene | 25 |
| Ir(L28)$_3$ | L28 | | A — 260° C. 60 h ethanol o-xylene | 27 |
| Ir(L29)$_3$ | L29 | | C — 280° C. 60 h ethanol o-xylene | 34 |
| Ir(L35)$_3$ | L35 | | C — 260° C. 48 h ethanol o-xylene | 20 |

-continued

| Ex. | Ligand | Ir complex Diastereomer | Variant Reaction medium Reaction temperature Reaction time Susp. medium Extractant | Yield % |
|---|---|---|---|---|
| Ir(L36)$_3$ | L36 | | C<br>—<br>260° C.<br>48 h<br>ethanol<br>o-xylene | 23 |
| Ir(L500)$_3$ | L500 | | A<br>—<br>260° C.<br>24 h<br>ethyl acetate<br>o-xylene | 24 |
| Ir(L501)$_3$ | L501 | | A<br>—<br>280° C.<br>24 h<br>ethyl acetate<br>o-xylene | 33 |
| Ir(L502)$_3$ | L502 | | A<br>—<br>280° C.<br>24 h<br>ethyl acetate<br>o-xylene | 22 |

-continued

| Ex. | Ligand | Ir complex Diastereomer | Variant Reaction medium Reaction temperature Reaction time Susp. medium Extractant | Yield % |
|---|---|---|---|---|
| Ir(L503)$_3$ | L503 | | A — 280° C. 24 h ethanol o-xylene | 27 |
| Ir(L504)$_3$ | L504 | | A — 280° C. 24 h ethanol o-xylene | 28 |
| Ir(L505)$_3$ | L505 | | A — 260° C. 24 h ethanol o-xylene | 28 |
| Ir(L506)$_3$ | L506 | | A — 300° C. 48 h ethyl acetate o-xylene | 12 |

-continued

| Ex. | Ligand | Ir complex Diastereomer | Variant Reaction medium Reaction temperature Reaction time Susp. medium Extractant | Yield % |
|---|---|---|---|---|
| Ir(L507)$_3$ | L507 | | B — 300° C. 48 h ethyl acetate o-xylene | 9 |
| Ir(L508)$_3$ | L508 | | B — 300° C. 48 h ethyl acetate o-xylene | 10 |
| Ir(L509)$_3$ | L509 | | A — 280° C. 24 h ethyl acetate o-xylene | 37 |
| Ir(L510)$_3$ | L510 | | B — 300° C. 24 h ethyl acetate o-xylene | 10 |

-continued

| Ex. | Ligand | Ir complex Diastereomer | Variant Reaction medium Reaction temperature Reaction time Susp. medium Extractant | Yield % |
|---|---|---|---|---|
| Ir(L511)₃ | L511 | | A — 260° C. 24 h ethyl acetate o-xylene | 22 |
| Ir(L512)₃ | L512 | | A — 260° C. 24 h ethyl acetate o-xylene | 27 |
| Ir(L513)₃ | L513 | | A — 280° C. 24 h ethyl acetate o-xylene | 25 |
| Ir(L514)₃ | L514 | | A — 260° C. 24 h ethyl acetate o-xylene | 25 |

-continued
| Ex. | Ligand | Ir complex Diastereomer | Variant Reaction medium Reaction temperature Reaction time Susp. medium Extractant | Yield % |
|---|---|---|---|---|
| Ir(L515)₃ | L515 | 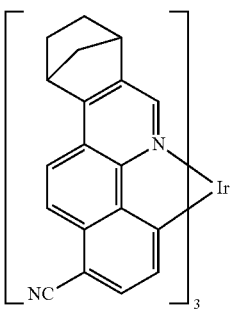 | C — 280° C. 24 h ethyl acetate o-xylene | 31 |
| Ir(L516)₃ | L516 | 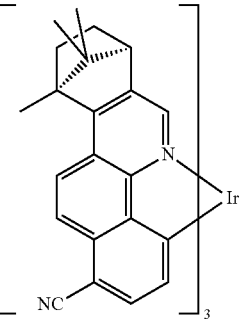 | C — 280° C. 24 h ethyl acetate o-xylene | 29 |
| Ir(L517)₃ | L517 | 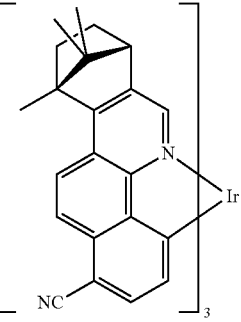 | C — 280° C. 24 h ethyl acetate o-xylene | 30 |
| Ir(L518)₃ | L518 | 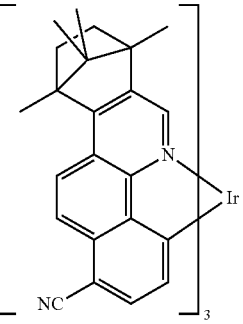 | C — 280° C. 24 h ethyl acetate o-xylene | 24 |

-continued

| Ex. | Ligand | Ir complex Diastereomer | Variant Reaction medium Reaction temperature Reaction time Susp. medium Extractant | Yield % |
|---|---|---|---|---|
| Ir(L519)₃ | L519 | | C — 280° C. 24 h ethyl acetate o-xylene | 27 |
| Ir(L520)₃ | L520 | | C — 280° C. 24 h ethyl acetate o-xylene | 26 |
| Ir(L521)₃ | L521 | | C — 280° C. 36 h ethyl acetate o-xylene | 12 |
| Ir(L522)₃ | L522 | | C — 300° C. 36 h ethyl acetate o-xylene | 11 |

-continued

| Ex. | Ligand | Ir complex Diastereomer | Variant Reaction medium Reaction temperature Reaction time Susp. medium Extractant | Yield % |
|---|---|---|---|---|
| Ir(L523)$_3$ | L523 | | C — 320° C. 36 h ethyl acetate o-xylene | 8 |
| Ir(L524)$_3$ | L524 | | C — 280° C. 24 h ethyl acetate o-xylene | 23 |
| Ir(L525)$_3$ | L525 | | C — 300° C. 24 h ethyl acetate o-xylene | 11 |
| Ir(L526)$_3$ | L526 | | C — 300° C. 24 h ethyl acetate o-xylene | 22 |

-continued

| Ex. | Ligand | Ir complex Diastereomer | Variant Reaction medium Reaction temperature Reaction time Susp. medium Extractant | Yield % |
|---|---|---|---|---|
| Ir(L527)₃ | L527 | | C — 280° C. 24 h ethyl acetate o-xylene | 27 |
| Ir(L528)₃ | L528 | | C — 280° C. 24 h ethyl acetate o-xylene | 30 |
| Ir(L529)₃ | L529 | | C — 280° C. 24 h ethyl acetate o-xylene | 26 |
| Ir(L530)₃ | L530 | | A — 280° C. 24 h ethyl acetate o-xylene | 22 |

-continued

| Ex. | Ligand | Ir complex Diastereomer | Variant Reaction medium Reaction temperature Reaction time Susp. medium Extractant | Yield % |
|---|---|---|---|---|
| Ir(L531)$_3$ | L531 | | A — 280° C. 24 h ethyl acetate o-xylene | 27 |
| Ir(L532)$_3$ | L532 | | A — 280° C. 24 h ethyl acetate o-xylene | 29 |
| Ir(L533)$_3$ | L533 | | A — 280° C. 24 h ethyl acetate o-xylene | 32 |
| Ir(L534)$_3$ | L534 | | A — 280° C. 24 h ethyl acetate o-xylene | 30 |

| Ex. | Ligand | Ir complex Diastereomer | Variant Reaction medium Reaction temperature Reaction time Susp. medium Extractant | Yield % |
|---|---|---|---|---|
| Ir(L535)$_3$ | L535 | 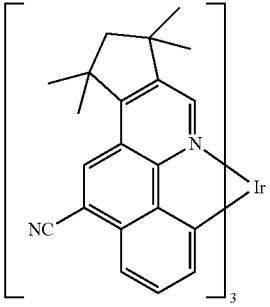 | A — 260° C. 24 h ethyl acetate o-xylene | 27 |
| Ir(L536)$_3$ | L536 | 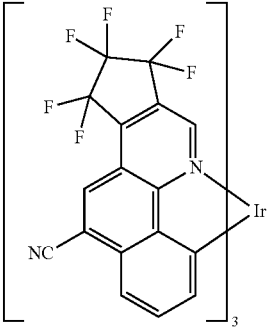 | C — 300° C. 36 h ethyl acetate o-xylene | 15 |
| Ir(L537)$_3$ | L537 | 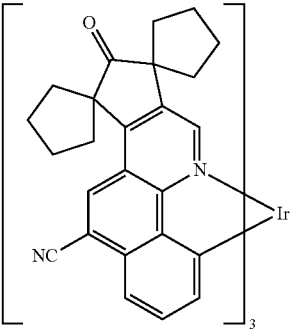 | B — 300° C. 36 h ethyl acetate o-xylene | 12 |
| Ir(L538)$_3$ | L538 | 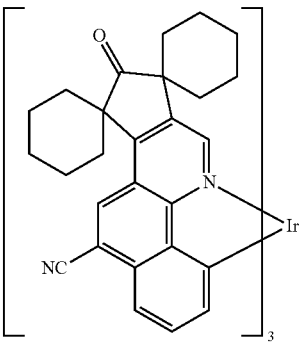 | B — 300° C. 36 h ethyl acetate o-xylene | 14 |

-continued

| Ex. | Ligand | Ir complex Diastereomer | Variant Reaction medium Reaction temperature Reaction time Susp. medium Extractant | Yield % |
|---|---|---|---|---|
| Ir(L539)₃ | L539 | | C — 260° C. 24 h ethyl acetate o-xylene | 27 |
| Ir(L540)₃ | L540 | | B — 300° C. 24 h ethyl acetate o-xylene | 14 |
| Ir(L541)₃ | L541 | | C — 280° C. 24 h ethyl acetate o-xylene | 22 |
| Ir(L542)₃ | L542 | | C — 280° C. 24 h ethyl acetate o-xylene | 29 |

-continued
| Ex. | Ligand | Ir complex Diastereomer | Variant Reaction medium Reaction temperature Reaction time Susp. medium Extractant | Yield % |
|---|---|---|---|---|
| Ir(L543)₃ | L543 | 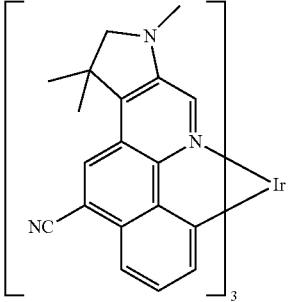 | C — 280° C. 24 h ethyl acetate o-xylene | 32 |
| Ir(L544)₃ | L544 | 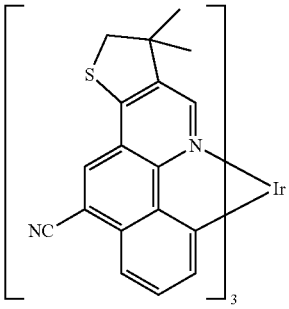 | C — 280° C. 24 h ethyl acetate o-xylene | 34 |
| Ir(L545)₃ | L545 | 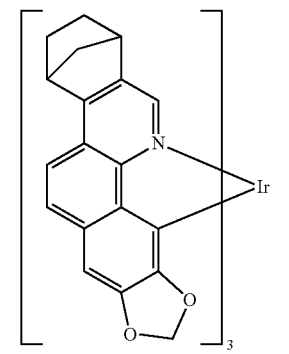 | A — 280° C. 24 h ethanol o-xylene | 28 |
| Ir(L546)₃ | L546 | 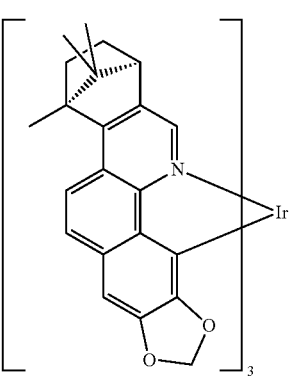 | A — 280° C. 24 h ethanol o-xylene | 26 |

-continued

| Ex. | Ligand | Ir complex Diastereomer | Variant Reaction medium Reaction temperature Reaction time Susp. medium Extractant | Yield % |
|---|---|---|---|---|
| Ir(L547)₃ | L547 | | A — 280° C. 24 h ethanol o-xylene | 27 |
| Ir(L548)₃ | L548 | | A — 280° C. 24 h ethanol o-xylene | 24 |
| Ir(L549)₃ | L549 | | A — 280° C. 24 h ethanol o-xylene | 26 |

-continued

| Ex. | Ligand | Ir complex Diastereomer | Variant Reaction medium Reaction temperature Reaction time Susp. medium Extractant | Yield % |
|---|---|---|---|---|
| Ir(L550)₃ | L550 | | C — 280° C. 24 h ethanol o-xylene | 26 |
| Ir(L551)₃ | L551 | | C — 300° C. 24 h ethanol o-xylene | 12 |
| Ir(L552)₃ | L552 | | B — 320° C. 36 h ethanol o-xylene | 13 |

-continued

| Ex. | Ligand | Ir complex Diastereomer | Variant Reaction medium Reaction temperature Reaction time Susp. medium Extractant | Yield % |
|---|---|---|---|---|
| Ir(L553)₃ | L553 | *(structure)* | B — 320° C. 36 h ethanol o-xylene | 15 |
| Ir(L554)₃ | L554 | *(structure)* | C — 260° C. 24 h ethyl acetate o-xylene | 18 |
| Ir(L555)₃ | L555 | *(structure)* | C — 300° C. 24 h ethanol o-xylene | 14 |

-continued
| Ex. | Ligand | Ir complex Diastereomer | Variant Reaction medium Reaction temperature Reaction time Susp. medium Extractant | Yield % |
|---|---|---|---|---|
| Ir(L556)$_3$ | L556 | 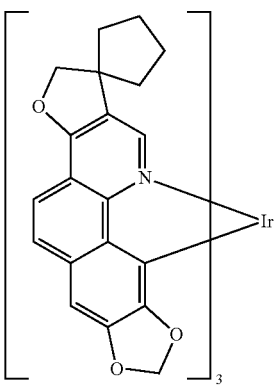 | A — 280° C. 36 h ethanol o-xylene | 18 |
| Ir(L557)$_3$ | L557 | 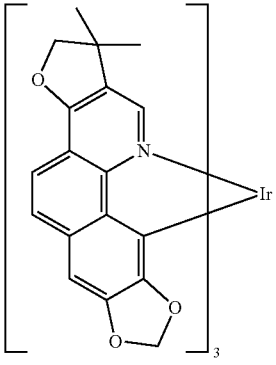 | A — 280° C. 24 h ethanol o-xylene | 12 |
| Ir(L558)$_3$ | L558 | 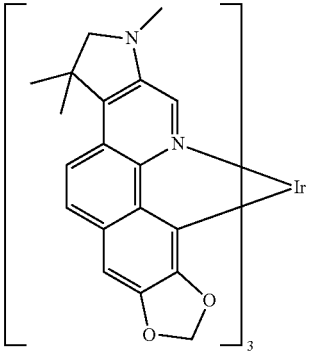 | A — 280° C. 24 h ethanol o-xylene | 12 |

-continued

| Ex. | Ligand | Ir complex Diastereomer | Variant Reaction medium Reaction temperature Reaction time Susp. medium Extractant | Yield % |
|---|---|---|---|---|
| Ir(L559)$_3$ | L559 | | A — 280° C. 24 h ethanol o-xylene | 11 |
| Ir(L560)$_3$ | L560 | | B — 300° C. 24 h ethanol o-xylene | 33 |
| Ir(L561)$_3$ | L561 | | B — 300° C. 24 h ethanol o-xylene | 30 |
| Ir(L562)$_3$ | L562 | | B — 300° C. 24 h ethanol o-xylene | 32 |

-continued

| Ex. | Ligand | Ir complex Diastereomer | Variant Reaction medium Reaction temperature Reaction time Susp. medium Extractant | Yield % |
|---|---|---|---|---|
| Ir(L563)$_3$ | L563 | | B — 300° C. 24 h ethanol o-xylene | 29 |
| Ir(L564)$_3$ | L564 | | B — 300° C. 24 h ethanol o-xylene | 34 |
| Ir(L565)$_3$ | L565 | | A — 280° C. 36 h ethanol o-xylene | 37 |
| Ir(L566)$_3$ | L566 | | C — 300° C. 36 h ethanol o-xylene | 18 |

-continued

| Ex. | Ligand | Ir complex Diastereomer | Variant Reaction medium Reaction temperature Reaction time Susp. medium Extractant | Yield % |
|---|---|---|---|---|
| Ir(L567)₃ | L567 | | C — 320° C. 48 h ethanol o-xylene | 15 |
| Ir(L568)₃ | L568 | | C — 320° C. 48 h ethanol o-xylene | 12 |
| Ir(L569)₃ | L569 | | A — 280° C. 24 h ethanol o-xylene | 19 |
| Ir(L570)₃ | L570 | | C — 340° C. 36 h ethanol o-xylene | 14 |

-continued

| Ex. | Ligand | Ir complex Diastereomer | Variant Reaction medium Reaction temperature Reaction time Susp. medium Extractant | Yield % |
|---|---|---|---|---|
| Ir(L571)$_3$ | L571 | | A — 260° C. 48 h ethyl acetate o-xylene | 33 |
| Ir(L572)$_3$ | L572 | | A — 260° C. 24 h ethyl acetate o-xylene | 35 |
| Ir(L573)$_3$ | L573 | | A — 260° C. 24 h ethyl acetate o-xylene | 38 |
| Ir(L574)$_3$ | L574 | | A — 260° C. 24 h ethyl acetate o-xylene | 36 |

-continued

| Ex. | Ligand | Ir complex Diastereomer | Variant Reaction medium Reaction temperature Reaction time Susp. medium Extractant | Yield % |
|---|---|---|---|---|
| Ir(L575)₃ | L575 | (structure) | C — 280° C. 24 h ethanol o-xylene | 19 |
| Ir(L576)₃ | L576 | (structure) | C — 280° C. 24 h ethanol o-xylene | 21 |
| Ir(L577)₃ | L577 | (structure) | C — 280° C. 24 h ethanol o-xylene | 20 |

-continued

| Ex. | Ligand | Ir complex Diastereomer | Variant Reaction medium Reaction temperature Reaction time Susp. medium Extractant | Yield % |
|---|---|---|---|---|
| Ir(L578)$_3$ | L578 | | C — 280° C. 24 h ethanol o-xylene | 21 |
| Ir(L579)$_3$ | L579 | | C — 280° C. 24 h ethanol o-xylene | 16 |
| Ir(L580)$_3$ | L580 | | B — 280° C. 24 h ethanol o-xylene | 21 |

-continued

| Ex. | Ligand | Ir complex Diastereomer | Variant Reaction medium Reaction temperature Reaction time Susp. medium Extractant | Yield % |
|---|---|---|---|---|
| Ir(L581)$_3$ | L581 | | B — 300° C. 48 h ethyl acetate o-xylene | 8 |
| Ir(L582)$_2$ | L582 | | C — 320° C. 48 h ethanol o-xylene | 6 |
| Ir(L583)$_3$ | L583 | | C — 320° C. 48 h ethanol o-xylene | 5 |

-continued

| Ex. | Ligand | Ir complex Diastereomer | Variant Reaction medium Reaction temperature Reaction time Susp. medium Extractant | Yield % |
|---|---|---|---|---|
| Ir(L584)₃ | L584 | | C — 280° C. 24 h ethanol o-xylene | 9 |
| Ir(L585)₃ | L585 | | C — 320° C. 24 h ethanol o-xylene | 11 |
| Ir(L586)₃ | L586 | | A — 260° C. 24 h ethanol o-xylene | 9 |

-continued

| Ex. | Ligand | Ir complex Diastereomer | Variant Reaction medium Reaction temperature Reaction time Susp. medium Extractant | Yield % |
|---|---|---|---|---|
| Ir(L587)₃ | L587 | (structure) | A — 260° C. 24 h ethanol o-xylene | 12 |
| Ir(L588)₃ | L588 | (structure) | A — 260° C. 24 h ethanol o-xylene | 11 |
| Ir(L589)₃ | L589 | (structure) | A — 260° C. 24 h ethanol o-xylene | 12 |
| Ir(L1000)₃ | L1000 | (structure) | C — 280° C. 24 h acetone o-xylene | 27 |

-continued

| Ex. | Ligand | Ir complex Diastereomer | Variant Reaction medium Reaction temperature Reaction time Susp. medium Extractant | Yield % |
|---|---|---|---|---|
| Ir(L1001)$_3$ | L1001 | | C — 280° C. 24 h acetone o-xylene | 25 |
| Ir(L1002)$_3$ | L1002 | | C — 280° C. 24 h acetone o-xylene | 29 |
| Ir(L1500)$_3$ | L1500 | | A — 260° C. 24 h ethyl acetate mesitylene | 38 |
| Ir(L1501)$_3$ | L1501 | | A — 280° C. 24 h ethyl acetate mesitylene | 35 |

-continued

| Ex. | Ligand | Ir complex Diastereomer | Variant Reaction medium Reaction temperature Reaction time Susp. medium Extractant | Yield % |
|---|---|---|---|---|
| Ir(L1502)₃ | L1502 | | A — 280° C. 24 h ethyl acetate mesitylene | 36 |
| Ir(L1503)₃ | L1503 | | A — 280° C. 24 h ethyl acetate mesitylene | 32 |
| Ir(L1504)₃ | L1504 | | A — 280° C. 24 h ethyl acetate mesitylene | 34 |
| Ir(L1505)₃ | L1505 | | A — 280° C. 24 h ethyl acetate mesitylene | 31 |

-continued

| Ex. | Ligand | Ir complex Diastereomer | Variant Reaction medium Reaction temperature Reaction time Susp. medium Extractant | Yield % |
|---|---|---|---|---|
| Ir(L1506)$_3$ | L1506 | | A — 300° C. 48 h ethyl acetate mesitylene | 17 |
| Ir(L1507)$_3$ | L1507 | | A — 320° C. 36 h ethyl acetate mesitylene | 12 |
| Ir(L1508)$_3$ | L1508 | | A — 260° C. 24 h ethanol mesitylene | 29 |
| Ir(L1509)$_3$ | L1509 | | A — 260° C. 24 h ethanol mesitylene | 33 |

| Ex. | Ligand | Ir complex Diastereomer | Variant Reaction medium Reaction temperature Reaction time Susp. medium Extractant | Yield % |
|---|---|---|---|---|
| Ir(L1510)₃ | L1510 | [structure] | A — 260° C. 24 h ethanol mesitylene | 31 |
| Ir(L1512)₃ | L1511 | [structure] | A — 260° C. 24 h ethanol mesitylene | 36 |

2) Heteroleptic Iridium Complexes:

Variant A:

Step 1:

A mixture of 10 mmol of sodium bisacetylacetonatodichloroindate(III) [770720-50-8] and 24 mmol of the ligand L and a glass-ensheathed magnetic stirrer bar are sealed by melting under reduced pressure ($10^{-5}$ mbar) into a thick-wall 50 mL glass ampoule. The ampoule is heated at the temperature specified for the time specified, in the course of which the molten mixture is stirred with the aid of a magnetic stirrer bar. After cooling—CAUTION: the ampoules are usually under pressure!—the ampoule is opened, the sinter cake is stirred with 100 g of glass beads (diameter 3 mm) in 100 mL of the suspension medium specified (the suspension medium is chosen such that the ligand has good solubility but the chloro dimer of the formula $[Ir(L)_2Cl]_2$ has sparing solubility therein; typical suspension media are DCM, acetone, ethyl acetate, toluene, etc.) for 3 h and mechanically digested in the process. The fine suspension is decanted off from the glass beads, and the solid $(Ir(L)_2Cl)_2$ which still contains about 2 eq of NaCl, referred to hereinafter as the crude chloro dimer) is filtered off with suction and dried under reduced pressure.

Step 2

The crude chloro dimer of the formula $[Ir(L)_2Cl]_2$ thus obtained is suspended in a mixture of 75 mL of 2-ethoxyethanol and 25 mL of water, and 13 mmol of the coligand CL or of the coligand compound CL and 15 mmol of sodium carbonate are added thereto. After 20 h under reflux, a further 75 mL of water are added dropwise, the mixture is cooled and then the solids are filtered off with suction, and these are washed three times with 50 mL each time of water and three times with 50 mL each time of methanol, and dried under reduced pressure. The dry solid is placed in a continuous hot extractor on an Alox bed of height 3-5 cm (Alox, basic, activity level 1) and then extracted with the extractant specified (initial charge of about 500 mL; the extractant is chosen such that the complex has good solubility in the hot extractant and sparing solubility in the cold extractant; suitable extractants are hydrocarbons such as toluene, xylenes, mesitylene, naphthylene, o-dichlorobenzene, tetrahydrofuran, dichloromethane, 1,2-dichloroethane, 1,1,2,2-tetrachloroethane, chloroform, carbon tetrachloride). After the extraction has ended, the extractant is concentrated under reduced pressure to about 100 mL. Metal complexes having too good a solubility in the extractant are made to crystallize by dropwise addition of 200 mL of methanol. The solid from the suspensions thus obtained is filtered off with suction, washed once with about 50 mL of methanol and dried. After drying, the purity of the metal complex is determined by means of NMR and/or HPLC. If the purity is below 99.5%, the hot extraction step is repeated. Once the purity of 99.5%-99.9% has been attained, the metal complex is heat-treated or sublimed. As well as the hot extraction process for purification, purification can also be effected by chromatography on silica gel or Alox. The heat treatment is effected under high vacuum (p about $10^{-6}$ mbar) within the temperature range of about 200-300° C. The sublimation is effected under high vacuum (p about $10^{-6}$ mbar) within the temperature range of about 300-400° C., the sublimation preferably being conducted in the form of a fractional sublimation.

| Ex. | Ligand L | Co-ligand CL | Ir complex Step 1: Reaction temp./Reaction time/Suspension medium Steps 2: Extractant | Yield |
|---|---|---|---|---|
| Ir(L3)₂(CL1) | L3 | 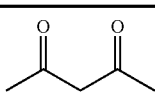<br>123-54-6<br>CL1 | 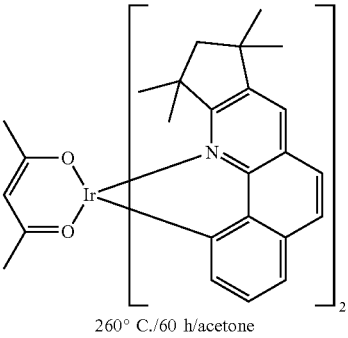<br>260° C./60 h/acetone<br>xylene | 28% |
| Ir(L4)₂(CL1) | L4 | CL1 | 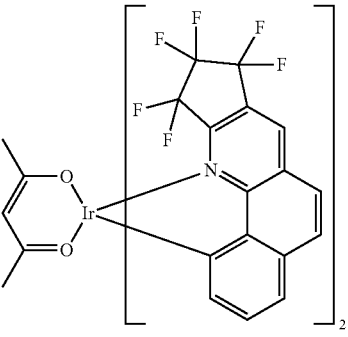<br>280° C./80 h/acetone<br>xylene | 25% |
| Ir(L5)₂(CL1) | L5 | CL1 | 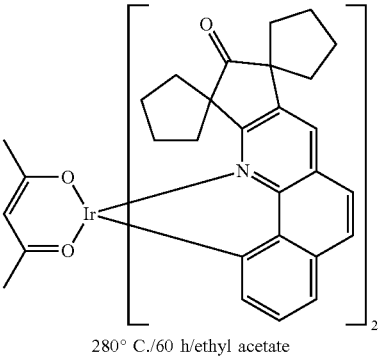<br>280° C./60 h/ethyl acetate<br>xylene | 16% |
| Ir(L6)₂(CL1) | L6 | CL1 | 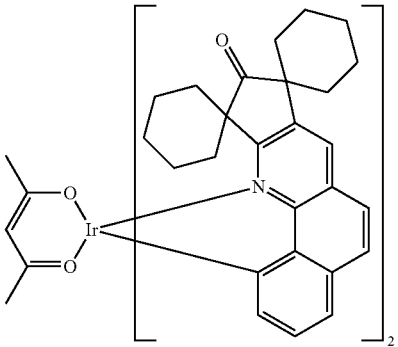<br>260° C./80 h/acetone<br>xylene | 15% |

-continued
| Ex. | Ligand L | Co-ligand CL | Ir complex Step 1: Reaction temp./Reaction time/Suspension medium Steps 2: Extractant | Yield |
|---|---|---|---|---|
| Ir(L7)$_2$(CL1) | L7 | CL1 | 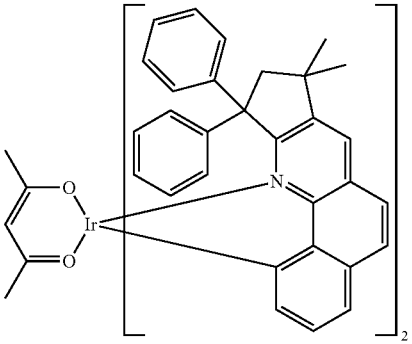<br>300° C./80 h/acetone<br>xylene | 16% |
| Ir(L10)$_2$(CL1) | L10 | CL1 | 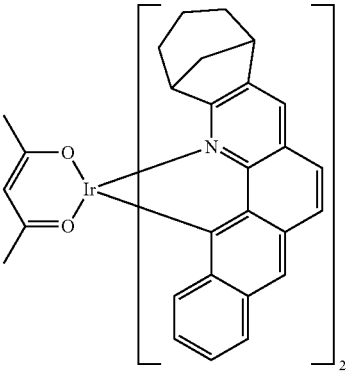<br>280° C./80 h/ethyl acetate<br>xylene | 15% |
| Ir(L11)$_2$(CL1) | L11 | CL1 | 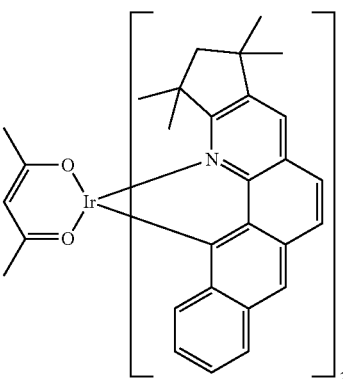<br>260° C./80 h/ethyl acetate<br>xylene | 16% |

-continued

| Ex. | Ligand L | Co-ligand CL | Ir complex Step 1: Reaction temp./ Reaction time/ Suspension medium Steps 2: Extractant | Yield |
|---|---|---|---|---|
| Ir(L12)₂(CL1) | L12 | CL1 | 280° C./60 h/acetone xylene | 25% |
| Ir(L13)₂(CL1) | L13 | CL1 | 300° C./90 h/acetone xylene | 16% |
| Ir(L14)₂(CL2) | L14 | 1118-71-4 CL2 | 300° C./90 h/ethyl acetate xylene | 19% |

| Ex. | Li-gand L | Co-ligand CL | Ir complex Step 1: Reaction temp./ Reaction time/ Suspension medium Steps 2: Extractant | Yield |
|---|---|---|---|---|
| Ir(L15)₂(CL2) | L15 | CL2 | 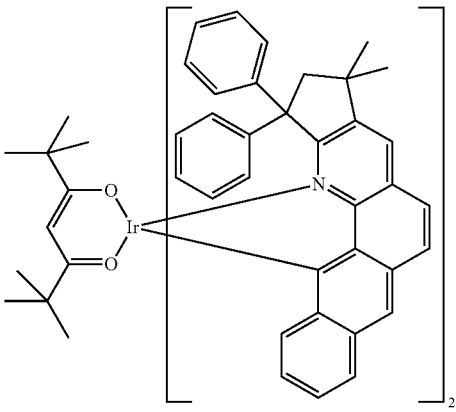<br>320° C./80 h/acetone<br>xylene | 14% |
| Ir(L26)₂(CL2) | L26 | CL2 | 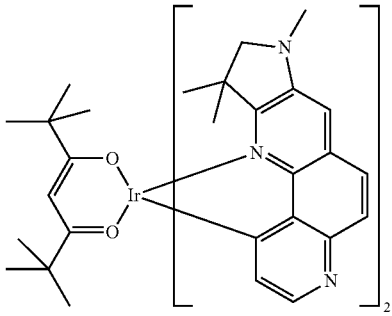<br>280° C./60 h/acetone<br>xylene | 30% |
| Ir(L33)₂(CL2) | L33 | CL2 | 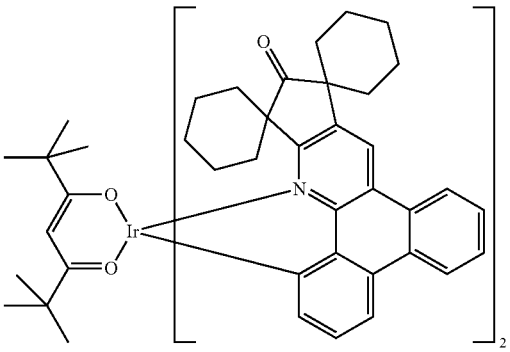<br>280° C./60 h/acetone<br>xylene | 14% |

-continued
| Ex. | Ligand L | Co-ligand CL | Ir complex Step 1: Reaction temp./Reaction time/Suspension medium Steps 2: Extractant | Yield |
|---|---|---|---|---|
| Ir(L500)₂(CL2) | L500 | CL2 | 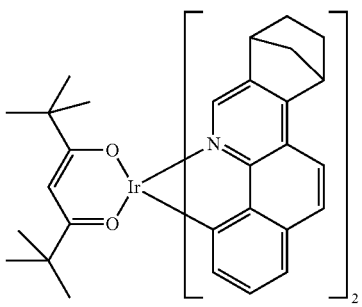 280° C./80 h/acetone xylene | 60% |
| Ir(L503)₂(CL2) | L503 | CL2 | 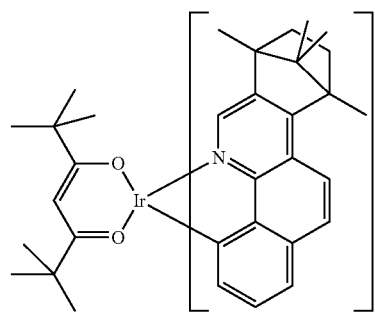 280° C./60 h/acetone xylene | 54% |
| Ir(L505)₂(CL2) | L505 | CL2 | 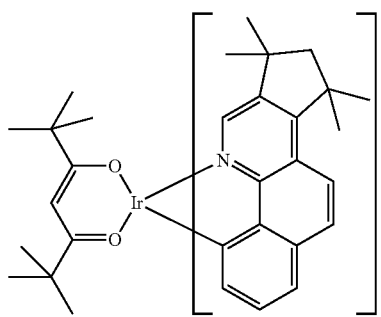 280° C./60 h/acetone xylene | 60% |
| Ir(L518)₂(CL3) | L518 | 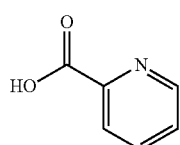 98-98-6 CL3 | 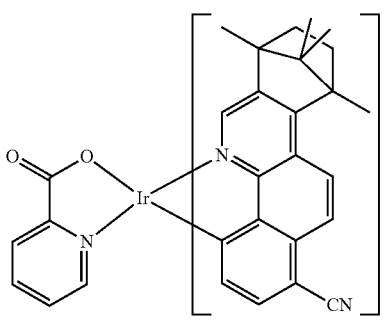 280° C./80 h/acetone xylene | 27% |

-continued

| Ex. | Ligand L | Coligand CL | Ir complex Step 1: Reaction temp./Reaction time/Suspension medium Steps 2: Extractant | Yield |
|---|---|---|---|---|
| Ir(L523)₂(CL3) | L523 | CL3 | 280° C./80 h/acetone xylene | 22% |
| Ir(L548)₂(CL3) | L548 | CL3 | 280° C./80 h/acetone xylene | 27% |
| Ir(L553)₂(CL3) | L553 | CL3 | 280° C./80 h/acetone xylene | 24% |

-continued

| Ex. | Ligand L | Co-ligand CL | Ir complex Step 1: Reaction temp./Reaction time/Suspension medium Steps 2: Extractant | Yield |
|---|---|---|---|---|
| Ir(L556)₂(CL3) | L556 | CL3 | 280° C./80 h/acetone xylene | 29% |
| Ir(L565)₂(CL4) | L565 | 18653-75-3 CL4 | 260° C./60 h/acetone xylene | 44% |
| Ir(L568)₂(CL4) | L568 | CL4 | 260° C./80 h/acetone xylene | 44% |

-continued

| Ex. | Ligand L | Coligand CL | Ir complex Step 1: Reaction temp./ Reaction time/ Suspension medium Steps 2: Extractant | Yield |
|---|---|---|---|---|
| Ir(L586)₂(CL5) | L586 | 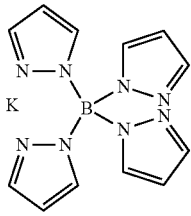<br>14782-58-2<br>CL5 | 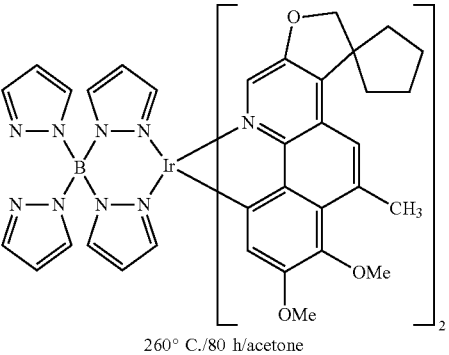<br>260° C./80 h/acetone<br>xylene | 50% |
| Ir(L1508)₂(CL7) | L1508 | 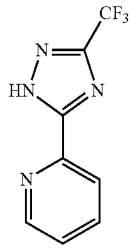 [SMILES: FC(F)(F)c1n[nH]c(-c2ccccn2)n1]<br>219508-27-7<br>CL6 | 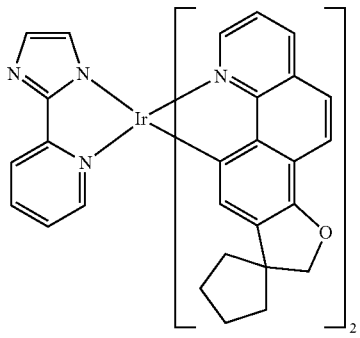<br>280° C./80 h/Aceton<br>xylene | 47% |

Variant B:

Step 1:

See variant A, step 1.

Step 2:

The crude chloro dimer of the formula [Ir(L)₂Cl]₂ is suspended in 200 mL of THF, and to the suspension are added 20 mmol of the coligand CL, 20 mmol of silver(I) trifluoroacetate and 30 mmol of potassium carbonate, and the mixture is heated under reflux for 24 h. After cooling, the THF is removed under reduced pressure. The residue is taken up in 200 mL of a mixture of ethanol and conc. ammonia solution (1:1, v:v). The suspension is stirred at room temperature for 1 h, and the solids are filtered off with suction, washed twice with 50 mL each time of a mixture of ethanol and conc. ammonia solution (1:1, v:v) and twice with 50 mL each time of ethanol, and then dried under reduced pressure. Hot extraction and sublimation as in variant A.

| Ex. | Ligand L | Co-ligand CL | Ir complex Step 1: Reaction temp./Reaction time/Suspension medium Steps 2: Extractant | Yield |
|---|---|---|---|---|
| Ir(L3)₂(CL7) | L3 | <br>391604/-55<br>CL7 | 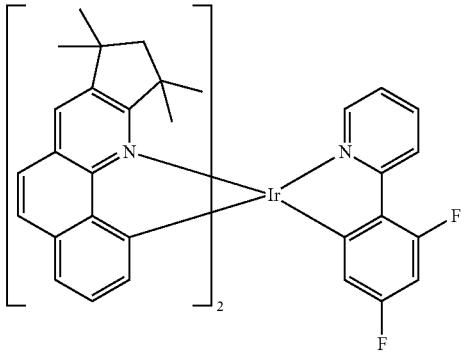<br>as ex. Ir(L98)₂(CL2) | 39% |
| Ir(L503)₂(CL8) | L503 | 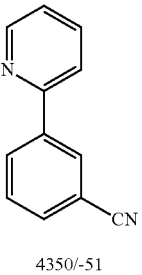<br>4350/-51<br>CL8 | 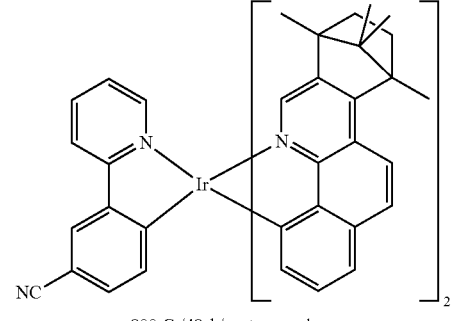<br>90° C./48 h/acetone xylene | 31% |
| Ir(L565)₂(CL8) | L565 | 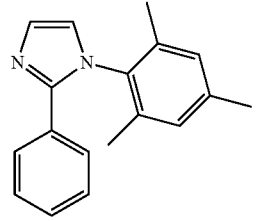 [SMILES: Cc1cc(C)c(-n2ccnc2-c2ccccc2)c(C)c1]<br>1093072-00-4<br>CL9 | 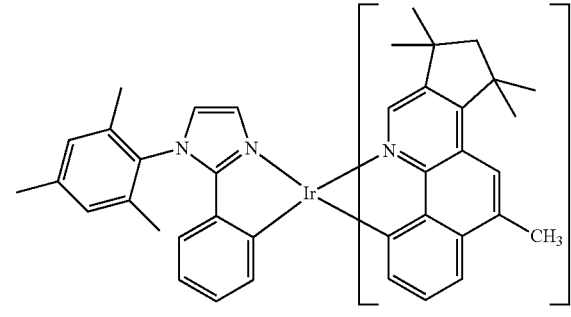<br>290° C./60 h/acetone xylene | 39% |
| Ir(L1508)₂(CL10) | L1508 | 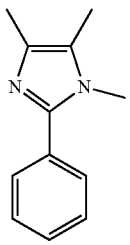<br>152536-39-5<br>CL10 | 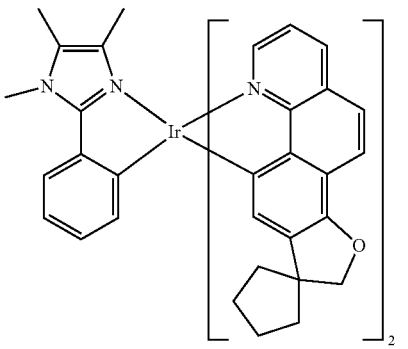<br>300° C./80 h/acetone xylene | 38% |

Variant C:
Step 1:
See variant A, step 1.
Step 2:
The crude chloro dimer of the formula [Ir(L)$_2$Cl]$_2$ is suspended in 1000 mL of dichloromethane and 150 mL of ethanol, to the suspension are added 20 mmol of silver(I) trifluoromethanesulfonate, and the mixture is stirred at room temperature for 24 h. The precipitated solids (AgCl) are filtered off with suction using a short Celite bed and the filtrate is concentrated to dryness. The solids thus obtained are taken up in 100 mL of ethylene glycol, 20 mmol of the coligand CL added thereto and then the mixture is stirred at 130° C. for 30 h. After cooling, the solids are filtered off with suction, washed twice with 50 mL each time of ethanol and dried under reduced pressure. Hot extraction and sublimation as in variant A.

| Ex. | Ligand L | Coligand CL | Ir complex Step 1: Reaction temp./ Reaction time/ Suspension medium Steps 2: Extractant | Yield |
|---|---|---|---|---|
| Ir(L586)$_2$(CL11) | L586 | 914306-48-2 CL11 | 290° C./80 h/acetone xylene | 46% |
| Ir(L588)$_2$(CL11) | L588 | CL11 | 290° C./80 h/acetone xylene | 39% |
| Ir(L553)$_2$(CL12) | L553 | 39696-58-7 CL12 | 300° C./80 h/acetone xylene | 44% |

Variant E:

A mixture of 10 mmol of the Ir complex Ir(L)$_2$(CL1 or CL2), 20 mmol of the ligand L and a glass-ensheathed magnetic stirrer bar are sealed by melting under reduced pressure ($10^{-5}$ mbar) into a 50 mL glass ampoule. The ampoule is heated at the temperature specified for the time specified, in the course of which the molten mixture is stirred with the aid of a magnetic stirrer bar. Further workup, purification and sublimation as described in 1) Homoleptic tris-facial iridium complexes.

| Ex. | Ir complex Ir(L)$_2$(CL) | Li-ligand L' | Ir complex Step 1: Reaction temp./ Reaction time/ Suspension medium Steps 2: Extractant | Yield |
|---|---|---|---|---|
| Ir(L505)$_2$(L588) | Ir(L505)$_2$(CL2) | L588 | 280° C./80 h/DCM mesitylene | 39% |
| Ir(L548)$_2$(L26) | Ir(L548)$_2$(CL3) | L26 | 300° C./70 h/DCM mesitylene | 43% |
| Ir(L556)$_2$(L4) | Ir(L556)$_2$(CL3) | L4 | 300° C./70 h/DCM mesitylene | 44% |

| Ex. | Ir complex Ir(L)₂(CL) | Li-ligand L' | Ir complex Step 1: Reaction temp./ Reaction time/ Suspension medium Steps 2: Extractant | Yield |
|---|---|---|---|---|
| Ir(L13)₂(L1508) | Ir(L13)₂(CL1) | L1508 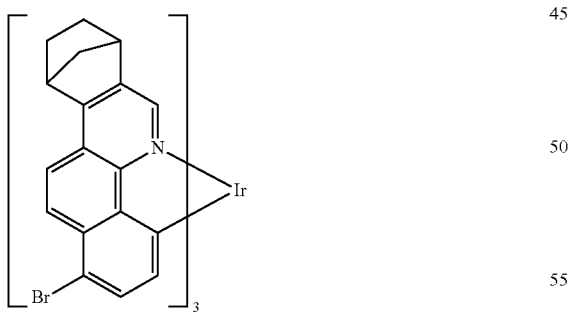 | 305° C./70 h/DCM mesitylene | 36% |

E: Derivatization of the Metal Complexes

1) Halogenation of the Iridium Complexes:

To a solution or suspension of 10 mmol of a complex bearing A×C–H groups (with A=1, 2 or 3) in the para position to the iridium in 3000 mL of dichloromethane is added, in the dark and with exclusion of air, at 30° C., A ×11 mmol of N-halosuccinimide (halogen: Cl, Br, I), and the mixture is stirred for 20 h. Complexes of sparing solubility in DCM may also be converted in other solvents (TCE, THF, DMF, etc.) and at elevated temperature. Subsequently, the solvent is substantially removed under reduced pressure. The residue is extracted by boiling with 100 mL of MeOH, and the solids are filtered off with suction, washed three times with 30 mL of methanol and then dried under reduced pressure.

Synthesis of Ir(L500-Br)₃:

To a suspension, stirred at 30° C., of 11.3 g (10 mmol) of Ir(L500)₃ in 3000 mL of DCM are added 5.9 g (33 mmol) of N-bromosuccinimide all at once and the mixture is stirred for 20 h. After removing about 2900 mL of the DCM under reduced pressure, 100 mL of methanol are added to the yellow suspension, and the solids are filtered off with suction, washed three times with about 30 mL of methanol and then dried under reduced pressure. Yield: 13.8 g (9.5 mmol), 95%; purity: about 99.6% by NMR.

In an analogous manner it is possible to prepare the following compounds:

| Ex. | Complex | Brominated complex | Yield |
|---|---|---|---|
| Ir(L8-Br)$_3$ | Ir(L8)$_3$ | Ir(L8-Br)$_3$ | 93% |
| Ir(L16-Br)$_3$ | Ir(L16)$_3$ | Ir(L16-Br)$_3$ | 95% |
| Ir(L505-Br)$_3$ | Ir(L505)$_3$ | Ir(L505-Br)$_3$ | 97% |

2) Suzuki Coupling with the Iridium Complexes:

Variant a, Biphasic Reaction Mixture:

To a suspension of 10 mmol of a brominated complex, 40-80 mmol of the boronic acid or boronic ester and 80 mmol of tripotassium phosphate in a mixture of 300 mL of toluene, 100 mL of dioxane and 300 mL of water are added 0.6 mmol of tri-o-tolylphosphine and 0.1 mmol of palladium (II) acetate, and the mixture is heated under reflux for 16 h. After cooling, 500 mL of water and 200 mL of toluene are added, the aqueous phase is removed, and the organic phase is washed three times with 200 mL of water and once with 200 mL of saturated sodium chloride solution and dried over magnesium sulfate. The mixture is filtered through a Celite bed and washed through with toluene, the toluene is removed almost completely under reduced pressure, 300 mL of ethanol are added, and the precipitated crude product is filtered off with suction, washed three times with 100 mL each time of EtOH and dried under reduced pressure. The crude product is columned twice with toluene through silica gel. The metal complex is finally heat-treated or sublimed. The heat treatment is effected under high vacuum (p about $10^{-6}$ mbar) within the temperature range of about 200-300° C. The sublimation is effected under high vacuum (p about $10^{-6}$ mbar) within the temperature range of about 300-400° C., the sublimation preferably being conducted in the form of a fractional sublimation.

Variant B, Monophasic Reaction Mixture:

To a suspension of 10 mmol of a brominated complex, 40-80 mmol of the boronic acid or boronic ester and 60-100 mmol of the base (potassium fluoride, tripotassium phosphate, potassium carbonate, cesium carbonate etc., each in anhydrous form) and 100 g of glass beads (diameter 3 mm) in 100 mL-500 mL of an aprotic solvent (THF, dioxane, xylene, mesitylene, dimethylacetamide, NMP, DMSO, etc.) are added 0.6 mmol of tri-o-tolylphosphine and 0.1 mmol of palladium(II) acetate, and the mixture is heated under reflux for 1-24 h. Alternatively, it is possible to use other phosphines such as tri-tert-butylphosphine, di-tert-butylphosphine, S-Phos, Xanthphos, etc., the preferred phosphine: palladium ratio in the case of these phosphines being 2:1 to 1.2:1. The solvent is removed under reduced pressure, the product is taken up in a suitable solvent (toluene, dichloromethane, ethyl acetate, etc.) and purification is effected as described in A.

Synthesis of Ir(L2000)$_3$:

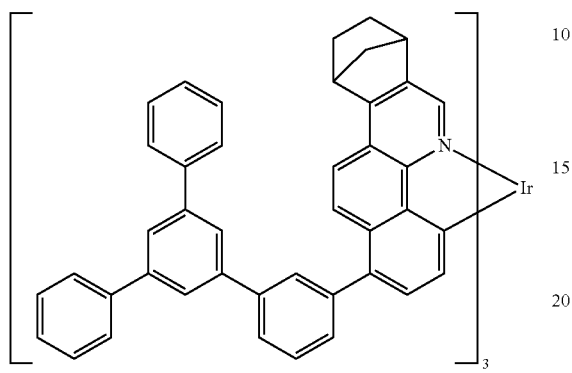

Variant B:

Use of 11.6 g (10 mmol) of Ir(L500-Br)$_3$ and 14.0 g (40 mmol) of quaterphenylboronic acid [1233200-59-3], cesium carbonate, tri-ortho-tolylphosphine, NMP, 180° C., 2 h. Yield: 12.7 g (6.9 mmol), 69%; purity: about 99.8% by HPLC.

In an analogous manner, it is possible to prepare the following compounds:

| Ex. | Product Variant | Yield |
|---|---|---|
| Ir(L2001)$_3$ | Ir(L8-Br)$_3$ + [952583-08-3]<br>B, as Ir(2000)$_3$ | 57% |

-continued
| Ex. | Product Variant | Yield |
|---|---|---|
| Ir(L2002)₃ | 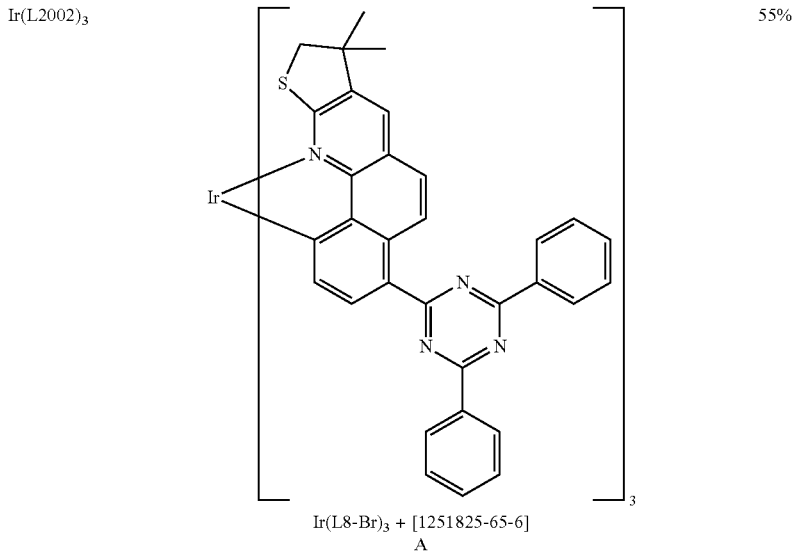<br>Ir(L8-Br)₃ + [1251825-65-6]<br>A | 55% |
| Ir(L2003)₃ | 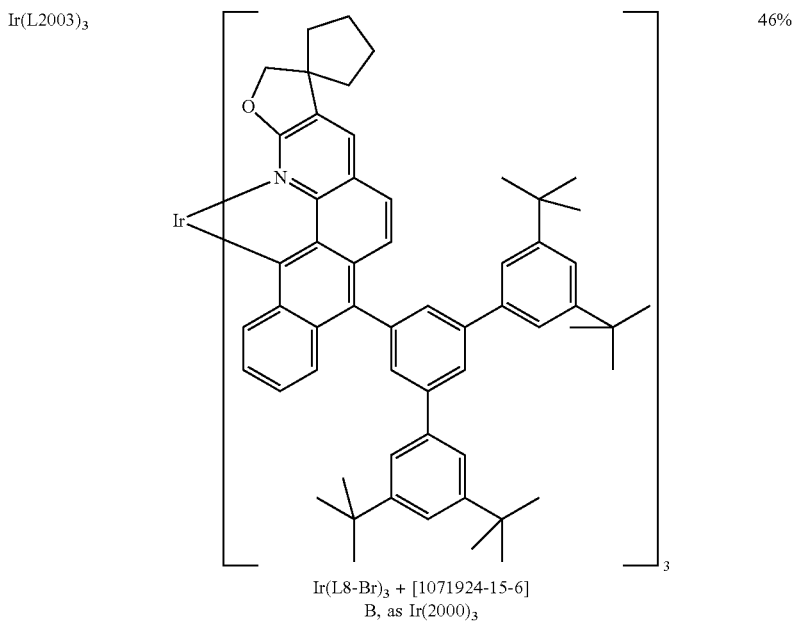<br>Ir(L8-Br)₃ + [1071924-15-6]<br>B, as Ir(2000)₃ | 46% |
| Ir(L2004)₃ | 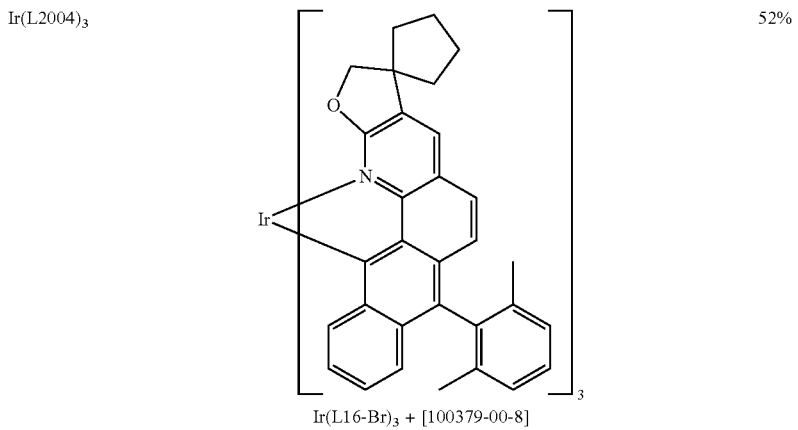<br>Ir(L16-Br)₃ + [100379-00-8] | 52% |

| Ex. | Product Variant | Yield |
|---|---|---|
| | B, as Ir(2000)₃, dioxane rather than NMP | |
| Ir(L2005)₃ | 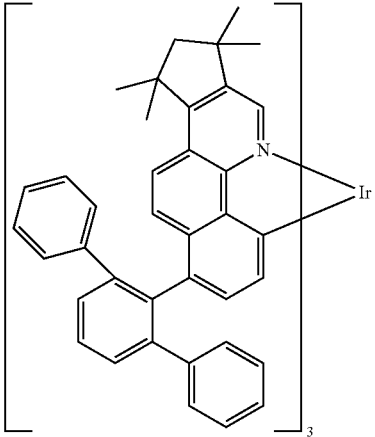<br>Ir(L505-Br)₃ + [1065663-52-6]<br>B, as Ir(2000)₃ | 23% |
| Ir(L2006)₃ | 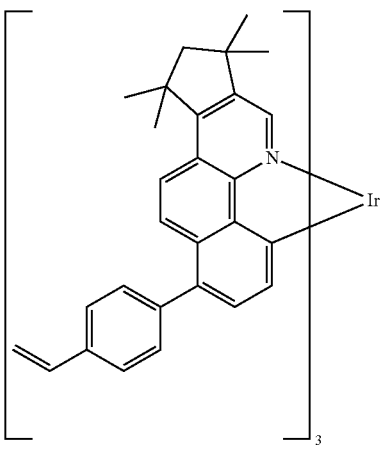<br>Ir(L505-Br)₃ + [2156-04-9]<br>B, as Ir(2000)₃, DMAC rather than NMP | 25% |

3) Buchwald Coupling with the Iridium Complexes:

To a mixture of 10 mmol of the brominated complex, 40 mmol of the diarylamine or carbazole, 45 mmol of sodium tert-butoxide in the case of the amines or 80 mmol of tripotassium phosphate (anhydrous) in the case of carbazoles, 100 g of glass beads (diameter 3 mm) and 300-500 mL of o-xylene or mesitylene are added 0.4 mmol of tri-tert-butylphosphine and then 0.3 mmol of palladium(III) acetate, and the mixture is heated under reflux with good stirring for 16 h. After cooling, the aqueous phase is removed, and the organic phase is washed twice with 200 mL of water and once with 200 mL of saturated sodium chloride solution and dried over magnesium sulfate. The mixture is filtered through a Celite bed and washed through with o-xylene or mesitylene, the solvent is removed almost completely under reduced pressure, 300 mL of ethanol are added, and the precipitated crude product is filtered off with suction, washed three times with 100 mL each time of EtOH and dried under reduced pressure. The crude product is columned twice with toluene on silica gel. The metal complex is finally heat-treated or sublimed. The heat treatment is effected under high vacuum (p about $10^{-6}$ mbar) within the temperature range of about 200-300° C. The sublimation is effected under high vacuum (p about $10^{-6}$ mbar) within the temperature range of about 300-400° C., the sublimation preferably being conducted in the form of a fractional sublimation.

Synthesis of Ir(L2500)₃:

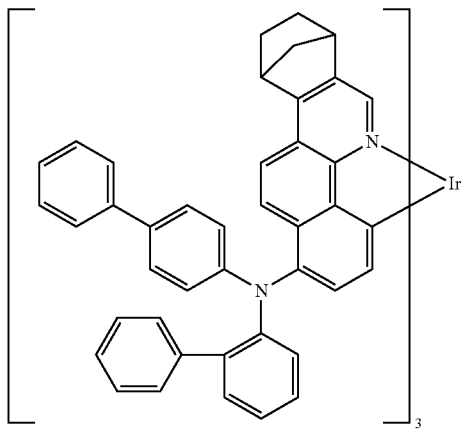

Use of 11.6 g (10 mmol) of Ir(L500-Br)₃ and 12.9 g (40 mmol) of p-biphenyl-o-biphenylamine [1372775-52-4], mesitylene. Yield: 11.1 g (5.3 mmol), 53%; purity: about 99.8% by HPLC.

In an analogous manner, it is possible to prepare the following compounds:

| Ex. | Product | Yield |
|---|---|---|
| Ir(L2501)₃ | Ir(L500-Br)₃ + [1257220-47-5] | 49% |
| Ir(L2502)₃ | Ir(L8-Br)₃ + [244-78-0] | 53% |
| Ir(L2503)₃ | Ir(L505-Br)₃ + [244-78-0] | 53% |
| Ir(L2504)₃ | Ir(L505-Br)₃ + [1257220-47-5] | 47% |

Production of the OLEDs

1) Vacuum-Processed Devices:

OLEDs of the invention and OLEDs according to the prior art are produced by a general method according to WO 2004/058911, which is adapted to the circumstances described here (variation in layer thickness, materials used). In the examples which follow, the results for various OLEDs are presented. Glass plaques with structured ITO (indium tin oxide) form the substrates to which the OLEDs are applied. The OLEDs basically have the following layer structure: substrate/hole transport layer 1 (HTL1) consisting of HTM doped with 3% NDP-9 (commercially available from Novaled), 20 nm/hole transport layer 2 (HTL2)/optional electron blocker layer (EBL)/emission layer (EML)/optional hole blocker layer (HBL)/electron transport layer (ETL)/ optional electron injection layer (EIL) and finally a cathode. The cathode is formed by an aluminum layer of thickness 100 nm.

First of all, vacuum-processed OLEDs are described. For this purpose, all the materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as M2:M1: Ir(L1)₃ (55%:35%:10%) mean here that the material M2 is present in the layer in a proportion by volume of 55%, M1 in a proportion of 35% and Ir(L1)₃ in a proportion of 10%. Analogously, the electron transport layer may also consist of a mixture of two materials. The exact structure of the OLEDs can be found in Table 1. The materials used for production of the OLEDs are shown in Table 6.

The OLEDs are characterized in a standard manner. For this purpose, the electroluminescence spectra, the power efficiency (measured in cd/A) and the voltage (measured at 1000 cd/m$^2$ in V) are determined from current-voltage-brightness characteristics (IUL characteristics). For selected experiments, the lifetime is determined. The lifetime is defined as the time after which the luminance has fallen from a particular starting luminance to a certain proportion. The figure LD50 means that the lifetime specified is the time at which the luminance has dropped to 50% of the starting luminance, i.e. from, for example, 1000 cd/m$^2$ to 500 cd/m$^3$. According to the emission color, different starting brightnesses are selected. The values for the lifetime can be converted to a figure for other starting luminances with the aid of conversion formulae known to those skilled in the art. In this context, the lifetime for a starting luminance of 1000 cd/m$^2$ is a standard figure.

Use of Compounds of the Invention as Emitter Materials in Phosphorescent OLEDs

One use of the compounds of the invention is as phosphorescent emitter materials in the emission layer in OLEDs. The compound Ir(Ref1)$_3$ is used as a comparison according to the prior art. The results for the OLEDs are collated in Table 2.

TABLE 1

Structure of the OLED

| Ex. | HTL2 thickness | EBL thickness | EML thickness | HBL thickness | ETL thickness |
|---|---|---|---|---|---|
| Yellow OLEDs ||||||
| D-Ref. | HTM 220 nm | — | M2:M1:Ir(Ref1)$_3$ (75%:15%:10%) 20 nm | HBM 10 nm | ETM1:ETM2 (50%:50%) 40 nm |
| D-Ir(L1)$_3$ | HTM 220 nm | — | M2:M1:Ir(L1)$_3$ (75%:15%:10%) 20 nm | HBM 10 nm | ETM1:ETM2 (50%:50%) 40 nm |
| D-Ir(L9)$_3$ | HTM 220 nm | — | M2:M1:Ir(L9)$_3$ (75%:15%:10%) 20 nm | HBM 10 nm | ETM1:ETM2 (50%:50%) 40 nm |
| D-Ir(L505)$_3$ | HTM 220 nm | — | M2:M1:Ir(L505)$_3$ (75%:15%:10%) 20 nm | HBM 10 nm | ETM1:ETM2 (50%:50%) 40 nm |
| D-Ir(L527)$_3$ | HTM 220 nm | — | M2:M1:Ir(L527)$_3$ (75%:15%:10%) 20 nm | HBM 10 nm | ETM1:ETM2 (50%:50%) 40 nm |
| D-Ir(L1001)$_3$ | HTM 220 nm | — | M2:M1:Ir(L1001)$_3$ (75%:15%:10%) 20 nm | HBM 10 nm | ETM1:ETM2 (50%:50%) 40 nm |
| D-Ir(L1500)$_3$ | HTM 220 nm | — | M2:M1:Ir(L1500)$_3$ (75%:15%:10%) 20 nm | HBM 10 nm | ETM1:ETM2 (50%:50%) 40 nm |
| D-Ir(L3)$_2$(CL1) | HTM 220 nm | — | M2:M1: Ir(L3)$_2$(CL1) (75%:15%:10%) 20 nm | HBM 10 nm | ETM1:ETM2 (50%:50%) 40 nm |
| D-Ir(L500)$_2$(CL2) | HTM 220 nm | — | M2:M1: Ir(L500)$_2$(CL2) (75%:15%:10%) 20 nm | HBM 10 nm | ETM1:ETM2 (50%:50%) 40 nm |
| D-Ir(L565)$_2$(CL4) | HTM 220 nm | — | M2:M1: Ir(L565)$_2$(CL4) (75%:15%:10%) 20 nm | HBM 10 nm | ETM1:ETM2 (50%:50%) 40 nm |
| D-Ir(L503)$_2$(CL8) | HTM 220 nm | — | M2:M1: Ir(L503)$_2$(CL8) (75%:15%:10%) 20 nm | HBM 10 nm | ETM1:ETM2 (50%:50%) 40 nm |

TABLE 2

Results for the vacuum-processed OLEDs

| Ex. | EQE (%) 1000 cd/m$^2$ | Voltage (V) 1000 cd/m$^2$ | CIE x/y 1000 cd/m$^2$ | LD50 (h) 1000 cd/m$^2$ |
|---|---|---|---|---|
| Yellow OLEDs |||||
| D-Ref. | 19.7 | 3.1 | 0.44/0.55 | 210000 |
| D-Ir(L1)$_3$ | 22.7 | 3.2 | 0.50/0.48 | 330000 |
| D-Ir(L9)$_3$ | 13.1 | 3.0 | 0.30/0.69 | — |
| D-Ir(L505)$_3$ | 23.0 | 3.2 | 0.48/0.50 | 320000 |
| D-Ir(L527)$_3$ | 19.8 | 3.6 | 0.61/0.38 | — |
| D-Ir(L1001)$_3$ | 22.3 | 3.1 | 0.46/0.53 | 340000 |
| D-Ir(L1500)$_3$ | 21.9 | 3.4 | 0.54/0.44 | 390000 |
| D-Ir(L3)$_2$(CL1) | 23.3 | 3.2 | 0.47/0.51 | 230000 |
| D-Ir(L500)$_2$(CL2) | 22.7 | 3.3 | 0.48/0.51 | 250000 |
| D-Ir(L565)$_2$(CL4) | 19.5 | 3.2 | 0.60/0.38 | — |
| D-Ir(L503)$_2$(CL8) | 21.8 | 3.4 | 0.51/0.48 | — |

2) Solution-Processed Devices

A: From Soluble Functional Materials

The iridium complexes of the invention may also be processed from solution and lead therein to OLEDs which are much simpler in terms of process technology compared to the vacuum-processed OLEDs, but nevertheless have good properties. The production of such components is based on the production of polymeric light-emitting diodes (PLEDs), which has already been described many times in the literature (for example in WO 2004/037887). The structure is composed of substrate/ITO/PEDOT (80 nm)/interlayer (80 nm)/emission layer (80 nm)/cathode. For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in the cleanroom, as a buffer layer, an 80 nm layer of PEDOT (PEDOT is a polythiophene derivative (Baytron P VAI 4083sp.) from H. C. Starck, Goslar, which is supplied as an aqueous dispersion) is applied by spin-coating. The required spin rate depends on the degree of dilution and the specific spin-coater geometry (typical value for 80 nm: 4500 rpm). In order to remove residual water from the layer, the substrates are baked on a hotplate at 180° C. for 10 minutes. The interlayer used serves for hole injection; in this case, HIL-012 from Merck is used. The interlayer may alternatively also be replaced by one or more layers which merely have to fulfill the condition of not being leached off again by the subsequent processing step of EML deposition from solution. For production of the emission layer, the emitters of the invention are dissolved together with the matrix materials in toluene. The typical solids content of such solutions is between 16 and 25 g/l when, as here, the layer thickness of 80 nm which is typical of a device is to be achieved by means of spin-coating. The solution-processed devices contain an emission layer composed of (polystyrene):M4:M5:Ir(L)$_3$ (25%:25%:40%:10%). The emission layer is spun on in an inert gas atmosphere, argon in the present case, and baked at 130° C. for 30 min. Lastly, a cathode composed of barium (5 nm) and then aluminum (100 nm) (high-purity metals from Aldrich, particularly barium 99.99% (cat. no. 474711); vapor deposition systems from Lesker or the like, typical vapor deposition pressure 5×10$ mbar) is applied by vapor deposition. It is optionally possible first to apply a hole blocker layer and then an electron transport layer and only then the cathode (e.g. Al or LiF/Al) by vapor deposition under reduced pressure. In order to protect the device from air and air humidity, the device is finally encapsulated and then characterized. The OLED examples cited are yet to be optimized; Table 3 summarizes the data obtained.

TABLE 3

Results with materials processed from solution

| Ex. | Ir(L)$_3$ | EQE (%) 1000 cd/m$^2$ | Voltage (V) 1000 cd/m$^2$ | CIE x/y 1000 cd/m$^2$ |
|---|---|---|---|---|
| Yellow OLEDs ||||| 
| S-Ir(L25)$_3$ | Ir(L25)$_3$ | 17.8 | 5.6 | 0.59/0.40 |
| S-Ir(L28)$_3$ | Ir(L28)$_3$ | 19.0 | 5.3 | 0.48/0.48 |
| S-Ir(L510)$_3$ | Ir(L510)$_3$ | 19.5 | 5.4 | 0.48/0.50 |
| S-Ir(L520)$_3$ | Ir(L520)$_3$ | 18.4 | 5.5 | 0.60/0.38 |
| S-Ir(L550)$_3$ | Ir(L550)$_3$ | 17.8 | 5.2 | 0.47/0.52 |
| S-Ir(L562)$_3$ | Ir(L562)$_3$ | 20.4 | 5.5 | 0.48/0.50 |
| S-Ir(L1000)$_3$ | Ir(L1000)$_3$ | 19.7 | 5.3 | 0.46/0.53 |
| S-Ir(L1507)$_3$ | Ir(L1507)$_3$ | 18.0 | 5.5 | 0.54/0.44 |
| S-Ir(L7)$_2$(CL1) | Ir(L7)$_2$(CL1) | 19.8 | 5.4 | 0.45/0.53 |
| S-Ir(L505)$_2$(CL2) | Ir(L505)$_2$(CL2) | 19.4 | 5.3 | 0.46/0.52 |
| S-Ir(L565)$_2$(CL8) | Ir(L565)$_2$(CL8) | 16.5 | 5.4 | 0.60/0.38 |
| S-Ir(L556)$_2$(L4) | Ir(L556)$_2$(L4) | 17.6 | 5.5 | 0.48/0.49 |
| S-Ir(L2000)$_3$ | Ir(L2000)$_3$ | 18.9 | 5.4 | 0.49/0.50 |
| S-Ir(L2504)$_3$ | Ir(L2504)$_3$ | 14.3 | 5.2 | 0.53/0.46 |

3) White-Emitting OLEDs

According to the general methods from 1), a white-emitting OLED having the following layer structure is produced:

TABLE 4

Structure of the white OLEDs

| Ex. | HTL2 thickness | EML red thickness | EML blue thickness | EML green thickness | HBL thickness | ETL thickness |
|---|---|---|---|---|---|---|
| D-W1 | HTM 230 nm | EBM:Ir—R (97%:3%) 9 nm | M3:M2:Ir—B (40%:50%:10%) 8 nm | M2:Ir(L527)$_3$ (90%:10%) 7 nm | HBM 10 nm | ETM1:ETM2 (50%:50%) 30 nm |

TABLE 5

Device results

| Ex. | EQE (%) 1000 cd/m$^2$ | Voltage (V) 1000 cd/m$^2$ | CIE x/y 1000 cd/m$^2$ CRI | LD50 (h) 1000 cd/m$^2$ |
|---|---|---|---|---|
| D-W1 | 20.3 | 6.5 | 0.43/0.4377 | 3000 |

TABLE 6

Structural formulae of the materials used

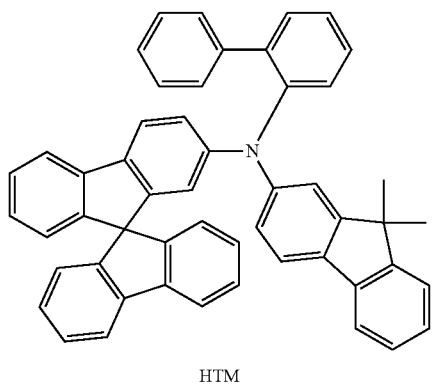

HTM

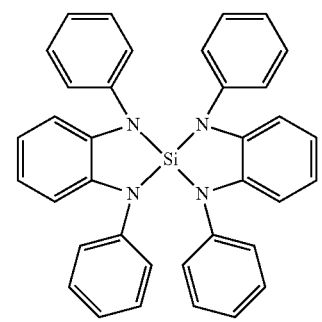 [SMILES: c1ccc(N2c3ccccc3N(c3ccccc3)[Si]23N(c2ccccc2)c2ccccc2N3c2ccccc2)cc1]

EBM

TABLE 6-continued
Structural formulae of the materials used
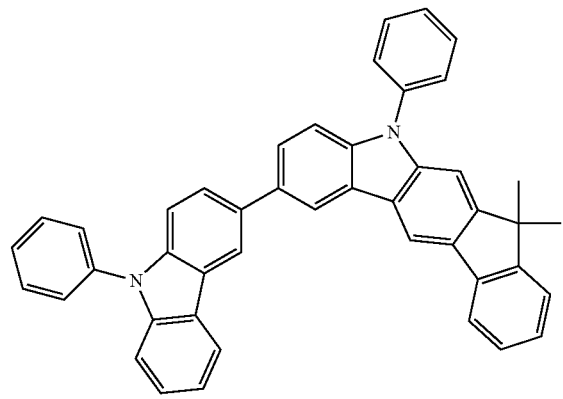 [SMILES: CC1(C)c2ccccc2-c2cc3c4cc(-c5ccc6c(c5)c5ccccc5n6-c5ccccc5)ccc4n(-c4ccccc4)c3cc21]
M1
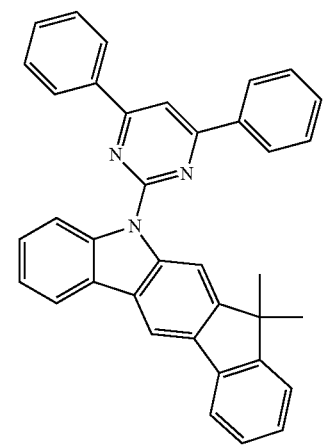 [SMILES: CC1(C)c2ccccc2-c2cc3c4ccccc4n(-c4nc(-c5ccccc5)cc(-c5ccccc5)n4)c3cc21]
M2
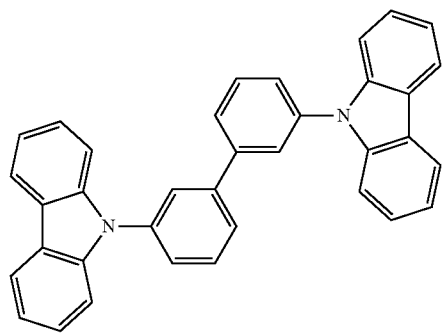 [SMILES: c1cc(-c2cccc(-n3c4ccccc4c4ccccc43)c2)cc(-n2c3ccccc3c3ccccc32)c1]
M3
TABLE 6-continued
Structural formulae of the materials used
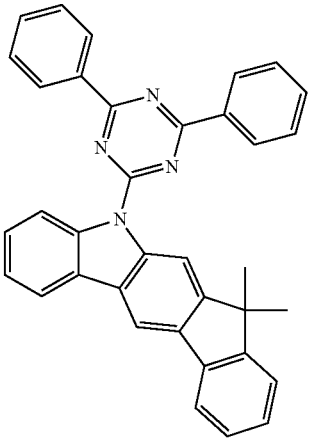 [SMILES: CC1(C)c2ccccc2-c2cc3c4ccccc4n(-c4nc(-c5ccccc5)nc(-c5ccccc5)n4)c3cc21]
HBM
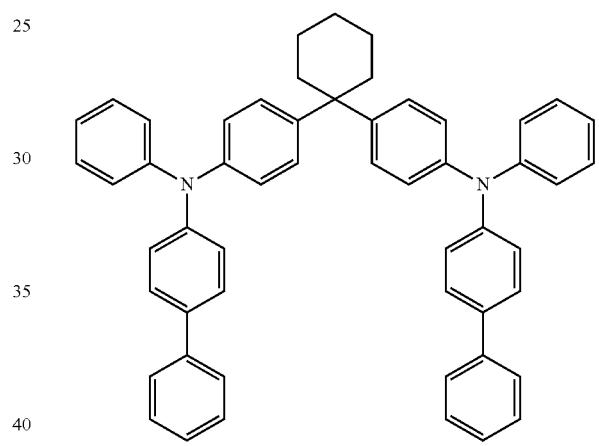
M4
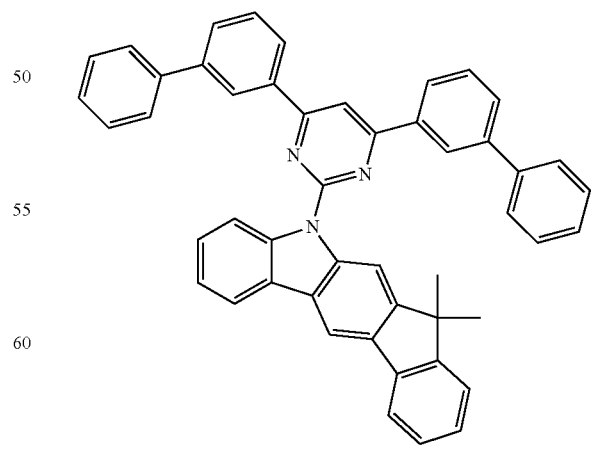
M5

TABLE 6-continued

Structural formulae of the materials used

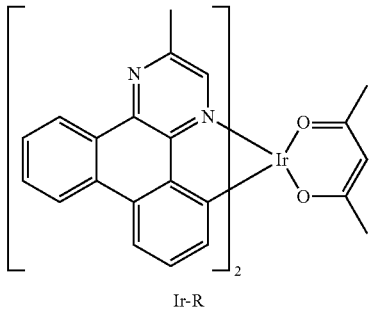

Ir-R

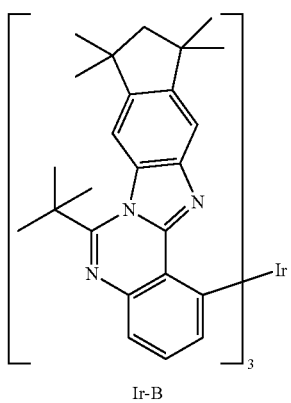

Ir-B

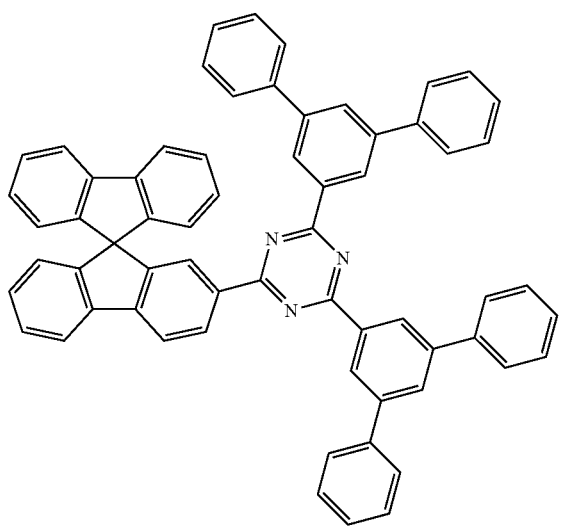 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

ETM1

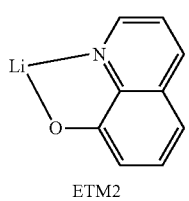

ETM2

TABLE 6-continued

Structural formulae of the materials used

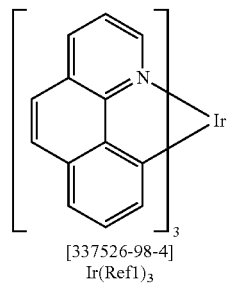

[337526-98-4]
Ir(Ref1)$_3$

The invention claimed is:

1. A compound of formula (1):

$$[Ir(L)_n(L')_m] \quad (1)$$

wherein the compound of formula (1) comprises a substructure Ir(L)$_n$ of formula (2):

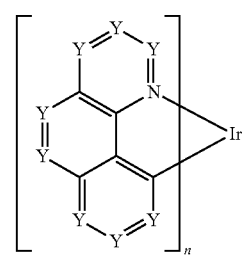

(2)

wherein

Y is the same or different in each instance and is CR or N, with the proviso that not more than one Y per cycle is N, or two adjacent Y together are a group of formula (3):

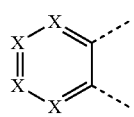

(3)

wherein the dotted bonds denote the linkage of this group in the ligand;

X is the same or different in each instance and is CR or N, with the proviso that not more than two X per ligand are N;

R is the same or different in each instance and is H, D, F, Cl, Br, I, N(R$^1$)$_2$, CN, Si(R$^1$)$_3$, B(OR$^1$)$_2$, C(=O)R$^1$, a straight-chain alkyl, alkoxy or thioalkoxy group having 1 to 40 carbon atoms, a straight-chain alkenyl or alkynyl group having 2 to 40 carbon atoms, or a branched or cyclic alkyl, alkenyl, alkynyl, alkoxy, or thioalkoxy group having 3 to 40 carbon atoms, each of which is optionally substituted by one or more R$^1$ radicals, wherein one or more nonadjacent CH$_2$ groups are optionally replaced by R$^1$C=CR$^1$, Si(R$^1$)$_2$, C=O, NR$^1$, O, S, or CONR$^1$ and wherein one or more hydrogen atoms are optionally replaced by D, F, or CN, or an aromatic or heteroaromatic ring system having 5 to 60 aromatic ring atoms and is optionally substituted by one or more R¹ radicals, an aryloxy or heteroaryloxy group having 5 to 60 aromatic ring atoms and is optionally substituted by one or more R¹ radicals, or a diarylamino group, diheteroarylamino group, or arylheteroarylamino group having 10 to 40 aromatic ring atoms and is optionally substituted by one or more R¹ radicals; and wherein two or more adjacent R radicals together optionally define a mono- or polycyclic, aliphatic, aromatic and/or benzofused ring system;

R¹ is the same or different in each instance and is H, D, F, Cl, Br, I, N(R²)₂, CN, Si(R²)₃, B(OR²)₂, C(=O)R², a straight-chain alkyl, alkoxy, or thioalkoxy group having 1 to 40 carbon atoms, or a straight-chain alkenyl or alkynyl group having 2 to 40 carbon atoms, or a branched or cyclic alkyl, alkenyl, alkynyl, alkoxy, or thioalkoxy group having 3 to 40 carbon atoms, each of which is optionally substituted by one or more R² radicals, wherein one or more nonadjacent CH₂ groups are optionally replaced by R²C=CR², Si(R²)₂, C=O, NR², O, S, or CONR² and wherein one or more hydrogen atoms are optionally replaced by D, F, or CN, or an aromatic or heteroaromatic ring system having 5 to 60 aromatic ring atoms and is optionally substituted by one or more R² radicals, an aryloxy or heteroaryloxy group having 5 to 60 aromatic ring atoms and is optionally substituted by one or more R² radicals, or a diarylamino group, diheteroarylamino group, or arylheteroarylamino group having 10 to 40 aromatic ring atoms and is optionally substituted by one or more R² radicals; and wherein two or more adjacent R¹ radicals together optionally define a mono- or polycyclic, aliphatic ring system;

R² is the same or different in each instance and is H, D, F, or an aliphatic, aromatic, and/or heteroaromatic organic radical having 1 to 20 carbon atoms, wherein one or more hydrogen atoms are optionally replaced by D or F; and wherein two or more R² substituents together optionally define a mono- or polycyclic, aliphatic or aromatic ring system;

L' is the same or different in each instance and is a mono- or bidentate ligand;

n is 1, 2, or 3;

m is 0, 1, 2, 3, or 4;

wherein, in the substructure of formula (2), two adjacent Y are CR and the respective R radicals together with the carbon atoms to which they are attached define a ring of formula (4) or formula (5) and/or two adjacent Y are a group of formula (3) and two adjacent X in the group of formula (3) are CR and the respective R radicals together with the carbon atoms to which they are attached define a ring of formula (4) or formula (5):

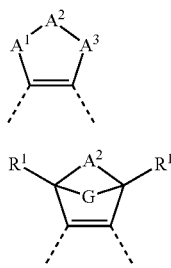

wherein the dotted bonds denote the linkage of the two carbon atoms in the ligand;

A¹ and A³ are the same or different in each instance and are C(R³)₂, O, S, NR³, or C(=O);

A² is C(R¹)₂, O, S, NR³, or C(=O);

G is an alkylene group having 1, 2, or 3 carbon atoms and is optionally substituted by one or more R² radicals, —CR²=CR²—, or an ortho-bonded arylene or heteroarylene group having 5 to 14 aromatic ring atoms and is optionally substituted by one or more R² radicals;

R³ is the same or different in each instance and is F, a straight-chain alkyl or alkoxy group having 1 to 10 carbon atoms, a branched or cyclic alkyl or alkoxy group having 3 to 10 carbon atoms, each of which is optionally substituted by one or more R² radicals, wherein one or more nonadjacent CH₂ groups are optionally replaced by R²C=CR², C=C, Si(R²)₂, C=O, NR², O, S, or CONR², and wherein one or more hydrogen atoms are optionally replaced by D or F, an aromatic or heteroaromatic ring system having 5 to 24 aromatic ring atoms and is optionally substituted by one or more R² radicals, an aryloxy or heteroaryloxy group having 5 to 24 aromatic ring atoms and is optionally substituted by one or more R² radicals, or an aralkyl or heteroaralkyl group having 5 to 24 aromatic ring atoms and is optionally substituted by one or more R² radicals; and wherein two R³ radicals bonded to the same carbon atom together optionally define an aliphatic or aromatic ring system and thus form a spiro system; and wherein R³ with an adjacent R or R¹ radical optionally defines an aliphatic ring system;

with the proviso that no two heteroatoms in A¹-A²-A¹ are bonded directly to one another and no two C=O groups are bonded directly to one another.

2. The compound of claim 1, wherein n is 3 and m is 0, or n is 2 and m is 1, wherein L' is a bidentate ligand which coordinates to the iridium via one carbon atom and one nitrogen atom, one carbon atom and one oxygen atom, two oxygen atoms, two nitrogen atoms, or one oxygen atom and one nitrogen atom, or n is 1 and m is 2, where L' is an ortho-metalated ligand which coordinates to the iridium via one carbon atom and one nitrogen or oxygen atom.

3. The compound of claim 1, wherein the substructure Ir(L)ₙ is selected from the group consisting of structures of formulae (6) through (15):

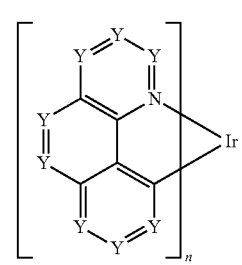

Formula (6)

-continued

Formula (7)
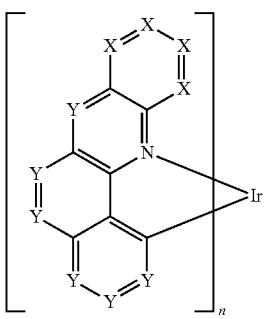

Formula (8)
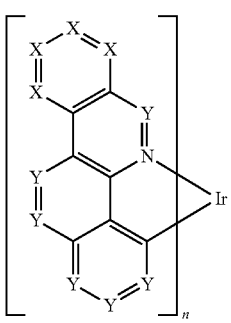

Formula (9)
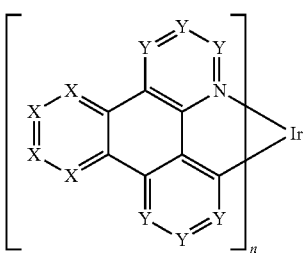

Formula (10)
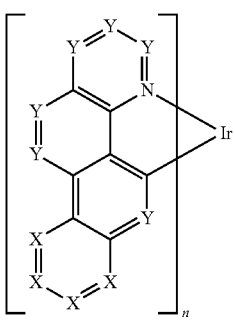

Formula (11)
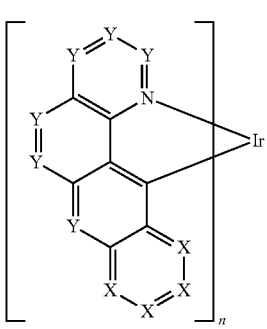

Formula (12)
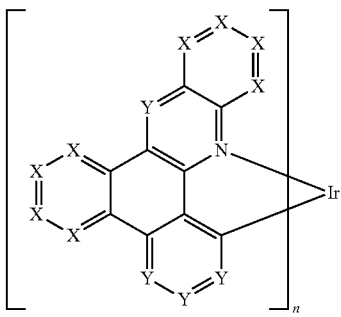

Formula (13)
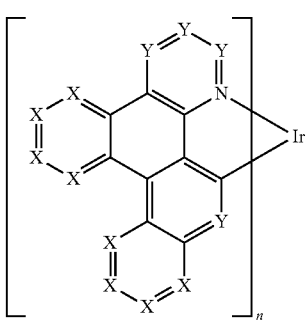

Formula (14)
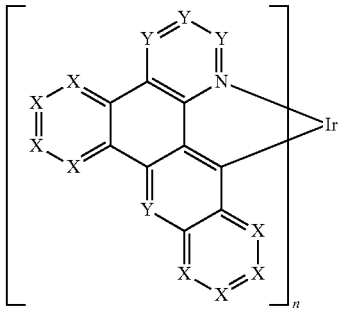

Formula (15)
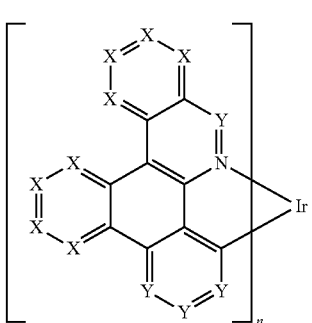

wherein Y is the same or different in each instance and is CR or N.

4. The compound of claim 1, wherein a total of 0, 1, or 2 of Y and, if present, X in L are N.

5. The compound of claim 1, wherein the substructure Ir(L)$_n$ is selected from the group consisting of structures of formulae (6-1) through (6-7), (7-1) through (7-6), (8-1) through (8-5), (9-1) through (9-5), (10-1) through (10-5), (11-1) through (11-6), (12-1) through (12-4), (13-1) through (13-3), (14-1) through (14-4), and (15-1) through (15-3):

Formula (6-1)
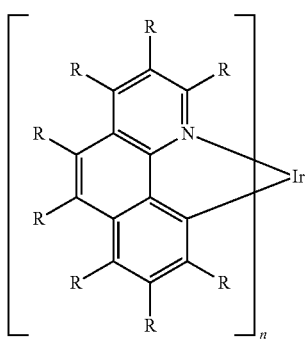
Formula (6-2)
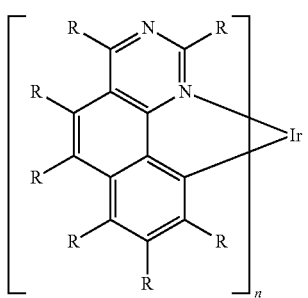
Formula (6-3)
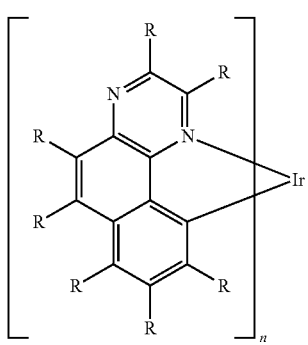
Formula (6-4)
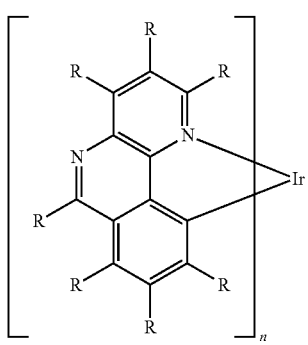
Formula (6-5)
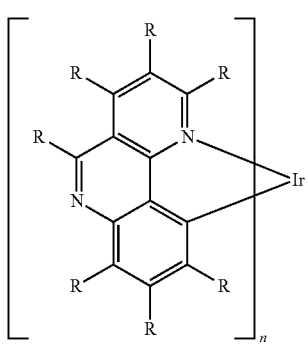
Formula (6-6)
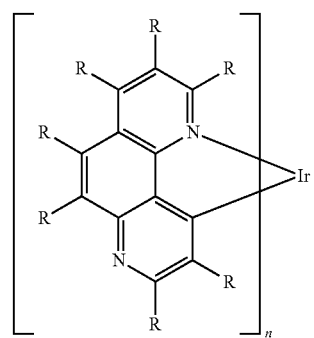
Formula (6-7)
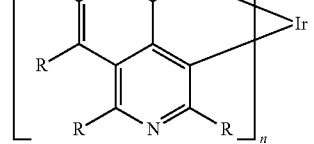
Formula (7-1)
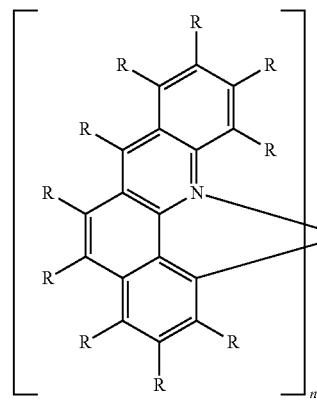
Formula (7-2)
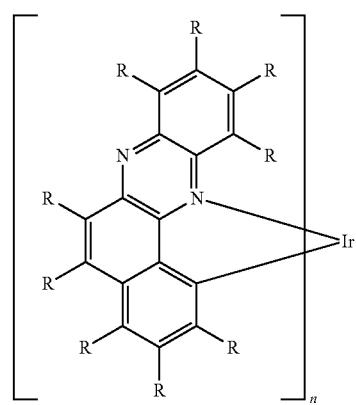

Formula (7-3)
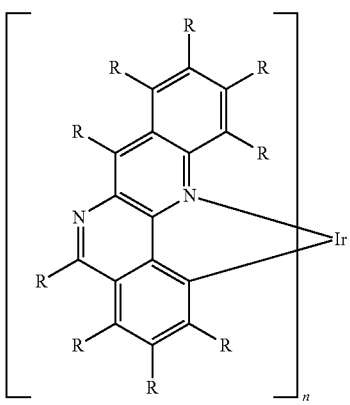
Formula (7-4)
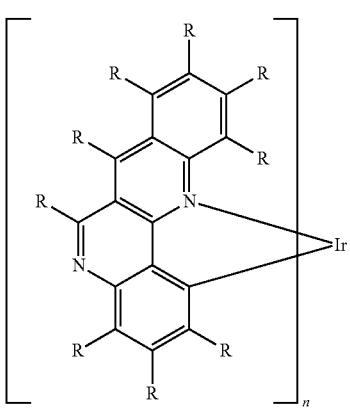
Formula (7-5)
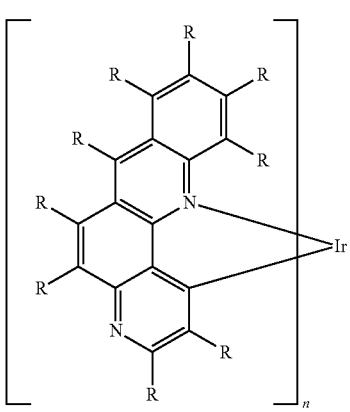
Formula (7-6)
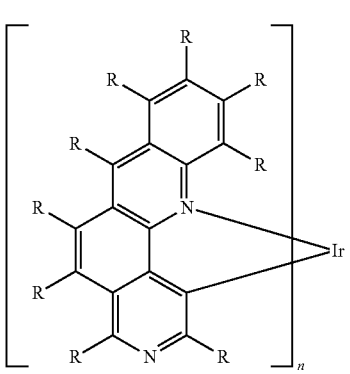
Formula (8-1)
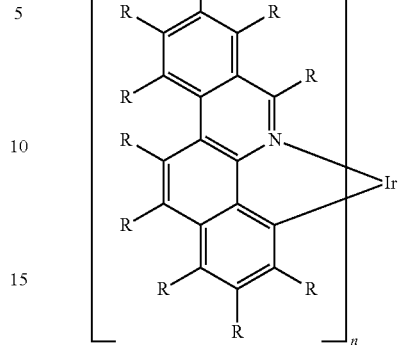
Formula (8-2)
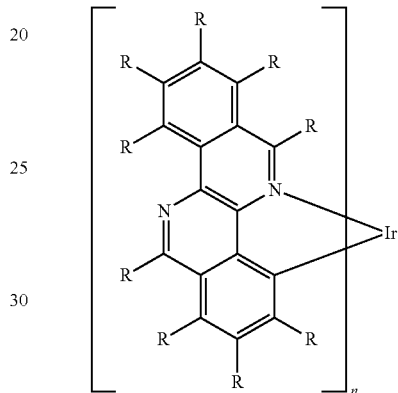
Formula (8-3)
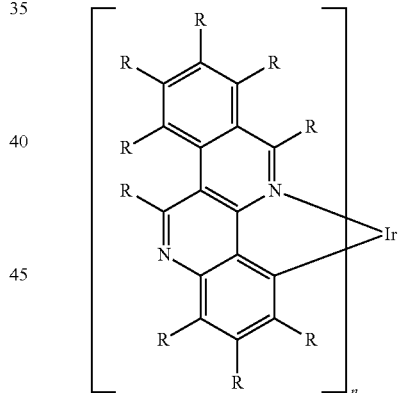
Formula (8-4)
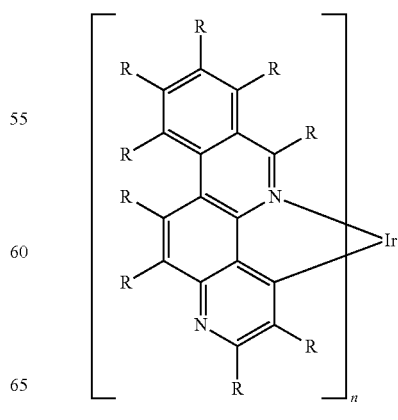

Formula (8-5)
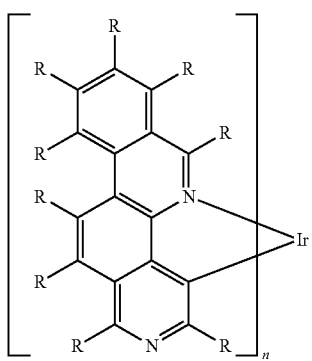
Formula (9-1)
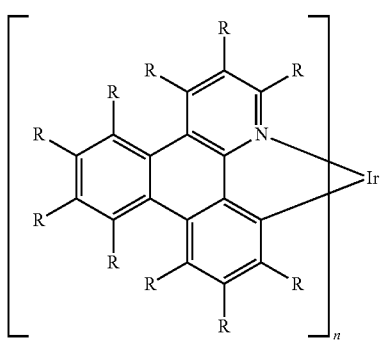
Formula (9-2)
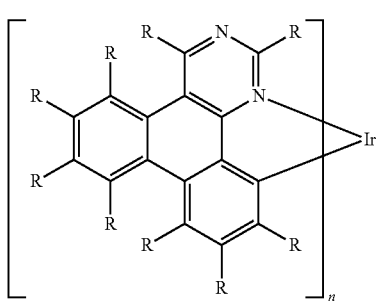
Formula (9-3)
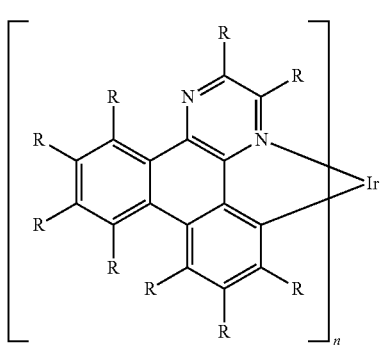
Formula (9-4)
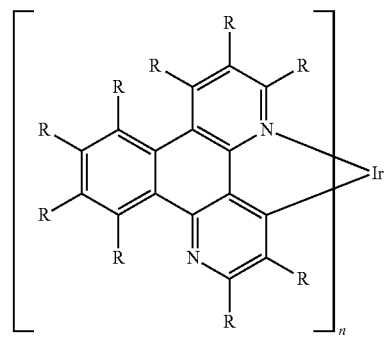
Formula (9-5)
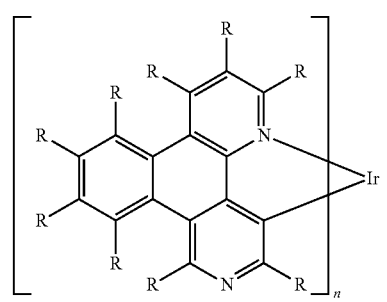
Formula (10-1)
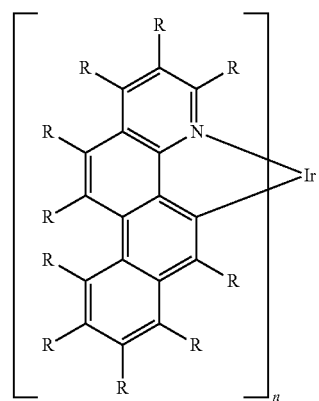
Formula (10-2)
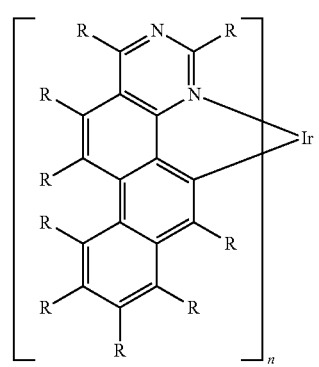

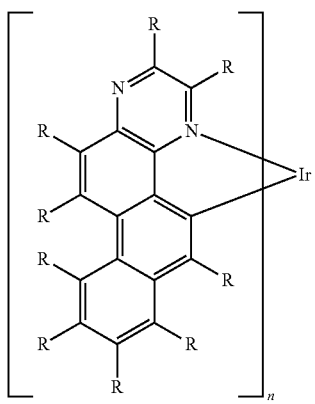
Formula (10-3)
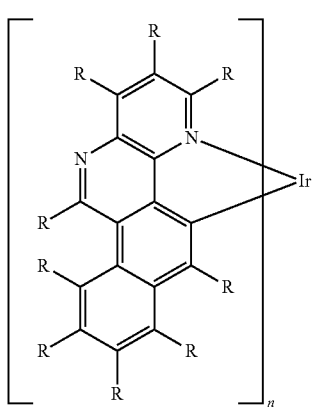
Formula (10-4)
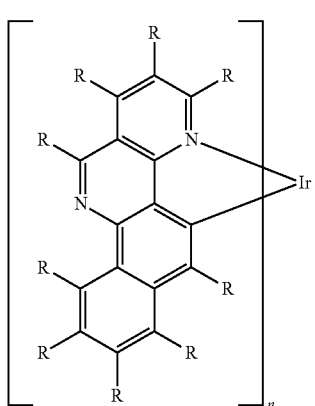
Formula (10-5)
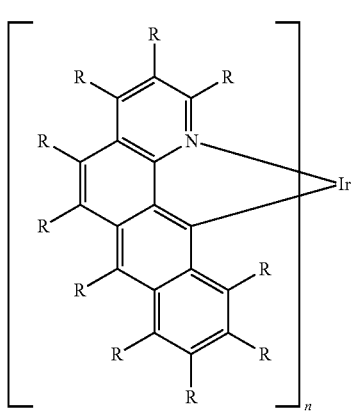
Formula (11-1)
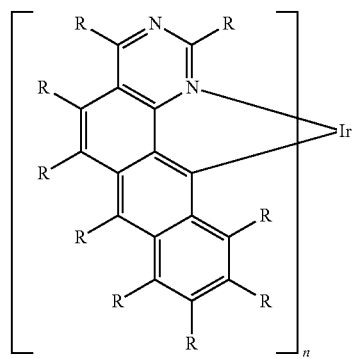
Formula (11-2)
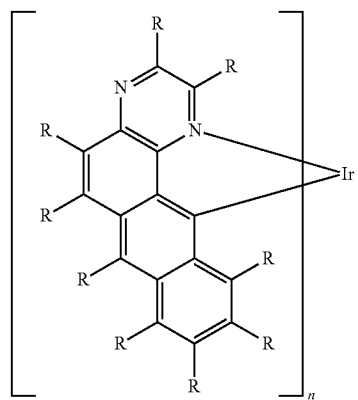
Formula (11-3)
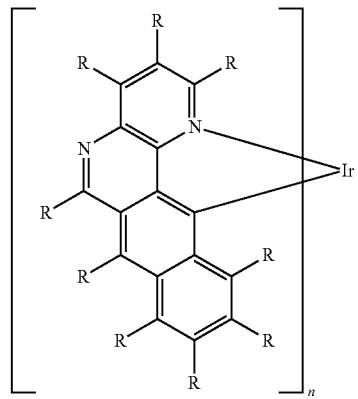
Formula (11-4)
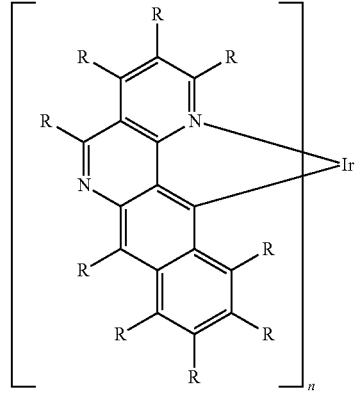
Formula (11-5)

Formula (11-6)
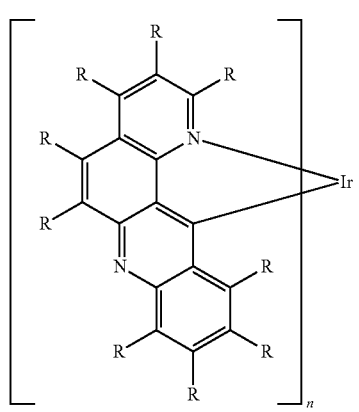
Formula (12-1)
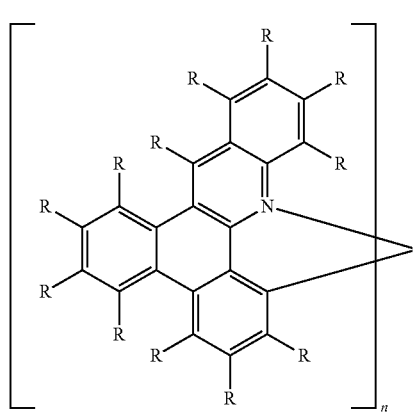
Formula (12-2)
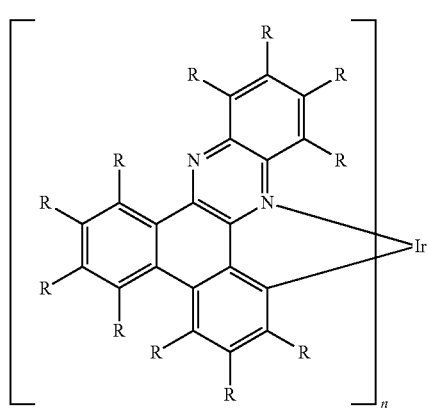
Formula (12-3)
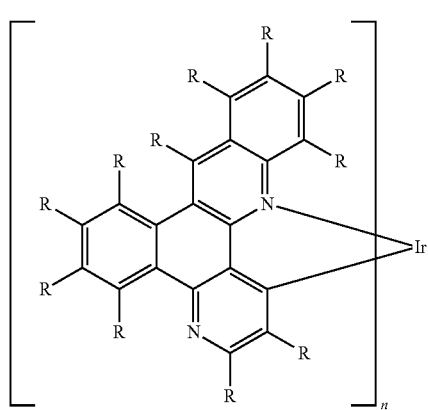
Formula (12-4)
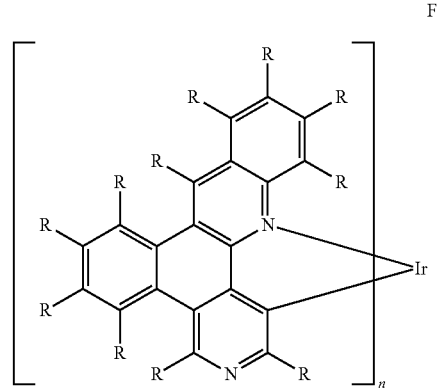
Formula (13-1)
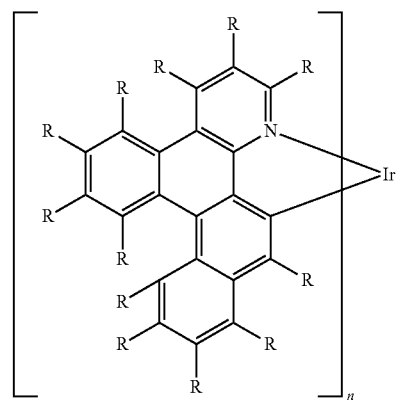
Formula (13-2)
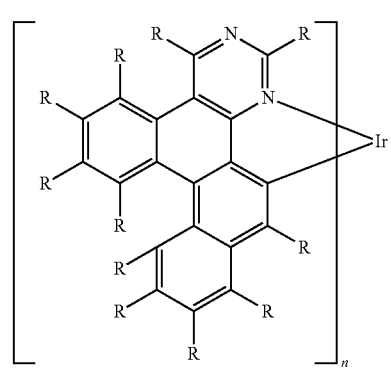
Formula (13-3)
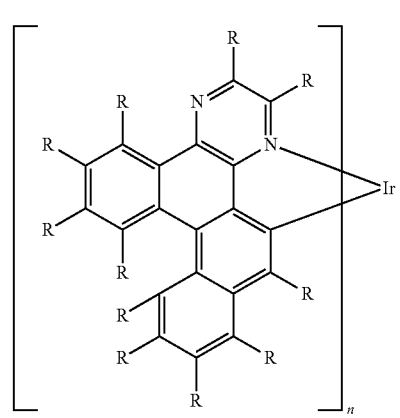

-continued

Formula (14-1)

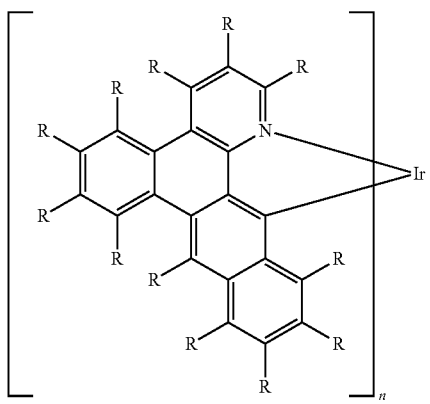

Formula (14-2)

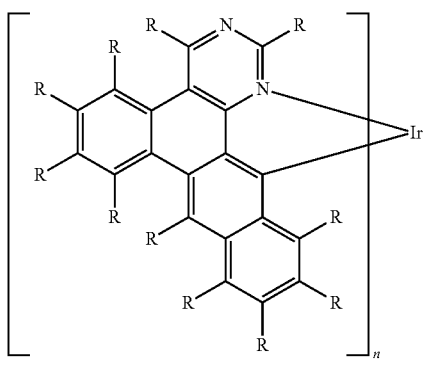

Formula (14-3)

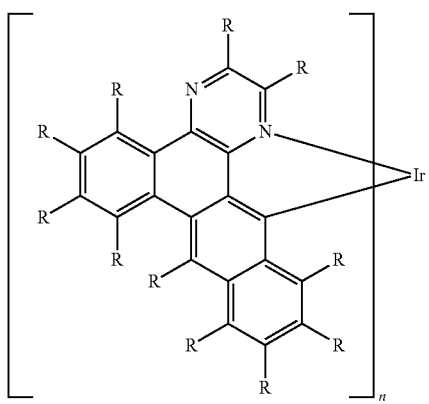

Formula (14-4)

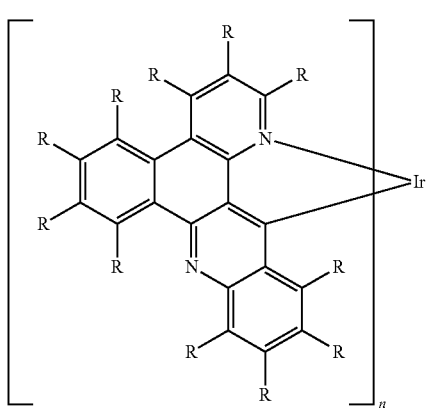

-continued

Formula (15-1)

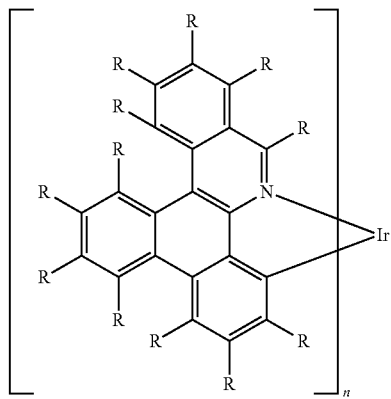

Formula (15-2)

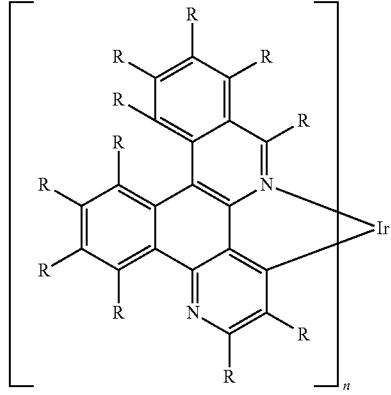

Formula (15-3)

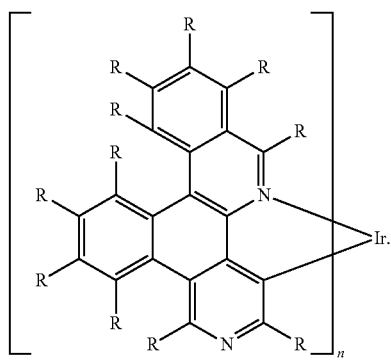

6. The compound of claim 1, wherein one or more of Y and/or X are N and a substituent R bonded adjacent to N is selected from the group consisting of $CF_3$, $OCF_3$, alkyl or alkoxy groups having 1 to 10 carbon atoms, a dialkylamino group having 2 to 10 carbon atoms, aromatic or heteroaromatic ring systems optionally substituted by one or more substituents $R^1$, or aralkyl or heteroaralkyl groups optionally substituted by one or more substituents $R^1$, or wherein the substituent R bonded adjacent to N is incorporated in a structure of formula (4) or (5).

7. The compound of claim 1, wherein the substructure $Ir(L)_n$ is selected from the group consisting of substructures of formulae (6a) through (15h):

Formula (6a)
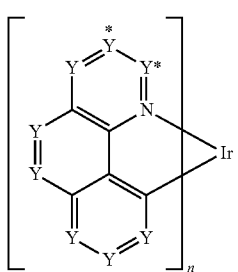
Formula (6b)
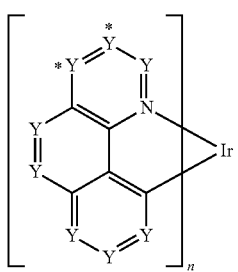
Formula (6c)
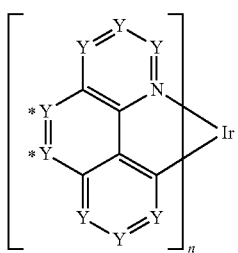
Formula (6d)
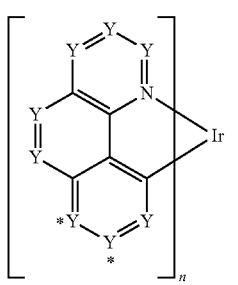
Formula (6e)
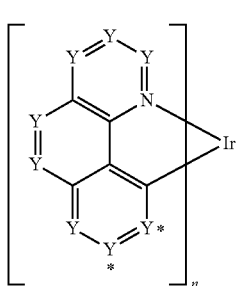
Formula (7a)
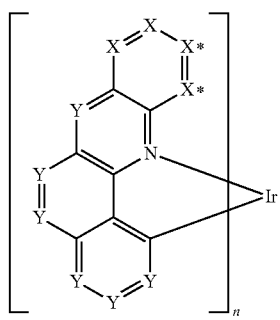
Formula (7b)
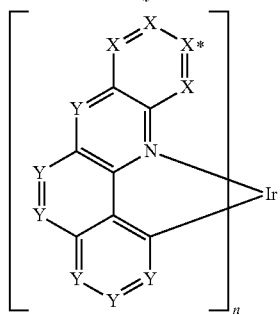
Formula (7c)
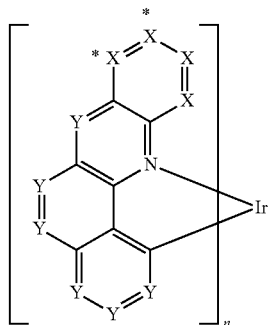
Formula (7d)
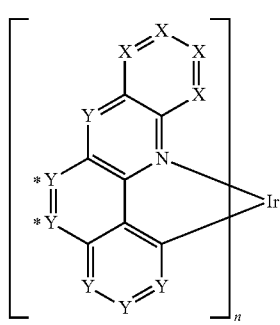
Formula (7e)
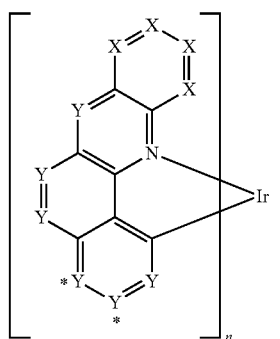

Formula (7f)
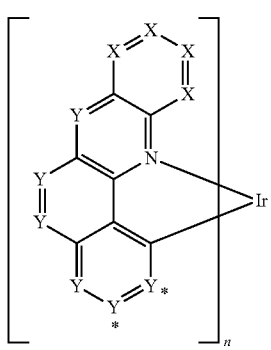
Formula (8a)
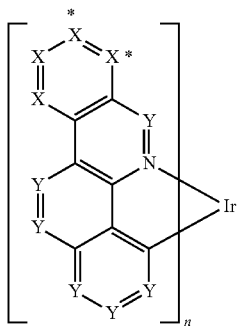
Formula (8b)
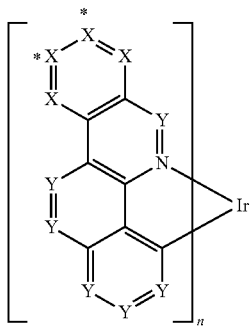
Formula (8c)
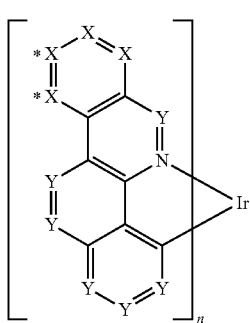
Formula (8d)
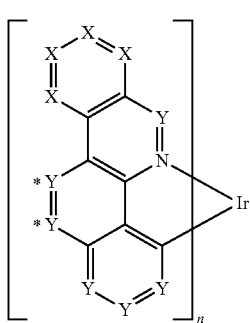
Formula (8e)
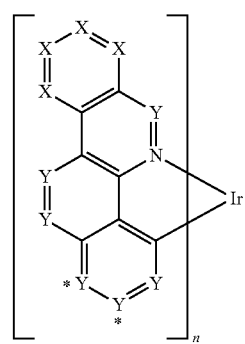
Formula (8f)
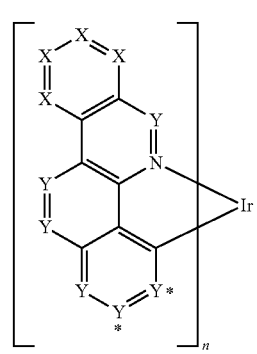
Formula (9a)
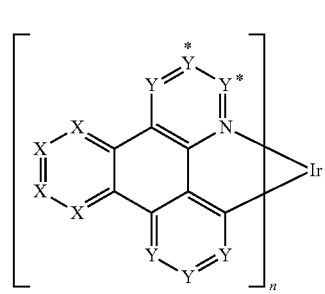
Formula (9b)
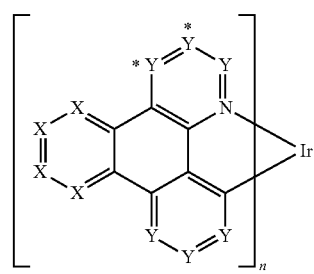
Formula (9c)
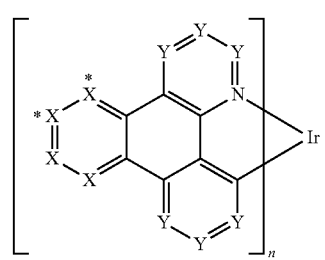

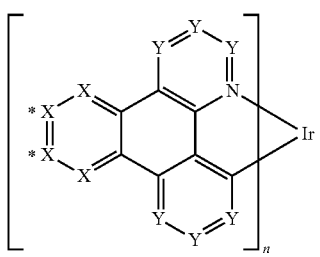
Formula (9d)
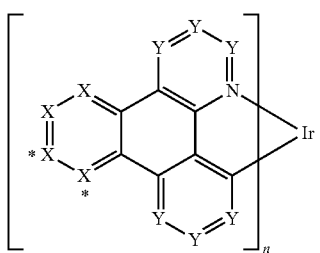
Formula (9e)
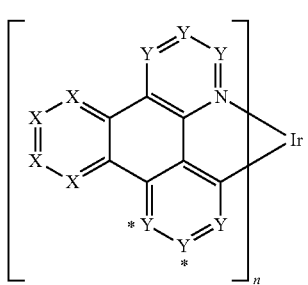
Formula (9f)
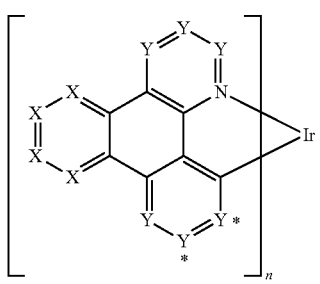
Formula (9g)
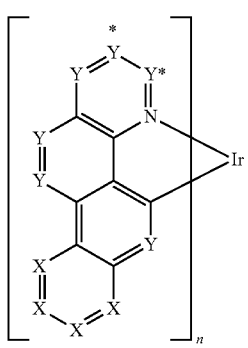
Formula (10a)
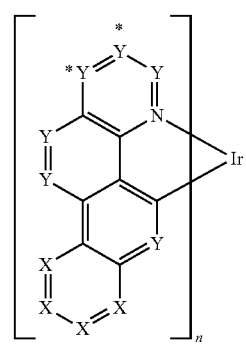
Formula (10b)
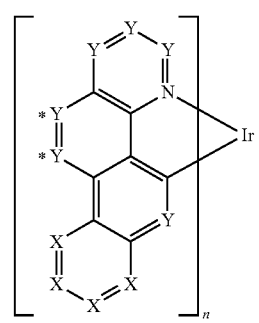
Formula (10c)
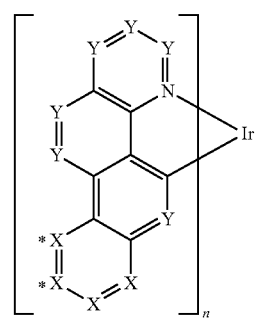
Formula (10d)
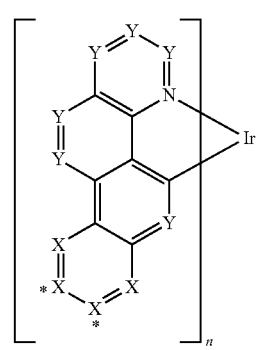
Formula (10e)

Formula (10f)
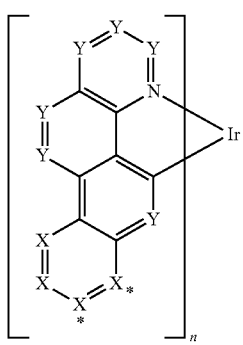
Formula (11a)
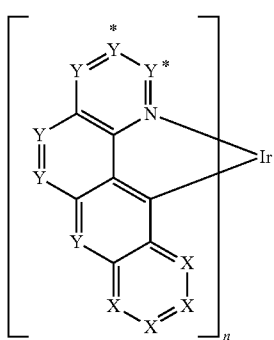
Formula (11b)
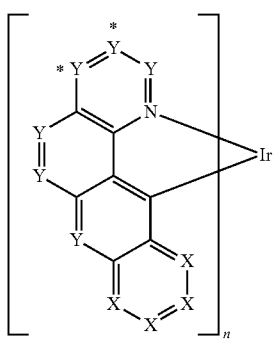
Formula (11c)
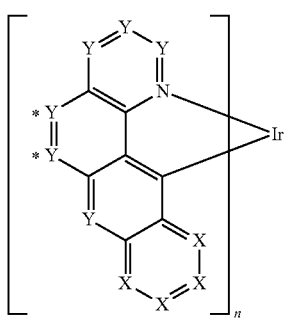
Formula (11d)
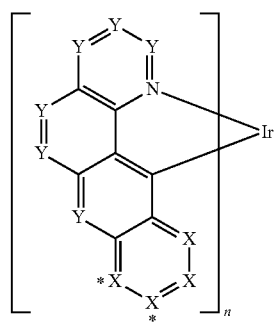
Formula (11e)
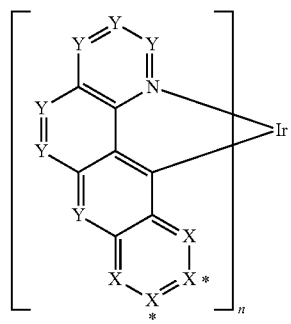
Formula (11f)
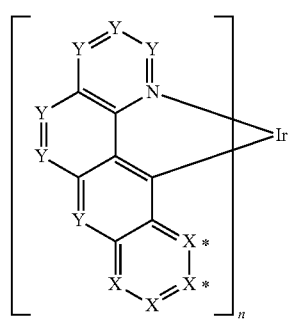
Formula (12a)
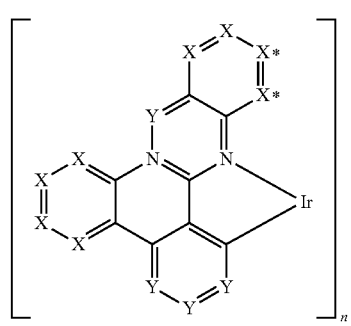
Formula (12b)
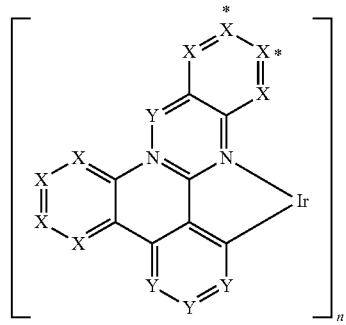

261
-continued
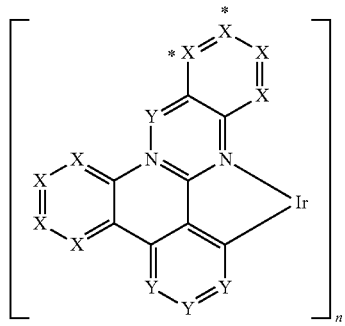
Formula (12c)
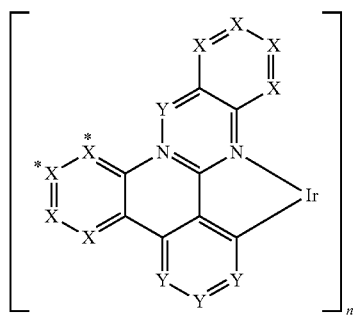
Formula (12d)
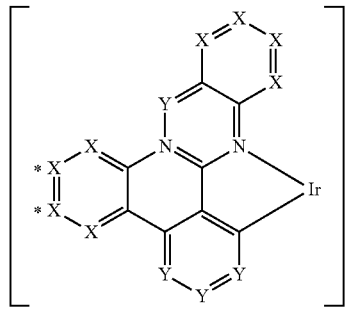
Formula (12e)
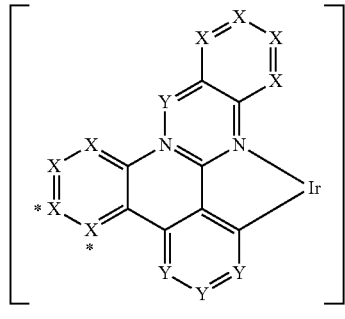
Formula (12f)
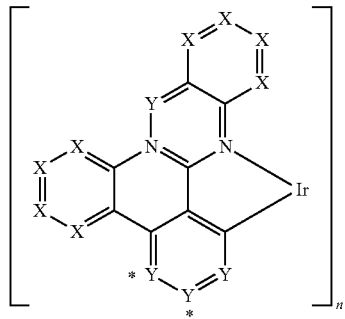
Formula (12g)
262
-continued
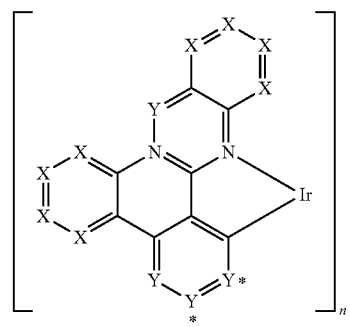
Formula (12h)
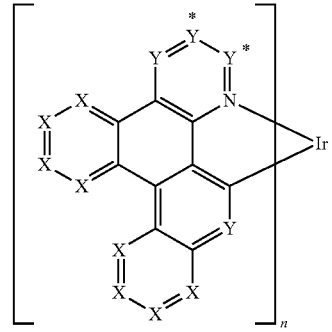
Formula (13a)
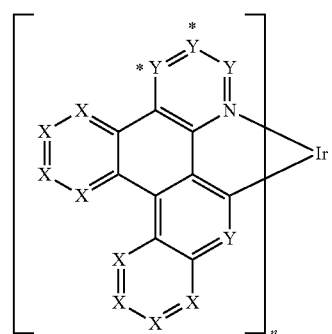
Formula (13b)
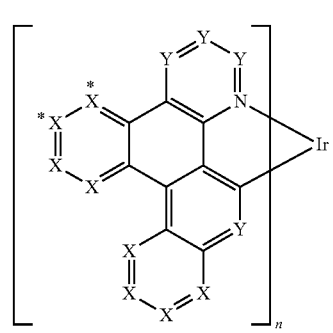
Formula (13c)
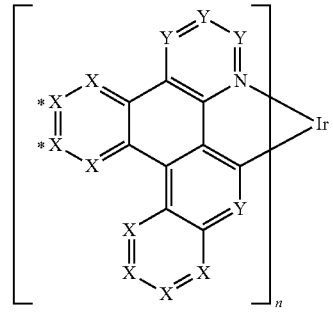
Formula (13d)

Formula (13e)
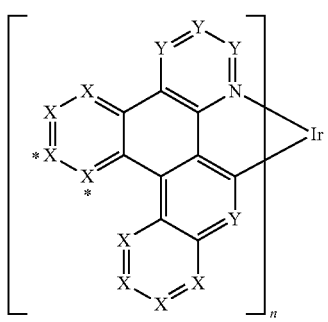
Formula (13f)
Formula (13g)
Formula (13h)
Formula (14a)
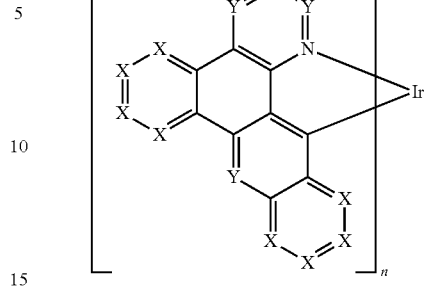
Formula (14b)
Formula (14c)
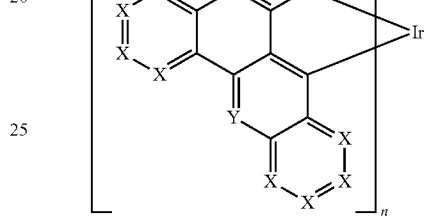
Formula (14d)
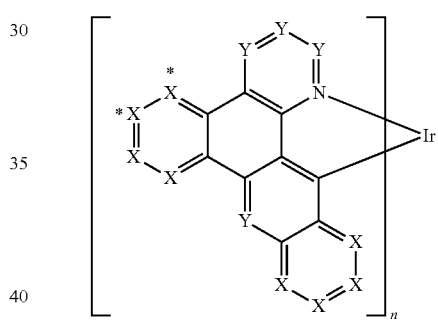
Formula (14e)
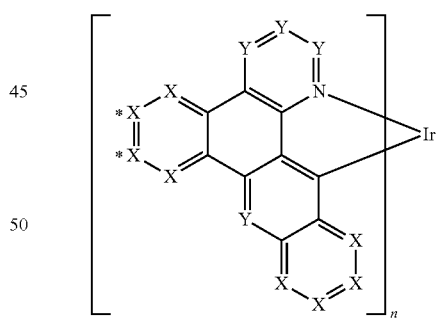
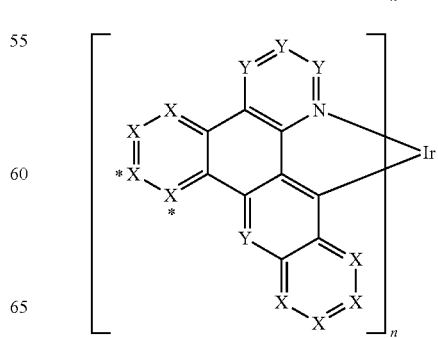

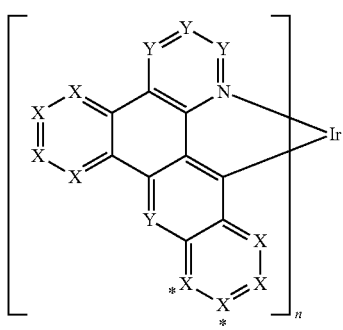
Formula (14f)
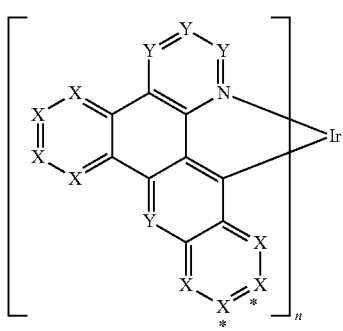
Formula (14g)
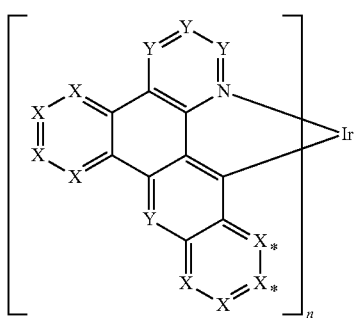
Formula (14h)
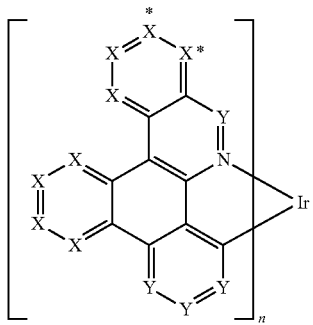
Formula (15a)
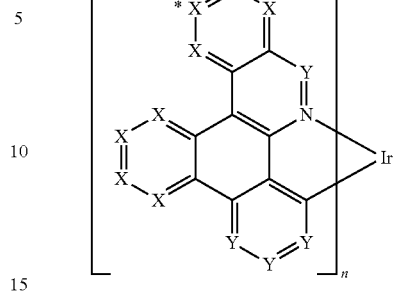
Formula (15b)
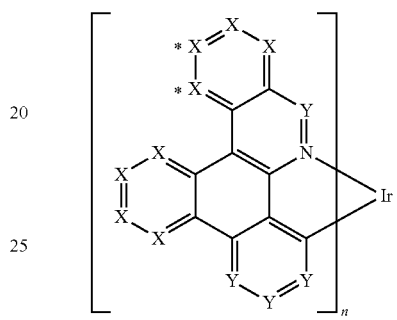
Formula (15c)
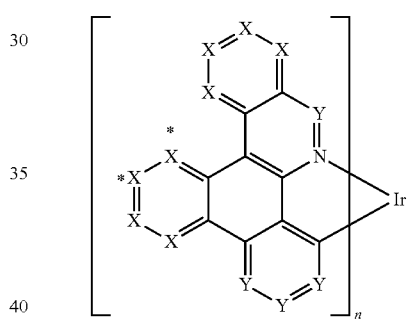
Formula (15d)
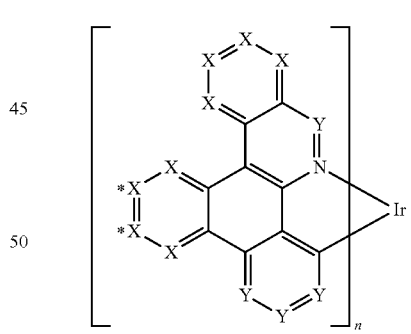
Formula (15e)
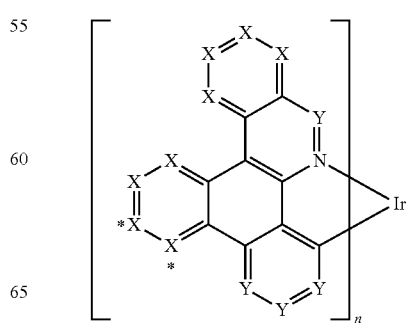
Formula (15f)

Formula (15g)

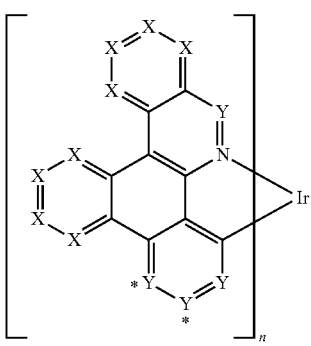

Formula (15h)

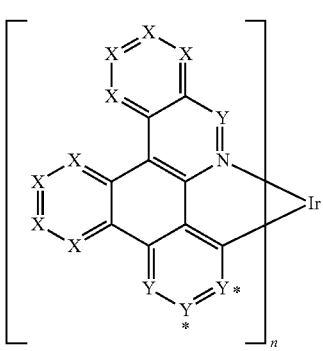

wherein * in each case denotes the position at which the two adjacent Y or X are CR and the respective R radicals together with the carbon atoms to which they are attached define a ring of formula (4) or formula (5).

8. The compound of claim 1, wherein the structure of formula (4) is selected from the group consisting of formulae (4-A), (4-B), (4-C), (4-D), and (4-E):

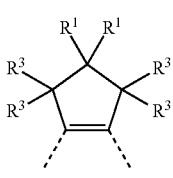 (4-a)

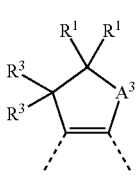 (4-b)

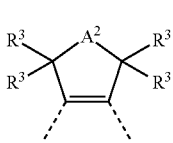 (4-c)

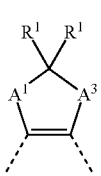 (4-d)

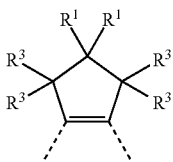 (4-e)

wherein
$A^1$, $A^2$ and $A^3$ are the same or different in each instance and are O or $NR^3$, and
wherein the structure of formula (5) is selected from the group consisting of formulae (5-A), (5-B), and (5-C):

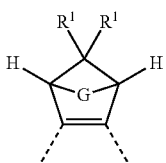 (5-A)

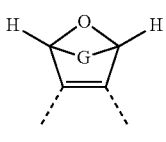 (5-B)

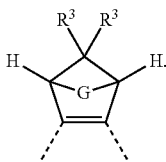 (5-C)

9. The compound of claim 1, wherein $R^3$ is the same or different in each instance and is F, a straight-chain alkyl group having 1 to 10 carbon atoms or a branched or cyclic alkyl group having 3 to 20 carbon atoms, wherein one or more nonadjacent $CH_2$ groups or optionally replaced by $R^2C=CR^2$ and one or more hydrogen atoms are optionally replaced by D or F, or an aromatic or heteroaromatic ring system having 5 to 14 aromatic ring atoms and is optionally substituted by one or more $R^2$ radicals; and wherein two $R^3$ radicals bonded to the same carbon atom together optionally define an aliphatic or aromatic ring system and thus form a spiro system; and wherein $R^3$ optionally defines an aliphatic ring system with an adjacent R or $R^1$ radical.

10. A process for preparing the compound of claim 1 comprising reacting the ligand with an iridium alkoxide of formula (44), an iridium ketoketonate of formula (45), an iridium halide of formula (46), or a dimeric iridium complex of formula (47) or (48):

$$Ir(OR^1)_n \quad (44)$$

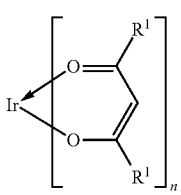 (45)

-continued

IrHal$_n$ (46)

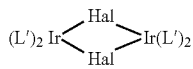 (47)

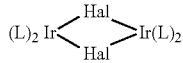 (48)

wherein Hal is F, Cl, Br, or I, or reacting the ligand L with an iridium complex of formula [Ir(L')$_2$(HOMe)$_2$]A or [Ir(L')$_2$(NCMe)$_2$]A or reacting the ligand L' with an iridium complex of formula [Ir(L)$_2$(HOMe)$_2$]A or [Ir(L)$_2$(NCMe)$_2$]A, wherein A is a non-coordinating anion, or reacting the ligand with an iridium compound having both alkoxide and/or halide and/or hydroxyl radicals and ketoketonate radicals.

11. A formulation comprising at least one compound of claim 1 and at least one further compound.

12. The formulation of claim 11, wherein the at least one further compound is a solvent.

13. An electronic device comprising at least one compound of claim 1.

14. The electronic device of claim 13, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, and organic laser diodes.

15. The electronic device of claim 14, wherein the electronic device is an organic electroluminescent device, wherein the compound is used as an emitting compound in one or more emitting layers comprising a matrix material.

16. The electronic device of claim 15, wherein the matrix material comprises ketones, phosphine oxides, sulfoxides, sulfones, triarylamines, carbazoles, indolocarbazoles, indenocarbazoles, azacarbazoles, bipolar matrix materials, azaboroles, boronic esters, diazasiloles, diazaphospholes, triazines, zinc complexes, beryllium complexes, dibenzofurans, and/or bridged carbazole derivatives.

* * * * *